(12) United States Patent
Emery et al.

(10) Patent No.: US 10,603,521 B2
(45) Date of Patent: Mar. 31, 2020

(54) BAND TRANSDUCER ULTRASOUND THERAPY

(71) Applicant: Ulthera, Inc., Mesa, AZ (US)

(72) Inventors: Charles D. Emery, Gilbert, AZ (US); Michael T. Peterson, Scottsdale, AZ (US); Joshua D. Hope, Gilbert, AZ (US)

(73) Assignee: Ulthera, Inc., Mesa, AZ (US)

( * ) Notice: Subject to any disclaimer, the term of this patent is extended or adjusted under 35 U.S.C. 154(b) by 0 days.

(21) Appl. No.: 15/855,949

(22) Filed: Dec. 27, 2017

(65) Prior Publication Data
US 2018/0117366 A1 May 3, 2018

Related U.S. Application Data

(63) Continuation of application No. 15/302,436, filed as application No. PCT/US2015/025581 on Apr. 13, 2015, now abandoned.
(Continued)

(51) Int. Cl.
*A61N 7/02* (2006.01)
*G10K 11/30* (2006.01)
(Continued)

(52) U.S. Cl.
CPC .............. *A61N 7/02* (2013.01); *G10K 11/30* (2013.01); *G10K 11/352* (2013.01);
(Continued)

(58) Field of Classification Search
CPC .............. A61N 7/02; A61N 2007/0034; A61N 2007/0065; A61N 2007/0078;
(Continued)

(56) References Cited

U.S. PATENT DOCUMENTS 2,427,348 A 9/1947 Bond et al.
2,792,829 A 2/1952 Calosi
(Continued)

FOREIGN PATENT DOCUMENTS

CN 1734284 12/2009
CN 104027893 9/2014
(Continued)

OTHER PUBLICATIONS

PCT/US2015/025581 International Search Report dated Jul. 14, 2015.
(Continued)

*Primary Examiner* — Carolyn A Pehlke
(74) *Attorney, Agent, or Firm* — Knobbe Martens Olson & Bear LLP

(57) ABSTRACT

Embodiments of a dermatological cosmetic treatment and/or imaging system and method can include use of transducer to create a linear thermal treatment zone at a focal depth to form a band shaped treatment area. The system can include one or more ultrasound transducers, a cylindrical transduction element, an imaging element, a hand wand, a removable transducer module, a control module, and/or graphical user interface. In some embodiments, a coated transducer may be used to provide more consistent treatment in cosmetic procedures, including brow lifts, fat reduction, sweat reduction, and treatment of the décolletage. Skin tightening, lifting and amelioration of wrinkles and stretch marks are provided. Treatment may include heating of tissue for a duration to deactivate a percentage of cells in the treatment region.

20 Claims, 47 Drawing Sheets

Related U.S. Application Data

(60) Provisional application No. 61/981,660, filed on Apr. 18, 2014.

(51) Int. Cl.
  *G10K 11/35* (2006.01)
  *A61B 17/00* (2006.01)
  *A61N 7/00* (2006.01)

(52) U.S. Cl.
  CPC ............... *A61B 2017/00084* (2013.01); *A61B 2017/00106* (2013.01); *A61N 2007/0034* (2013.01); *A61N 2007/0065* (2013.01); *A61N 2007/0078* (2013.01); *A61N 2007/0082* (2013.01); *A61N 2007/0091* (2013.01)

(58) Field of Classification Search
  CPC ... A61N 2007/0082; A61N 2007/0091; G10K 11/30; G10K 11/352; A61B 2017/00084; A61B 2017/00106
  See application file for complete search history.

(56) References Cited

U.S. PATENT DOCUMENTS

| | | |
|---|---|---|
| 3,913,386 A | 10/1975 | Saglio |
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,151,834 A | 5/1979 | Sato et al. |
| 4,166,967 A | 9/1979 | Benes et al. |
| 4,211,948 A | 7/1980 | Smith et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Taenzer |
| 4,417,170 A | 11/1983 | Benisncasa |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,881,212 A | 11/1989 | Takeuchi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh |
| 4,917,096 A | 4/1990 | Englehart |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry |
| 5,040,537 A | 8/1991 | Katakura |
| 5,054,310 A | 10/1991 | Flynn |
| 5,054,470 A | 10/1991 | Fry |
| 5,054,491 A | 10/1991 | Saito et al. |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi |
| 5,123,418 A | 6/1992 | Saurel |
| 5,142,511 A | 8/1992 | Kanai et al. |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |
| 5,163,436 A | 11/1992 | Saitoh et al. |
| 5,178,135 A | 1/1993 | Uchiyama et al. |
| 5,190,518 A | 3/1993 | Takasu |
| 5,190,766 A | 3/1993 | Ishihara |
| 5,191,880 A | 3/1993 | McLeod |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | D'Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa |
| 5,267,985 A | 12/1993 | Shimada |
| 5,269,297 A | 12/1993 | Weng |
| 5,282,797 A | 2/1994 | Chess |
| 5,295,484 A | 3/1994 | Marcus |
| 5,295,486 A | 3/1994 | Wollschlager et al. |
| 5,304,169 A | 4/1994 | Sand |
| 5,305,756 A | 4/1994 | Entrekin et al. |
| 5,321,520 A | 6/1994 | Inga et al. |
| 5,323,779 A | 6/1994 | Hardy et al. |
| 5,327,895 A | 7/1994 | Hashimoto et al. |
| 5,329,202 A | 7/1994 | Garlick et al. |
| 5,348,016 A | 9/1994 | Unger et al. |
| 5,358,466 A | 10/1994 | Aida et al. |
| 5,360,268 A | 11/1994 | Hayashi |

(56) References Cited

U.S. PATENT DOCUMENTS

| | | |
|---|---|---|
| 5,370,121 A | 12/1994 | Reichenberger |
| 5,370,122 A | 12/1994 | Kunig |
| 5,371,483 A | 12/1994 | Bhardwaj |
| 5,375,602 A | 12/1994 | Lancee et al. |
| 5,379,773 A | 1/1995 | Hornsby |
| 5,380,280 A | 1/1995 | Peterson |
| 5,380,519 A | 1/1995 | Schneider et al. |
| 5,383,917 A | 1/1995 | Desai et al. |
| 5,391,140 A | 2/1995 | Schaetzle et al. |
| 5,391,197 A | 2/1995 | Burdette et al. |
| 5,392,259 A | 2/1995 | Bolorforosh |
| 5,396,143 A | 3/1995 | Seyed-Bolorforosh et al. |
| 5,398,689 A | 3/1995 | Connor et al. |
| 5,406,503 A | 4/1995 | Williams |
| 5,413,550 A | 5/1995 | Castel |
| 5,417,216 A | 5/1995 | Tanaka |
| 5,423,220 A | 6/1995 | Finsterwald et al. |
| 5,435,311 A | 7/1995 | Umemura |
| 5,438,998 A | 8/1995 | Hanafy |
| 5,443,068 A | 8/1995 | Cline et al. |
| 5,445,611 A | 8/1995 | Eppstein et al. |
| 5,458,596 A | 10/1995 | Lax |
| 5,460,179 A | 10/1995 | Okunuki et al. |
| 5,460,595 A | 10/1995 | Hall et al. |
| 5,419,327 A | 11/1995 | Rohwedder |
| 5,469,854 A | 11/1995 | Unger et al. |
| 5,471,488 A | 12/1995 | Fujio |
| 5,472,405 A | 12/1995 | Buchholtz et al. |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |
| 5,503,152 A | 4/1996 | Oakley et al. |
| 5,503,320 A | 4/1996 | Webster et al. |
| 5,507,790 A | 4/1996 | Weiss |
| 5,511,296 A | 4/1996 | Dias et al. |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenchein |
| 5,524,624 A | 6/1996 | Tepper |
| 5,524,625 A | 6/1996 | Okazaki |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,529,070 A | 6/1996 | Augustine et al. |
| 5,540,235 A | 7/1996 | Wilson |
| 5,558,092 A | 9/1996 | Unger |
| 5,560,362 A | 10/1996 | Sliwa et al. |
| 5,573,497 A | 11/1996 | Chapelon |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,643,179 A | 1/1997 | Fujimoto |
| 5,601,526 A | 2/1997 | Chapelon |
| 5,603,323 A | 2/1997 | Pflugrath et al. |
| 5,605,154 A | 2/1997 | Ries et al. |
| 5,609,562 A | 3/1997 | Kaali |
| 5,615,091 A | 3/1997 | Palatnik |
| 5,618,275 A | 4/1997 | Bock |
| 5,620,479 A | 4/1997 | Diederich |
| 5,622,175 A | 4/1997 | Sudol et al. |
| 5,617,858 A | 5/1997 | Taverna et al. |
| 5,638,819 A | 6/1997 | Manwaring et al. |
| 5,644,085 A | 7/1997 | Lorraine et al. |
| 5,647,373 A | 7/1997 | Paltieli |
| 5,655,535 A | 8/1997 | Frlemel et al. |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,662,116 A | 9/1997 | Kondo |
| 5,665,053 A | 9/1997 | Jacobs |
| 5,665,141 A | 9/1997 | Vago |
| 5,671,746 A | 9/1997 | Dreschel et al. |
| 5,673,699 A | 10/1997 | Trahey et al. |
| 5,676,692 A | 10/1997 | Sanghvi |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,763,886 A | 6/1998 | Schulte |
| 5,769,790 A | 6/1998 | Watkins |
| 5,779,644 A | 7/1998 | Eberle et al. |
| 5,792,058 A | 8/1998 | Lee |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,840,032 A | 11/1998 | Hatfield et al. |
| 5,844,140 A | 12/1998 | Seale |
| 5,853,367 A | 12/1998 | Chalek et al. |
| 5,869,751 A | 2/1999 | Bonin |
| 5,871,524 A | 2/1999 | Knowlton |
| 5,873,902 A | 2/1999 | Sanghvi |
| 5,876,341 A | 3/1999 | Wang et al. |
| 5,879,303 A | 3/1999 | Averkiou et al. |
| 5,882,557 A | 3/1999 | Hayakawa |
| 5,891,034 A | 4/1999 | Bucholz |
| 5,895,356 A | 4/1999 | Andrus et al. |
| 5,899,861 A | 5/1999 | Friemel et al. |
| 5,904,659 A | 5/1999 | Duarte |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,964,707 A | 10/1999 | Fenster et al. |
| 5,967,980 A | 10/1999 | Ferre et al. |
| 5,968,034 A | 10/1999 | Fullmer |
| 5,971,949 A | 10/1999 | Levin |
| 5,977,538 A | 11/1999 | Unger et al. |
| 5,984,881 A | 11/1999 | Ishibashi et al. |
| 5,984,882 A | 11/1999 | Rosenchein |
| 5,990,598 A | 11/1999 | Sudol et al. |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |

(56) References Cited

U.S. PATENT DOCUMENTS

| | | |
|---|---|---|
| 6,014,473 A | 1/2000 | Hossack et al. |
| 6,016,255 A | 1/2000 | Bolan et al. |
| 6,019,724 A | 2/2000 | Gronningsaeter et al. |
| 6,022,308 A | 2/2000 | Williams |
| 6,022,317 A | 2/2000 | Cruanas et al. |
| 6,022,327 A | 2/2000 | Chang |
| 6,030,374 A | 2/2000 | McDaniel |
| 6,036,646 A | 3/2000 | Barthe |
| 6,039,048 A | 3/2000 | Silberg |
| 6,039,689 A | 3/2000 | Lizzi |
| 6,042,556 A | 3/2000 | Beach |
| 6,049,159 A | 4/2000 | Barthe |
| 6,050,943 A | 4/2000 | Slayton |
| 6,059,727 A | 5/2000 | Fowlkes |
| 6,071,239 A | 6/2000 | Cribbs |
| 6,080,108 A | 6/2000 | Dunham |
| 6,083,148 A | 7/2000 | Williams |
| 6,086,535 A | 7/2000 | Ishibashi |
| 6,086,580 A | 7/2000 | Mordon et al. |
| 6,090,054 A | 7/2000 | Tagishi |
| 6,093,148 A | 7/2000 | Fujimoto |
| 6,093,883 A | 7/2000 | Sanghvi |
| 6,100,626 A | 8/2000 | Frey et al. |
| 6,101,407 A | 8/2000 | Groezinger |
| 6,106,469 A | 8/2000 | Suzuki et al. |
| 6,113,558 A | 9/2000 | Rosenchein |
| 6,113,559 A | 9/2000 | Klopotek |
| 6,120,452 A | 9/2000 | Barthe |
| 6,123,081 A | 9/2000 | Durette |
| 6,126,619 A | 10/2000 | Peterson et al. |
| 6,135,971 A | 10/2000 | Hutchinson |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Dias |
| 6,190,336 B1 | 2/2001 | Duarte |
| 6,193,658 B1 | 2/2001 | Wendelken |
| 6,198,956 B1 | 3/2001 | Dunne |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,074 B1 | 6/2001 | Averkiou et al. |
| 6,251,088 B1 | 6/2001 | Kaufman et al. |
| 6,268,405 B1 | 7/2001 | Yao |
| 6,273,864 B1 | 8/2001 | Duarte |
| 6,280,402 B1 | 8/2001 | Ishibashi et al. |
| 6,287,257 B1 | 9/2001 | Matichuk |
| 6,287,304 B1 | 9/2001 | Eggers et al. |
| 6,296,619 B1 | 10/2001 | Brisken |
| 6,301,989 B1 | 10/2001 | Brown et al. |
| 6,307,302 B1 | 10/2001 | Toda |
| 6,309,355 B1 | 10/2001 | Cain et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |
| 6,325,758 B1 | 12/2001 | Carol et al. |
| 6,325,769 B1 | 12/2001 | Klopotek |
| 6,325,798 B1 | 12/2001 | Edwards et al. |
| 6,350,276 B1 | 2/2002 | Knowlton |
| 6,356,780 B1 | 3/2002 | Licato et al. |
| 6,361,531 B1 | 3/2002 | Hissong |
| 6,370,411 B1 | 4/2002 | Osadchy et al. |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,216 B1 | 7/2002 | Cain et al. |
| 6,413,253 B1 | 7/2002 | Koop |
| 6,413,254 B1 | 7/2002 | Hissong |
| 6,419,648 B1 | 7/2002 | Vitek |
| 6,423,007 B2 | 7/2002 | Lizzi et al. |
| 6,425,865 B1 | 7/2002 | Salcudean |
| 6,425,867 B1 | 7/2002 | Vaezy |
| 6,425,912 B1 | 7/2002 | Knowlton |
| 6,428,477 B1 | 8/2002 | Mason |
| 6,428,532 B1 | 8/2002 | Doukas |
| 6,430,446 B1 | 8/2002 | Knowlton |
| 6,432,057 B1 | 8/2002 | Mazess et al. |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber |
| 6,443,914 B1 | 9/2002 | Costantino |
| 6,447,443 B1 | 9/2002 | Keogh et al. |
| 6,450,979 B1 | 9/2002 | Miwa et al. |
| 6,451,013 B1 | 9/2002 | Bays et al. |
| 6,453,202 B1 | 9/2002 | Knowlton |
| 6,461,304 B1 | 10/2002 | Tanaka et al. |
| 6,461,378 B1 | 10/2002 | Knowlton |
| 6,470,216 B1 | 10/2002 | Knowlton |
| 6,338,716 B1 | 11/2002 | Hossack et al. |
| 6,488,626 B1 | 12/2002 | Lizzi |
| 6,491,657 B2 | 12/2002 | Rowe |
| 6,500,121 B1 | 12/2002 | Slayton |
| 6,500,141 B1 | 12/2002 | Irion |
| 6,506,171 B1 | 1/2003 | Vitek et al. |
| 6,508,774 B1 | 1/2003 | Acker |
| 6,511,427 B1 | 1/2003 | Sliwa, Jr. et al. |
| 6,511,428 B1 | 1/2003 | Azuma |
| 6,514,244 B2 | 2/2003 | Pope |
| 6,517,484 B1 | 2/2003 | Wilk |
| 6,524,250 B1 | 2/2003 | Weber |
| 6,666,835 B2 | 3/2003 | Martin |
| 6,540,679 B2 | 4/2003 | Slayton |
| 6,540,685 B1 | 4/2003 | Rhoads et al. |
| 6,540,700 B1 | 4/2003 | Fujimoto et al. |
| 6,547,788 B1 | 4/2003 | Maguire et al. |
| 6,554,771 B1 | 4/2003 | Buil et al. |
| 6,569,099 B1 | 5/2003 | Babaev |
| 6,569,108 B2 | 5/2003 | Sarvazyan et al. |
| 6,572,552 B2 | 6/2003 | Fukukita |
| 6,575,956 B1 | 6/2003 | Brisken et al. |
| 6,595,934 B1 | 7/2003 | Hissong |
| 6,599,256 B1 | 7/2003 | Acker |
| 6,605,043 B1 | 8/2003 | Dreschel |
| 6,605,080 B1 | 8/2003 | Altshuler et al. |
| 6,607,498 B2 | 8/2003 | Eshel |
| 6,618,620 B1 | 9/2003 | Freundlich et al. |
| 6,623,430 B1 | 9/2003 | Slayton |
| 6,626,854 B2 | 9/2003 | Friedman |
| 6,626,855 B1 | 9/2003 | Weng |
| 6,638,226 B2 | 10/2003 | He et al. |
| 6,645,145 B1 | 11/2003 | Dreschel et al. |
| 6,645,150 B2 | 11/2003 | Angelsen et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,669,638 B1 | 12/2003 | Miller |
| 6,685,639 B1 | 2/2004 | Wang et al. |
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Laughlin |
| 6,719,694 B2 | 4/2004 | Weng |
| 6,726,627 B1 | 4/2004 | Lizzi et al. |

(56) References Cited

U.S. PATENT DOCUMENTS

| | | |
|---|---|---|
| 6,733,449 B1 | 5/2004 | Krishnamurthy et al. |
| 6,749,624 B2 | 6/2004 | Knowlton |
| 6,772,490 B2 | 8/2004 | Toda |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,825,176 B2 | 11/2004 | White et al. |
| 6,835,940 B2 | 12/2004 | Morikawa et al. |
| 6,846,290 B2 | 1/2005 | Lizzi et al. |
| 6,875,176 B2 | 4/2005 | Mourad et al. |
| 6,882,884 B1 | 4/2005 | Mosk et al. |
| 6,887,239 B2 | 5/2005 | Elstrom |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco |
| 7,303,555 B2 | 12/2007 | Makin et al. |
| 7,311,679 B2 | 12/2007 | Desilets et al. |
| 7,327,071 B2 | 2/2008 | Nishiyama et al. |
| 7,331,951 B2 | 2/2008 | Eshel et al. |
| 7,332,985 B2 | 2/2008 | Larson et al. |
| 7,338,434 B1 | 3/2008 | Haarstad et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,507,235 B2 | 3/2009 | Keogh et al. |
| 7,510,536 B2 | 3/2009 | Foley et al. |
| 7,517,315 B2 | 4/2009 | Willis |
| 7,530,356 B2 | 5/2009 | Slayton |
| 7,530,958 B2 | 5/2009 | Slayton |
| 7,532,201 B2 | 5/2009 | Quistgaard et al. |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,652,411 B2 | 1/2010 | Crunkilton et al. |
| 7,662,114 B2 | 2/2010 | Seip et al. |
| 7,674,257 B2 | 3/2010 | Pless et al. |
| 7,686,763 B2 | 3/2010 | Vaezy et al. |
| 7,713,203 B2 | 3/2010 | Lacoste et al. |
| 7,694,406 B2 | 4/2010 | Wildes et al. |
| 7,695,437 B2 | 4/2010 | Quistgaard et al. |
| 7,727,156 B2 | 6/2010 | Angelsen et al. |
| 7,758,524 B2 | 7/2010 | Barthe |
| 7,766,848 B2 | 8/2010 | Desilets et al. |
| 7,789,841 B2 | 9/2010 | Huckle et al. |
| 7,806,839 B2 | 10/2010 | Mast et al. |
| 7,815,570 B2 | 10/2010 | Eshel et al. |
| 7,819,826 B2 | 10/2010 | Diederich et al. |
| 7,828,734 B2 | 10/2010 | Azhari et al. |
| 7,824,348 B2 | 11/2010 | Barthe |
| 7,833,162 B2 | 11/2010 | Hasegawa et al. |
| 7,841,984 B2 | 11/2010 | Cribbs et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,901,359 B2 | 3/2011 | Mandrusov et al. |
| 7,905,007 B2 | 3/2011 | Calisti et al. |
| 7,905,844 B2 | 3/2011 | Desilets et al. |
| 7,914,453 B2 | 3/2011 | Slayton et al. |
| 7,914,469 B2 | 3/2011 | Torbati |
| 7,955,281 B2 | 6/2011 | Pedersen et al. |
| 7,967,764 B2 | 6/2011 | Lidgren et al. |
| 7,967,839 B2 | 6/2011 | Flock et al. |
| 7,955,262 B2 | 7/2011 | Rosenberg |
| 7,993,289 B2 | 8/2011 | Quistgaard et al. |
| 8,057,465 B2 | 9/2011 | Sliwa, Jr. et al. |
| 8,057,389 B2 | 11/2011 | Barthe et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,142,200 B2 | 3/2012 | Crunkilton et al. |
| 8,152,904 B2 | 4/2012 | Slobodzian et al. |
| 8,162,858 B2 | 4/2012 | Manna et al. |
| 8,166,332 B2 | 4/2012 | Barthe et al. |
| 8,182,428 B2 | 5/2012 | Angelsen et al. |
| 8,197,409 B2 | 6/2012 | Foley et al. |
| 8,206,299 B2 | 6/2012 | Foley et al. |
| 8,208,346 B2 | 6/2012 | Crunkilton |
| 8,211,017 B2 | 7/2012 | Foley et al. |
| 8,262,591 B2 | 9/2012 | Pedersen et al. |
| 8,262,650 B2 | 9/2012 | Zanelli et al. |
| 8,264,126 B2 | 9/2012 | Toda et al. |
| 8,273,037 B2 | 9/2012 | Kreindel et al. |
| 8,282,554 B2 | 10/2012 | Makin et al. |
| 8,292,835 B1 | 10/2012 | Cimino |
| 8,298,163 B1 | 10/2012 | Cimino |
| 8,333,700 B1 | 12/2012 | Barthe et al. |
| 8,334,637 B2 | 12/2012 | Crunkilton et al. |
| 8,337,407 B2 | 12/2012 | Quistgaard et al. |
| 8,343,051 B2 | 1/2013 | Desilets et al. |
| 8,454,540 B2 | 1/2013 | Eshel et al. |
| 8,366,622 B2 | 2/2013 | Slayton et al. |
| 8,398,549 B2 | 3/2013 | Palmeri et al. |
| 8,409,097 B2 | 4/2013 | Slayton et al. |
| 8,425,435 B2 | 4/2013 | Wing et al. |
| 8,388,535 B2 | 5/2013 | Weng et al. |
| 8,444,562 B2 | 5/2013 | Barthe et al. |
| 8,460,193 B2 | 6/2013 | Barthe et al. |
| 8,480,585 B2 | 7/2013 | Slayton et al. |
| 8,486,001 B2 | 7/2013 | Weyant |
| 8,506,486 B2 | 8/2013 | Slayton et al. |
| 8,512,250 B2 | 8/2013 | Quistgaard et al. |
| 8,523,775 B2 | 9/2013 | Barthe et al. |
| 8,523,849 B2 | 9/2013 | Liu et al. |
| 8,535,228 B2 | 9/2013 | Slayton et al. |
| 8,570,837 B2 | 10/2013 | Toda et al. |
| 8,573,392 B2 | 11/2013 | Bennett et al. |
| 8,583,211 B2 | 11/2013 | Salomir et al. |
| 8,585,618 B2 | 11/2013 | Hunziker et al. |
| 8,604,672 B2 | 12/2013 | Toda et al. |

(56) References Cited

U.S. PATENT DOCUMENTS

| | | |
|---|---|---|
| 8,622,937 B2 | 1/2014 | Weng et al. |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 8,728,071 B2 | 5/2014 | Lischinsky et al. |
| 8,753,295 B2 | 6/2014 | Thierman |
| 8,758,253 B2 | 6/2014 | Sano et al. |
| 8,836,203 B2 | 9/2014 | Nobles et al. |
| 8,857,438 B2 | 10/2014 | Barthe et al. |
| 8,858,471 B2 | 10/2014 | Barthe et al. |
| 8,915,853 B2 | 12/2014 | Barthe et al. |
| 8,915,854 B2 | 12/2014 | Slayton et al. |
| 8,915,870 B2 | 12/2014 | Barthe et al. |
| 8,920,320 B2 | 12/2014 | Stecco et al. |
| 8,920,324 B2 | 12/2014 | Slayton et al. |
| 8,926,533 B2 | 1/2015 | Bockenstedt et al. |
| 8,932,224 B2 | 1/2015 | Barthe et al. |
| 8,932,238 B2 | 1/2015 | Wing et al. |
| 8,968,205 B2 | 3/2015 | Zeng et al. |
| 9,011,336 B2 | 4/2015 | Slayton et al. |
| 9,039,617 B2 | 5/2015 | Slayton et al. |
| 9,039,619 B2 | 5/2015 | Barthe et al. |
| 9,050,116 B2 | 6/2015 | Homer |
| 9,095,697 B2 | 8/2015 | Barthe et al. |
| 9,107,798 B2 | 8/2015 | Azhari et al. |
| 9,114,247 B2 | 8/2015 | Barthe et al. |
| 9,180,314 B2 | 11/2015 | Desilets et al. |
| 9,216,276 B2 | 12/2015 | Slayton et al. |
| 9,220,915 B2 | 12/2015 | Liu et al. |
| 9,272,162 B2 | 3/2016 | Slayton et al. |
| 9,283,409 B2 | 3/2016 | Slayton et al. |
| 9,283,410 B2 | 3/2016 | Slayton et al. |
| 9,295,607 B2 | 3/2016 | Rosenberg |
| 9,308,390 B2 | 4/2016 | Youngquist |
| 9,308,391 B2 | 4/2016 | Liu et al. |
| 9,314,650 B2 | 4/2016 | Rosenberg et al. |
| 9,320,537 B2 | 4/2016 | Slayton et al. |
| 9,345,910 B2 | 5/2016 | Slayton et al. |
| 9,421,029 B2 | 8/2016 | Barthe et al. |
| 9,427,600 B2 | 8/2016 | Barthe et al. |
| 9,427,601 B2 | 8/2016 | Barthe et al. |
| 9,433,803 B2 | 9/2016 | Lin et al. |
| 9,440,093 B2 | 9/2016 | Homer |
| 9,440,096 B2 | 9/2016 | Barthe et al. |
| 9,492,645 B2 | 11/2016 | Zhou et al. |
| 9,492,686 B2 | 11/2016 | Da Silva |
| 9,498,651 B2 | 11/2016 | Sapozhnikov et al. |
| 9,510,802 B2 | 12/2016 | Barthe et al. |
| 9,522,290 B2 | 12/2016 | Slayton et al. |
| 9,532,832 B2 | 1/2017 | Ron Edoute et al. |
| 9,533,174 B2 | 1/2017 | Barthe et al. |
| 9,533,175 B2 | 1/2017 | Slayton et al. |
| 9,545,529 B2 | 1/2017 | Britva et al. |
| 9,566,454 B2 | 2/2017 | Barthe et al. |
| 9,623,267 B2 | 4/2017 | Ulric et al. |
| 9,694,211 B2 | 7/2017 | Barthe et al. |
| 9,694,212 B2 | 7/2017 | Barthe et al. |
| 9,700,340 B2 | 7/2017 | Barthe et al. |
| 9,707,412 B2 | 7/2017 | Slayton et al. |
| 9,710,607 B2 | 7/2017 | Ramdas et al. |
| 9,713,731 B2 | 7/2017 | Slayton et al. |
| 9,802,063 B2 | 10/2017 | Barthe et al. |
| 9,827,449 B2 | 11/2017 | Barthe et al. |
| 9,827,450 B2 | 11/2017 | Slayton et al. |
| 9,833,639 B2 | 12/2017 | Slayton et al. |
| 9,833,640 B2 | 12/2017 | Barthe et al. |
| 9,895,560 B2 | 2/2018 | Barthe et al. |
| 9,907,535 B2 | 3/2018 | Barthe et al. |
| 9,919,167 B2 | 3/2018 | Domankevitz |
| 9,974,982 B2 | 5/2018 | Slayton et al. |
| 1,001,072 A1 | 7/2018 | Slayton et al. |
| 1,004,618 A1 | 8/2018 | Barthe et al. |
| 1,023,889 A1 | 3/2019 | Slayton et al. |
| 1,024,545 A1 | 4/2019 | Slayton et al. |
| 1,025,208 A1 | 4/2019 | Barthe et al. |
| 1,026,555 A1 | 4/2019 | Barthe et al. |
| 1,032,828 A1 | 6/2019 | Barthe et al. |
| 2001/0009997 A1 | 7/2001 | Pope |
| 2001/0009999 A1 | 7/2001 | Kaufman et al. |
| 2001/0014780 A1 | 8/2001 | Martin |
| 2001/0014819 A1 | 8/2001 | Ingle |
| 2001/0031922 A1 | 10/2001 | Weng |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger |
| 2002/0062142 A1 | 5/2002 | Knowlton |
| 2002/0072691 A1 | 6/2002 | Thompson et al. |
| 2002/0082528 A1 | 6/2002 | Friedman |
| 2002/0082529 A1 | 6/2002 | Suorsa et al. |
| 2002/0082589 A1 | 6/2002 | Friedman |
| 2002/0087080 A1 | 7/2002 | Slayton |
| 2002/0095143 A1 | 7/2002 | Key |
| 2002/0099094 A1 | 7/2002 | Anderson |
| 2002/0111569 A1 | 8/2002 | Rosenschien et al. |
| 2002/0115917 A1 | 8/2002 | Honda et al. |
| 2002/0128639 A1 | 8/2002 | Pless et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | McHale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0018270 A1 | 1/2003 | Makin et al. |
| 2003/0023283 A1 | 1/2003 | McDaniel |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra |
| 2003/0055308 A1 | 3/2003 | Friemel et al. |
| 2003/0055417 A1 | 3/2003 | Truckai et al. |
| 2003/0060736 A1 | 3/2003 | Martin et al. |
| 2003/0065313 A1 | 4/2003 | Koop |
| 2003/0066708 A1 | 4/2003 | Allison et al. |
| 2003/0073907 A1 | 4/2003 | Taylor |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 | 7/2003 | Ustuner |
| 2003/0135135 A1 | 7/2003 | Miwa et al. |
| 2003/0139790 A1 | 7/2003 | Ingle et al. |
| 2003/0149366 A1 | 8/2003 | Stringer et al. |
| 2003/0153961 A1 | 8/2003 | Babaev |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0199794 A1 | 10/2003 | Sakurai et al. |
| 2003/0200481 A1 | 10/2003 | Stanley |
| 2003/0212129 A1 | 11/2003 | Liu et al. |
| 2003/0212351 A1 | 11/2003 | Hissong |

(56) References Cited

U.S. PATENT DOCUMENTS

| | | |
|---|---|---|
| 2003/0212393 A1 | 11/2003 | Knowlton |
| 2003/0216648 A1 | 11/2003 | Lizzi et al. |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002658 A1 | 1/2004 | Marian, Jr. |
| 2004/0002705 A1 | 1/2004 | Knowlton |
| 2004/0010222 A1 | 1/2004 | Nunomura et al. |
| 2004/0015079 A1 | 1/2004 | Berger et al. |
| 2004/0015106 A1 | 1/2004 | Coleman |
| 2004/0030227 A1 | 2/2004 | Littrup |
| 2004/0030268 A1 | 2/2004 | Weng et al. |
| 2004/0039312 A1 | 2/2004 | Hillstead |
| 2004/0039418 A1 | 2/2004 | Elstrom |
| 2004/0041563 A1 | 3/2004 | Lewin et al. |
| 2004/0041880 A1 | 3/2004 | Ikeda et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0049734 A1 | 3/2004 | Tosaya et al. |
| 2004/0059266 A1 | 3/2004 | Fry |
| 2004/0068186 A1 | 4/2004 | Ishida et al. |
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger |
| 2004/0082859 A1 | 4/2004 | Schaer |
| 2004/0102697 A1 | 5/2004 | Evron |
| 2004/0105559 A1 | 6/2004 | Aylward et al. |
| 2004/0106867 A1 | 6/2004 | Eshel et al. |
| 2004/0122323 A1 | 6/2004 | Vortman et al. |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste |
| 2004/0267252 A1 | 12/2004 | Washington et al. |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055018 A1 | 3/2005 | Kreindel |
| 2005/0055073 A1 | 3/2005 | Weber |
| 2005/0061834 A1 | 3/2005 | Garcia et al. |
| 2005/0070961 A1 | 3/2005 | Maki |
| 2005/0074407 A1 | 4/2005 | Smith |
| 2005/0080469 A1 | 4/2005 | Larson |
| 2005/0085731 A1 | 4/2005 | Miller et al. |
| 2005/0091770 A1 | 5/2005 | Mourad et al. |
| 2005/0096542 A1 | 5/2005 | Weng et al. |
| 2005/0104690 A1 | 5/2005 | Larson et al. |
| 2005/0113689 A1 | 5/2005 | Gritzky |
| 2005/0131302 A1 | 6/2005 | Poland |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard |
| 2005/0193820 A1 | 9/2005 | Sheljaskow et al. |
| 2005/0197681 A1 | 9/2005 | Barolet et al. |
| 2005/0228281 A1 | 10/2005 | Nefos |
| 2005/0240127 A1 | 10/2005 | Seip et al. |
| 2005/0240170 A1 | 10/2005 | Zhang et al. |
| 2005/0251120 A1 | 11/2005 | Anderson et al. |
| 2005/0251125 A1 | 11/2005 | Pless et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0224090 A1 | 10/2006 | Ostrovsky et al. |
| 2006/0229514 A1 | 10/2006 | Wiener |
| 2006/0241440 A1 | 10/2006 | Eshel |
| 2006/0241442 A1 | 10/2006 | Barthe |
| 2006/0241470 A1 | 10/2006 | Novak et al. |
| 2006/0241576 A1 | 10/2006 | Diederich et al. |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0016039 A1 | 1/2007 | Vortman et al. |
| 2007/0032784 A1 | 2/2007 | Gliklich et al. |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets et al. |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0219604 A1 | 9/2007 | Yaroslavsky et al. |
| 2007/0219605 A1 | 9/2007 | Yaroslavsky et al. |
| 2007/0238994 A1 | 10/2007 | Stecco et al. |
| 2007/0239075 A1 | 10/2007 | Rosenberg |
| 2007/0239077 A1 | 10/2007 | Azhari et al. |
| 2007/0239079 A1 | 10/2007 | Manstein et al. |
| 2007/0239142 A1 | 10/2007 | Altshuler |
| 2008/0015435 A1 | 1/2008 | Cribbs et al. |
| 2008/0027328 A1 | 1/2008 | Klopotek |
| 2008/0033458 A1 | 2/2008 | McLean et al. |
| 2008/0039724 A1 | 2/2008 | Seip et al. |
| 2008/0071255 A1 | 3/2008 | Barthe |
| 2008/0086054 A1 | 4/2008 | Slayton |
| 2008/0086056 A1 | 4/2008 | Chang et al. |
| 2008/0097214 A1 | 4/2008 | Meyers et al. |

(56) References Cited

U.S. PATENT DOCUMENTS

| | | |
|---|---|---|
| 2008/0097253 A1 | 4/2008 | Pedersen et al. |
| 2008/0114251 A1 | 5/2008 | Weymer et al. |
| 2008/0139943 A1 | 6/2008 | Deng et al. |
| 2008/0139974 A1 | 6/2008 | Da Silva |
| 2008/0146970 A1 | 6/2008 | Litman et al. |
| 2008/0167556 A1 | 7/2008 | Thompson |
| 2008/0183077 A1 | 7/2008 | Moreau-Gobard et al. |
| 2008/0183110 A1 | 7/2008 | Davenport et al. |
| 2008/0188745 A1 | 8/2008 | Chen et al. |
| 2008/0194964 A1 | 8/2008 | Randall et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0214988 A1 | 9/2008 | Altshuler et al. |
| 2008/0221491 A1 | 9/2008 | Slayton |
| 2008/0223379 A1 | 9/2008 | Stuker et al. |
| 2008/0242991 A1 | 10/2008 | Moon et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294073 A1 | 11/2008 | Barthe |
| 2008/0319356 A1 | 12/2008 | Cain |
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0048514 A1 | 2/2009 | Azhari et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0163807 A1 | 6/2009 | Sliwa |
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0198157 A1 | 8/2009 | Babaev et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0230823 A1* | 9/2009 | Kushculey ............... A61N 7/02 310/366 |
| 2009/0253988 A1 | 10/2009 | Slayton et al. |
| 2009/0281463 A1 | 11/2009 | Chapelon et al. |
| 2009/0312693 A1 | 12/2009 | Thapliyal et al. |
| 2009/0318909 A1 | 12/2009 | Debenedictis et al. |
| 2009/0326420 A1 | 12/2009 | Moonen et al. |
| 2010/0011236 A1 | 1/2010 | Barthe et al. |
| 2010/0022919 A1 | 1/2010 | Peterson |
| 2010/0022921 A1 | 1/2010 | Seip et al. |
| 2010/0022922 A1 | 1/2010 | Barthe et al. |
| 2010/0030076 A1 | 2/2010 | Vortman et al. |
| 2010/0042020 A1 | 2/2010 | Ben-Ezra |
| 2010/0049178 A1 | 2/2010 | Deem et al. |
| 2010/0056925 A1 | 3/2010 | Zhang et al. |
| 2010/0100014 A1 | 4/2010 | Eshel et al. |
| 2010/0113983 A1 | 5/2010 | Heckerman et al. |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241035 A1 | 9/2010 | Barthe et al. |
| 2010/0249602 A1 | 9/2010 | Buckley et al. |
| 2010/0249669 A1 | 9/2010 | Ulric et al. |
| 2010/0256489 A1 | 10/2010 | Pedersen et al. |
| 2010/0274161 A1 | 10/2010 | Azhari et al. |
| 2010/0280420 A1 | 11/2010 | Barthe et al. |
| 2010/0286518 A1 | 11/2010 | Lee et al. |
| 2010/0312150 A1 | 12/2010 | Douglas et al. |
| 2011/0040171 A1 | 2/2011 | Foley et al. |
| 2011/0040190 A1 | 2/2011 | Jahnke et al. |
| 2011/0040213 A1 | 2/2011 | Dietz et al. |
| 2011/0040214 A1 | 2/2011 | Foley et al. |
| 2011/0066084 A1 | 3/2011 | Desilets et al. |
| 2011/0072970 A1 | 3/2011 | Slobodzian et al. |
| 2011/0077514 A1 | 3/2011 | Ulric et al. |
| 2011/0087099 A1 | 4/2011 | Eshel et al. |
| 2011/0087255 A1 | 4/2011 | McCormack et al. |
| 2011/0112405 A1 | 5/2011 | Barthe et al. |
| 2011/0144490 A1 | 6/2011 | Davis et al. |
| 2011/0178444 A1 | 7/2011 | Slayton et al. |
| 2011/0178541 A1 | 7/2011 | Azhari |
| 2011/0190745 A1 | 8/2011 | Uebelhoer et al. |
| 2011/0201976 A1 | 8/2011 | Sanghvi et al. |
| 2011/0251524 A1 | 10/2011 | Azhari et al. |
| 2011/0251527 A1 | 10/2011 | Kushculey et al. |
| 2011/0270137 A1 | 11/2011 | Goren et al. |
| 2011/0319793 A1 | 12/2011 | Henrik et al. |
| 2011/0319794 A1 | 12/2011 | Gertner |
| 2012/0004549 A1 | 1/2012 | Barthe et al. |
| 2012/0016239 A1 | 1/2012 | Barthe et al. |
| 2012/0029353 A1 | 2/2012 | Slayton et al. |
| 2012/0035473 A1 | 2/2012 | Sanghvi et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0059288 A1 | 3/2012 | Barthe et al. |
| 2012/0111339 A1 | 5/2012 | Barthe et al. |
| 2012/0123304 A1 | 5/2012 | Rybyanets et al. |
| 2012/0136280 A1 | 5/2012 | Rosenberg et al. |
| 2012/0136282 A1 | 5/2012 | Rosenberg et al. |
| 2012/0143056 A1 | 6/2012 | Slayton et al. |
| 2012/0143100 A1 | 6/2012 | Jeong et al. |
| 2012/0165668 A1 | 6/2012 | Slayton et al. |
| 2012/0165848 A1 | 6/2012 | Slayton et al. |
| 2012/0191019 A1 | 7/2012 | Desilets et al. |
| 2012/0191020 A1 | 7/2012 | Vitek et al. |
| 2012/0197120 A1 | 8/2012 | Makin et al. |
| 2012/0197121 A1 | 8/2012 | Slayton et al. |
| 2012/0209150 A1 | 8/2012 | Zeng et al. |
| 2012/0215105 A1 | 8/2012 | Slayton et al. |
| 2012/0271202 A1 | 10/2012 | Wisdom |
| 2012/0271294 A1 | 10/2012 | Barthe et al. |
| 2012/0277639 A1 | 11/2012 | Pollock et al. |
| 2012/0296240 A1 | 11/2012 | Azhari et al. |
| 2012/0302883 A1 | 11/2012 | Kong et al. |
| 2012/0316426 A1 | 12/2012 | Foley et al. |
| 2012/0330197 A1 | 12/2012 | Makin et al. |
| 2012/0330222 A1 | 12/2012 | Makin et al. |
| 2012/0330223 A1 | 12/2012 | Makin et al. |
| 2012/0330283 A1 | 12/2012 | Hyde et al. |
| 2012/0330284 A1 | 12/2012 | Hyde et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018285 A1 | 1/2013 | Park et al. |
| 2013/0018286 A1 | 1/2013 | Slayton et al. |
| 2013/0046209 A1 | 2/2013 | Slayton et al. |
| 2013/0051178 A1 | 2/2013 | Rybyanets |
| 2013/0060170 A1 | 3/2013 | Lee et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0073001 A1 | 3/2013 | Campbell |
| 2013/0096471 A1 | 4/2013 | Slayton et al. |
| 2013/0190659 A1 | 7/2013 | Slayton et al. |
| 2013/0211293 A1 | 8/2013 | Auboiroux et al. |
| 2013/0225994 A1 | 8/2013 | Hsu et al. |
| 2013/0268032 A1 | 10/2013 | Neev |
| 2013/0274603 A1 | 10/2013 | Barthe et al. |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0296743 A1 | 11/2013 | Lee et al. |
| 2013/0303904 A1 | 11/2013 | Barthe et al. |
| 2013/0303905 A1 | 11/2013 | Barthe et al. |

(56) References Cited

U.S. PATENT DOCUMENTS

| | | |
|---|---|---|
| 2013/0310714 A1 | 11/2013 | Eshel et al. |
| 2013/0310863 A1 | 11/2013 | Makin et al. |
| 2013/0345562 A1 | 12/2013 | Barthe et al. |
| 2014/0024974 A1 | 1/2014 | Slayton et al. |
| 2014/0050054 A1 | 2/2014 | Toda et al. |
| 2014/0081300 A1 | 3/2014 | Melodelima et al. |
| 2014/0082907 A1 | 3/2014 | Barthe et al. |
| 2014/0117814 A1 | 5/2014 | Toda et al. |
| 2014/0142430 A1 | 5/2014 | Slayton et al. |
| 2014/0148834 A1 | 5/2014 | Barthe et al. |
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |
| 2014/0194723 A1 | 7/2014 | Herzog et al. |
| 2014/0208856 A1 | 7/2014 | Schmid |
| 2014/0221823 A1 | 8/2014 | Keogh et al. |
| 2014/0236049 A1 | 8/2014 | Barthe et al. |
| 2014/0236061 A1 | 8/2014 | Lee et al. |
| 2014/0243713 A1 | 8/2014 | Slayton et al. |
| 2014/0257145 A1 | 9/2014 | Emery |
| 2014/0276055 A1 | 9/2014 | Barthe et al. |
| 2015/0000674 A1 | 1/2015 | Barthe et al. |
| 2015/0025420 A1 | 1/2015 | Slayton et al. |
| 2015/0080723 A1 | 3/2015 | Barthe et al. |
| 2015/0080771 A1 | 3/2015 | Barthe et al. |
| 2015/0080874 A1 | 3/2015 | Slayton et al. |
| 2015/0088182 A1 | 3/2015 | Slayton et al. |
| 2015/0141734 A1 | 5/2015 | Chapelon et al. |
| 2015/0164734 A1 | 6/2015 | Slayton et al. |
| 2015/0165238 A1 | 6/2015 | Slayton et al. |
| 2015/0165243 A1 | 6/2015 | Slayton et al. |
| 2015/0174388 A1 | 6/2015 | Slayton |
| 2015/0202468 A1 | 7/2015 | Slayton et al. |
| 2015/0217141 A1 | 8/2015 | Barthe et al. |
| 2015/0238258 A1 | 8/2015 | Palero et al. |
| 2015/0321026 A1 | 11/2015 | Branson et al. |
| 2015/0360058 A1 | 12/2015 | Barthe et al. |
| 2015/0374333 A1 | 12/2015 | Barthe et al. |
| 2015/0375014 A1 | 12/2015 | Slayton et al. |
| 2016/0001097 A1* | 1/2016 | Cho .................. A61N 7/02 601/3 |
| 2016/0016015 A1 | 1/2016 | Slayton et al. |
| 2016/0027994 A1 | 1/2016 | Toda et al. |
| 2016/0151618 A1 | 6/2016 | Powers et al. |
| 2016/0175619 A1 | 6/2016 | Lee et al. |
| 2016/0206335 A1 | 7/2016 | Slayton |
| 2016/0206341 A1 | 7/2016 | Slayton |
| 2016/0256675 A1 | 9/2016 | Slayton |
| 2016/0296769 A1 | 10/2016 | Barthe et al. |
| 2016/0361571 A1 | 12/2016 | Bernabei |
| 2016/0361572 A1 | 12/2016 | Slayton |
| 2017/0028227 A1 | 2/2017 | Emery et al. |
| 2017/0043190 A1 | 2/2017 | Barthe et al. |
| 2017/0050019 A1 | 2/2017 | Ron Edoute et al. |
| 2017/0080257 A1 | 3/2017 | Paunescu et al. |
| 2017/0100585 A1 | 4/2017 | Hall et al. |
| 2017/0136263 A1 | 5/2017 | Reil |
| 2017/0209201 A1 | 7/2017 | Slayton et al. |
| 2017/0304654 A1 | 10/2017 | Blanche et al. |
| 2018/0001113 A1 | 1/2018 | Streeter |
| 2018/0015308 A1 | 1/2018 | Reed et al. |
| 2018/0043147 A1 | 2/2018 | Slayton |
| 2018/0099162 A1 | 4/2018 | Bernabei |
| 2018/0099163 A1 | 4/2018 | Bernabei |
| 2018/0272156 A1 | 9/2018 | Slayton et al. |
| 2018/0272157 A1 | 9/2018 | Barthe et al. |
| 2018/0272158 A1 | 9/2018 | Barthe et al. |
| 2018/0272159 A1 | 9/2018 | Slayton et al. |

FOREIGN PATENT DOCUMENTS

| | | |
|---|---|---|
| DE | 4029175 | 3/1992 |
| DE | 10140064 | 3/2003 |
| DE | 10219297 | 11/2003 |
| DE | 10219217 | 12/2004 |
| DE | 20314479 | 12/2004 |
| EP | 0142215 | 5/1984 |
| EP | 0344773 | 12/1989 |
| EP | 1479412 | 11/1991 |
| EP | 0473553 | 4/1992 |
| EP | 670147 | 2/1995 |
| EP | 0661029 | 7/1995 |
| EP | 724894 | 2/1996 |
| EP | 763371 | 11/1996 |
| EP | 1044038 | 10/2000 |
| EP | 1050322 | 11/2000 |
| EP | 1234566 | 8/2002 |
| EP | 1262160 | 12/2002 |
| EP | 0659387 | 4/2003 |
| EP | 1374944 | 1/2004 |
| EP | 1028660 | 1/2008 |
| EP | 1874241 | 1/2008 |
| EP | 1362223 | 5/2008 |
| EP | 1750804 | 7/2008 |
| EP | 1283690 | 11/2008 |
| EP | 1811901 | 4/2009 |
| EP | 1785164 | 8/2009 |
| EP | 2230904 | 9/2010 |
| EP | 1501331 | 6/2011 |
| EP | 2066405 | 11/2011 |
| EP | 2474050 | 7/2012 |
| EP | 2709726 | 11/2015 |
| EP | 1538980 | 1/2017 |
| EP | 2897547 | 11/2017 |
| FR | 2532851 | 9/1983 |
| FR | 2685872 | 1/1992 |
| FR | 2672486 | 8/1992 |
| FR | 2703254 | 3/1994 |
| GB | 2113099 | 8/1983 |
| IL | 102516 | 1/1996 |
| IL | 112369 | 8/1999 |
| IL | 120079 | 3/2001 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 04150847 | 5/1992 |
| JP | 7080087 | 3/1995 |
| JP | 07505793 | 6/1995 |
| JP | 7184907 | 7/1995 |
| JP | 7222782 | 8/1995 |
| JP | 09047458 | 2/1997 |
| JP | 9108288 | 4/1997 |
| JP | 9503926 | 4/1997 |
| JP | 11123226 | 5/1999 |
| JP | 11505440 | 5/1999 |
| JP | 11506636 | 6/1999 |
| JP | 10248850 | 9/1999 |
| JP | 2000126310 | 5/2000 |
| JP | 2000166940 | 6/2000 |
| JP | 2000233009 | 8/2000 |
| JP | 2001-46387 | 2/2001 |
| JP | 2001170068 | 6/2001 |
| JP | 2002505596 | 2/2002 |
| JP | 2002078764 | 3/2002 |
| JP | 2002515786 | 5/2002 |
| JP | 2002537013 | 5/2002 |
| JP | 2002521118 | 7/2002 |
| JP | 2002537939 | 11/2002 |
| JP | 2003050298 | 7/2003 |
| JP | 2003204982 | 7/2003 |
| JP | 2004-504898 | 2/2004 |
| JP | 2004-507280 | 3/2004 |
| JP | 2004154256 | 3/2004 |
| JP | 2004-509671 | 4/2004 |
| JP | 2004-512856 | 4/2004 |
| JP | 2004147719 | 5/2004 |
| JP | 2005503388 | 2/2005 |
| JP | 2005527336 | 9/2005 |
| JP | 2005323213 | 11/2005 |
| JP | 2006520247 | 9/2006 |

(56) References Cited

FOREIGN PATENT DOCUMENTS

| | | |
|---|---|---|
| JP | 2008515559 | 5/2008 |
| JP | 2009518126 | 5/2009 |
| JP | 2010517695 | 5/2010 |
| KR | 1020010024871 | 3/2001 |
| KR | 100400870 | 10/2003 |
| KR | 20060121267 | 11/2006 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| KR | 1020000059516 | 4/2012 |
| KR | 10-2013-0124598 | 11/2013 |
| KR | 10-1365946 | 2/2014 |
| TW | 386883 | 9/2000 |
| TW | 201208734 A | 3/2012 |
| WO | WO9312742 | 7/1993 |
| WO | WO9524159 | 9/1995 |
| WO | WO9625888 | 8/1996 |
| WO | WO9634568 | 11/1996 |
| WO | WO9639079 | 12/1996 |
| WO | WO9735518 | 10/1997 |
| WO | WO9832379 | 7/1998 |
| WO | WO9852465 | 11/1998 |
| WO | WO9933520 | 7/1999 |
| WO | WO9939677 | 8/1999 |
| WO | WO9949788 | 10/1999 |
| WO | WO200006032 | 2/2000 |
| WO | WO0015300 | 3/2000 |
| WO | WO0021612 | 4/2000 |
| WO | WO0048518 | 8/2000 |
| WO | WO0053113 | 9/2000 |
| WO | WO0128623 | 4/2001 |
| WO | WO01045550 | 6/2001 |
| WO | WO0182777 | 11/2001 |
| WO | WO0182778 | 11/2001 |
| WO | WO0187161 | 11/2001 |
| WO | WO01080709 | 11/2001 |
| WO | WO2001087161 | 11/2001 |
| WO | WO0209812 | 2/2002 |
| WO | WO0209813 | 2/2002 |
| WO | WO02015768 | 2/2002 |
| WO | WO0224050 | 3/2002 |
| WO | WO2002054018 | 7/2002 |
| WO | WO02092168 | 11/2002 |
| WO | WO03053266 | 7/2003 |
| WO | WO03065347 | 8/2003 |
| WO | WO03070105 | 8/2003 |
| WO | WO03077833 | 9/2003 |
| WO | WO03086215 | 10/2003 |
| WO | WO03096883 | 11/2003 |
| WO | WO03099177 | 12/2003 |
| WO | WO03099382 | 12/2003 |
| WO | WO03101530 | 12/2003 |
| WO | WO2004000116 | 12/2003 |
| WO | WO2004080147 | 9/2004 |
| WO | WO2004110558 | 12/2004 |
| WO | WO2005/011804 | 2/2005 |
| WO | WO2005065408 | 7/2005 |
| WO | WO2005065409 | 7/2005 |
| WO | WO2005090978 | 9/2005 |
| WO | WO2005113068 | 12/2005 |
| WO | WO2006/042163 | 4/2006 |
| WO | WO2006036870 | 4/2006 |
| WO | WO2006042168 | 4/2006 |
| WO | WO2006042201 | 4/2006 |
| WO | WO2006065671 | 6/2006 |
| WO | WO2006082573 | 8/2006 |
| WO | WO2006104568 | 10/2006 |
| WO | WO2007067563 | 6/2007 |
| WO | WO2008036479 | 3/2008 |
| WO | WO2008036622 | 3/2008 |
| WO | WO2008144274 | 11/2008 |
| WO | WO2009013729 | 1/2009 |
| WO | WO2009149390 | 10/2009 |
| WO | WO2012134645 | 10/2012 |
| WO | WO2013048912 | 4/2013 |
| WO | WO2013178830 | 12/2013 |
| WO | WO2014045216 | 3/2014 |
| WO | WO2014055708 | 4/2014 |
| WO | WO2014057388 | 4/2014 |
| WO | WO2014127091 | 8/2014 |
| WO | WO2015160708 | 10/2015 |
| WO | WO2016054155 | 4/2016 |
| WO | WO2017127328 | 7/2017 |
| WO | WO2017149506 | 9/2017 |
| WO | WO2017165595 | 9/2017 |
| WO | WO2017212489 | 12/2017 |
| WO | WO2018035012 | 2/2018 |
| WO | WO 2019147596 | 8/2019 |

OTHER PUBLICATIONS

Agren, Magnus S. et al., Collagenase in Wound Healing: Effect of Wound Age and Type. The Journal of Investigative Dermatology, vol. 99 No. 6, (Dec. 1992).

Alam, M., "The future of noninvasive procedural dermatology". Semin Cutan Med Surg. Mar. 2013; 32(1):59-61.

Alam, M., et al., "Ultrasound tightening of facial and neck skin: a rater-blinded prospective cohort study". J Am Acad Dermatol, 2010. 62(2): p. 262-9.

Alexiades-Armenakas, M., "Ultrasound Technologies for Dermatologic Techniques". J Drugs Derm. 2014. 12 (11): p. 1305.

Alster, T.S., et. al., "Noninvasive lifting of arm, thigh, and knee skin with transcutaneousintense focused ultrasound". Dermatol Surg, 2012. 38(5): p. 754-9.

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Arosarena, O., "Options and Challenges for Facial Rejuvenation in Patients With Higher Fitzpatrick Skin Phototypes". JAMA Facial Plastic Surgery, 2015.

Arthur et al., "Non-invasive estimation of hyperthermia temperatures with ultrasound," Int. J. Hyperthermia, Sep. 2005, 21(6), pp. 589-600.

Barthe et al., "Ultrasound therapy system and ablation results utilizing miniature imaging/therapy arrays," Ultrasonics Symposium, 2004 IEEE, Aug. 23, 2004, pp. 1792-1795, vol. 3.

Bozec, Laurent et al., Thermal Denaturation Studies of Collagen by Microthermal Analysis and Atomic Force Microscopy, Biophysical Journal, vol. 101, pp. 228-236. (Jul. 2001).

Brobst, R.W., et. al., "Noninvasive Treatment of the Neck". Facial Plast Surg Clin North Am, 2014. 22(2): p. 191-202.

Brobst, R.W., et., al., "Ulthera: initial and six month results". Facial Plast Surg Clin North Am, 2012. 20(2): p. 163-76.

Calderhead et al., "One Mechanism Behind LED Photo-Therapy for Wound Healing and Skin Rejuvenation: Key Role of the Mast Cell" Laser Therapy 17.3: 141-148 (2008).

Casabona, G., et. al., "Microfocused Ultrasound With Visualization and Fillers for Increased Neocollagenesis: Clinical and Histological Evaluation". Dermatol Surg 2014;40:S194-S198.

Chan, N.P., et al., "Safety study of transcutaneous focused ultrasound for non-invasive skin tightening in Asians". Lasers Surg Med, 2011. 43(5): p. 366-75.

Chapelon et al., "Effects of Cavitation in the High Intensity Therapeutic Ultrasound", Ultrasonics Symposium—1357 (1991).

Chapelon, et al., "Thresholds for Tissue Ablation by Focused Ultrasound" (1990).

Chen, L. et al., "Effect of Blood Perfusion on the ablation of liver parenchyma with high intensity focused ultrasound," Phys. Med. Biol; 38:1661-1673; 1993b.

Coon, Joshua et al., "Protein identification using sequential ion/ion reactions and tandem mass spectrometry" Proceedings of the National Academy of Sciences of the USA, vol. 102, No. 27, Jul. 27, 2005, pp. 9463-9468.

(56) References Cited

OTHER PUBLICATIONS

Corry, Peter M., et al., "Human Cancer Treatment with Ultrasound", IEEE Transactions on Sonics and Ultrasonics, vol. SU-31, No. 5, Sep. 1984, pp. 444, 456.
Damianou et al., "Application of the Thermal Dose Concept for Predicting the Necrosed Tissue Volume During Ultrasound Surgery," 1993 IEEE Ultrasound Symposium, pp. 1199-1202.
Daum et al., Design and Evaluation of a Feedback Based Phased Array System for Ultrasound Surgery, IEEE Transactions on Ultrasonics, Ferroelectrics, and Frequency Control, vol. 45, No. 2, Mar. 1998, pp. 431-438.
Davis, Brian J., et al., "An Acoustic Phase Shift Technique for the Non-Invasive Measurement of Temperature Changes in Tissues", 1985 Ultrasonics Symposium, pp. 921-924.
Dayan, S.H., et al., "Prospective, Multi-Center, Pivotal Trial Evaluating the Safety and Effectiveness of Micro-Focused Ultrasound with Visualization (MFU-V) for Improvement in Lines and Wrinkles of the Décolletage". Plast Reconstr Surg. Oct. 2014; 134(4 Suppl 1):123-4.
Decision of the Korean Intellectual Property Tribunal dated Jun. 28, 2013 regarding Korean Patent No. 10-1142108, which is related to the pending applicaiton and/or an application identified in the Table on pp. 1-4 of the Information Disclosure Statement herein (English translation, English translation certification, and Korean decision included).
Delon Martin, C., et al, "Venous Thrombosis Generation by Means of High-Intensity Focused Ultrasound" Ultrasound in Med. & Biol., vol. 21, No. 1, pp. 113-119 (1995).
Dierickx, Christine C., "The Role of Deep Heating for Noninvasive Skin Rejuvenation" Lasers in Surgery and Medicine 38:799-807 (2006).
Dobke, M.K., et al., "Tissue restructuring by energy-based surgical tools". Clin Plast Surg, 2012. 39(4): p. 399-408.
Dong, Yuan-Lin et al., "Effect of Ibuprofen on the Inflammatory Response to Surgical Wounds" The Journal of Trauma, vol. 35, No. 3. (1993).
Dvivedi, Sanjay, et al. "Effect of Ibuprofen and diclofenac sodium on experimental wound healing" Indian Journal of Experimental Biology, vol. 35, pp. 1243-1245. (Nov. 1997).
Fabi, S.G., "Microfocused Ultrasound With Visualization for Skin Tightening and Lifting: My Experience and a Review of the Literature". Dermatol Surg. Dec. 2014; 40 Suppl 12:S164-7.
Fabi, S.G., "Noninvasive skin tightening: focus on new ultrasound techniques". Clin Cosmet Investig Dermatol. Feb. 5, 2015; 8:47-52.
Fabi, S.G., et. al., "A prospective multicenter pilot study of the safety and efficacy of microfocused ultrasound with visualization for improving lines and wrinkles of the décolleté". Dermatol Surg. Mar. 2015; 41(3):327-35.
Fabi, S.G., et. al., "Evaluation of microfocused ultrasound with visualization for lifting, tightening, and wrinkle reduction of the decolletage". J Am Acad Dermatol, 2013. 69(6): p. 965-71.
Fabi, S.G., et. al., "Future directions in cutaneous laser surgery". Dermatol Clin, 2014. 32(1): p. 61-9.
Fabi, S.G., et. al., "Retrospective Evaluation of Micro-focused Ultrasound for Lifting and Tightening the Face and Neck". Dermatol Surg, 2014.
Friedmann D.P., "Comments on evaluation of microfocused ultrasound system for improving skin laxity and tightening in the lower face". Aesthet Surg J. Mar. 2015;35(3):NP81-2.
Friedmann, D.P., et. al., "Combination of intense pulsed light, Sculptra, and Ultherapy for treatment of the aging face". J Cosmet Dermatol, 2014. 13(2): p. 109-18.
Fry W.J. et al., "Production of Focal Destructive Lesions in the Central Nervous System with Ultrasound," J. Neurosurg., 11:471-478; 1954.
Fujimoto, et al., "A New Cavitation Suppression Technique for Local Ablation Using High-Intensity Focused Ultrasound" Ultrasonics Symposium—1629 (1995).
Gliklich et al., Clinical Pilot Study of Intense Ultrasound therapy to Deep Dermal Facial Skin and Subcutaneous Tissues, Arch Facial Plastic Surgery, Mar. 1, 2007, vol. 9, No. 1.
Gold, M.H., et. al., "Use of Micro-Focused Ultrasound with Visualization to Lift and Tighten Lax Knee Skin". J Cosmet Laser Ther, 2014: p. 1-15.
Goldberg, D.J., et. al., "Safety and Efficacy of Microfocused Ultrasound to Lift, Tighten, and Smooth the Buttocks". Dermatol Surg 2014; 40:1113-1117.
Greene, R.M., et al., "Skin tightening technologies". Facial Plast Surg. Feb. 2014; 30(1):62-7.
Greenhalgh, David G., "Wound healing and diabetes mellitus" Clinics in Plastic Surgery 30; 37-45. (2003).
Guo, S. et al., "Factors Affecting Wound Healing" Critical Reviews in Oral Biology & Medicine, J Dent Res 89(3), pp. 219-229. (2010).
Haar, G.R. et al., "Tissue Destruction with Focused Ultrasound in Vivo," Eur. Urol. 23 (suppl. 1):8-11; 1993.
Hantash, Basil M. et al., "Bipolar Fractional Radiofrequency Treatment Induces Neoelastogenesis and Neocollagenesis" Lasers in Surgery and Medicine 41:1-9 (2009).
Hantash, Basil M. et al., "In Vivo Histological Evaluation of a Novel Ablative Fractional Resurfacing Device" Lasers in Surgery and Medicine 39:96-107 (2007).
Harris, M.O., "Safety of Microfocused Ultrasound With Visualization in Patients With Fitzpatrick Skin Phototypes III to VI". JAMA Facial Plast. Surg, 2015.
Hart, et. al., "Current Concepts in the Use of PLLA:Clinical Synergy Noted with Combined Use of Microfocused Ultrasound and Poly-I-Lactic Acid on the Face, Neck, and Décolletage". Amer. Soc. Plast. Surg. 2015. 136; 180-187S.
Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.
Hassan et al., "Structure and Morphology of Freeze/Thawed PVA Hydrogels," Macromolecules, Mar. 11, 2000, pp. 2472-2479, vol. 33, No. 7.
Hitchcock, T.M. et. al., "Review of the safety profile for microfocused ultrasound with Visualization". Journal of Cosmetic Dermatology, 13, 329-335. (2014).
Husseini et al, "The Role of Cavitation in Acoustically Activated Drug Delivery," J. Control Release, Oct. 3, 2005, pp. 253-261, vol. 107(2).
Husseini et al. "Investigating the mechanism of acoustically activated uptake of drugs from Pluronic micelles," BMD Cancer 2002, 2:20k, Aug. 30, 2002, pp. 1-6.
Hynynen et al., Temperature Distributions During Local Ultrasound Induced Hyperthermia In Vivo, Ultrasonics Symposium—745 (1982).
Jeffers et al., "Evaluation of the Effect of Cavitation Activity on Drug-Ultrasound Synergisms," 1993 IEEE Ultrasonics Symposium, pp. 925-928.
Jenne, J., et al., "Temperature Mapping for High Energy US-Therapy", 1994 Ultrasonics Symposium, pp. 1879-1882.
Jeong, K.H., et al., "Neurologic complication associated with intense focused ultrasound". J Cosmet Laser Ther, 2013.
Johnson, S.A., et al., "Non-Intrusive Measurement of Microwave and Ultrasound-Induced Hyperthermia by Acoustic Temperature Tomography", Ultrasonics Symposium Proceedings, pp. 977-982. (1977).
Kim, H.J., et al., "Coagulation and ablation patterns of high-intensity focused ultrasound on a tissue mimicking phantom and cadaveric skin". Laser Med Sci. Sep. 4, 2015.
Kornstein, A.N., "Ulthera for silicone lip correction". Plast Reconstr Surg, 2012. 129(6): p. 1014e-1015e.
Kornstein, A.N., "Ultherapy shrinks nasal skin after rhinoplasty following failure of conservative measures". Plast Reconstr Surg, 2013. 131(4): p. 664e-6e.
Krischak, G.D., et al., "The effects of non-steroidal anti-inflammatory drug application on incisional wound healing in rats" Journal of Wound Care, vol. 6, No. 2, (Feb. 2007).
Laubach, H.J., et. al., "Confined Thermal Damage with Intense Ultrasound (IUS)" [abstr.] American Society for Laser Medicine and Surgery Abstracts, p. 15 #43 (Apr. 2006).

(56) References Cited

OTHER PUBLICATIONS

Laubach, H.J., et. al., "Intense focused ultrasound: evaluation of a new treatment modality for precise microcoagulation within the skin". Dermatol Surg, 2008. 34(5): p. 727-34.
Lee, H.J., et. al., "The efficacy and safety of intense focused ultrasound in the treatment of enlarged facial pores in Asian skin". J Dermatolog Treat, 2014.
Lee, H.S., et. al., "Multiple Pass Ultrasound Tightening of Skin Laxity of the Lower Face and Neck". Dermatol Surg, 2011.
Lin, Sung-Jan, et al., "Monitoring the thermally induced structural transitions of collagen by use of second-harmonic generation microscopy" Optics Letters, vol. 30, No. 6, (Mar. 15, 2005).
MacGregor J.L., et. al., "Microfocused Ultrasound for Skin Tightening". Semin Cutan Med Surg 32:18-25. (2013).
Madersbacher, S. et al., "Tissue Ablation in Benign Prostatic Hyperplasia with High Intensity Focused Ultrasound," Dur. Urol., 23 (suppl. 1):39-43; 1993.
Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pgs. 1788-1791, vol. 3.
Makin et al, "Confirmed Bulk Ablation and Therapy Monitoring Using Intracorporeal Image-Treat Ultrasound Arrays," 4th International Symposium on Therapeutic Ultrasound, Sep. 19, 2004.
Makin et al., "Miniaturized Ultrasound Arrays for Interstitial Ablation and Imaging," UltraSound Med. Biol. 2005, Nov. 1, 2005, pp. 1539-1550, vol. 31(11).
Manohar et al, "Photoacoustic mammography laboratory prototype: imaging of breast tissue phantoms," Journal of Biomedical Optics, Nov./Dec. 2004, pp. 1172-1181, vol. 9, No. 6.
Mast et al, "Bulk Ablation of Soft Tissue with Intense Ultrasound; Modeling and Experiments," J. Acoust. Soc. Am., Oct. 1, 2005, pp. 2715-2724, vol. 118(4).
Meshkinpour, Azin, et al., "Treatment of Hypertrophic Scars and Keloids With a Radiofrequency Device: A Study of Collagen Effects" Lasers in Surgery and Medicine 37:343-349 (2005).
Minkis, K., et. al., "Ultrasound skin tightening". Dermatol Clin, 2014. 32(1): p. 71-7.
Mitragotri, S., "Healing sound: the use of ultrasound in drug delivery and other therapeutic applications," Nature Reviews; Drug Delivery, pp. 255-260, vol. 4 (Mar. 2005).
Mosser, David M. et al., "Exploring the full spectrum of macrophage activation" Nat Rev Immunol; 8(12): 958-969. (Dec. 2008).
Murota, Sei-Itsu, et al., "Stimulatory Effect of Prostaglandins on the Production of Hexosamine-Containing Substances by Cultured Fibroblasts (3) Induction of Hyaluronic Acid Synthetase by Prostaglandin" Department of Pharmacology, Tokyo Metropolitan Institute of Gerontology, Itabashiku, Tokyo-173, Japan. (Nov. 1977, vol. 14, No. 5).
Murota, Sei-Itsu, et al., "The Stimulatory Effect of Prostaglandins on Production of Hexosamine-Containing Substances by Cultured Fibroblasts" Department of Pharmacology, Tokyo Metropolitan Institute of Gerontology, Itabashiku, Tokyo-173, Japan. (Aug. 1976, vol. 12, No. 2).
Nestor, M.S. et. al., "Safety and Efficacy of Micro-focused Ultrasound Plus Visualization for the Treatment of Axillary Hyperhidrosis". J Clin Aesthet Dermatol, 2014. 7(4): p. 14-21.
Oni, G., et. al. "Response to 'comments on evaluation of microfocused ultrasound system for improving skin laxity and tightening in the lower face'". Aesthet Surg J. Mar. 2015;35(3):NP83-4.
Oni, G., et. al., "Evaluation of a Microfocused Ultrasound System for Improving Skin Laxity and Tightening in the Lower Face". Aesthet Surg J, 2014. 38:861-868.
Pak, C.S., et. al., "Safety and Efficacy of Ulthera in the Rejuvenation of Aging Lower Eyelids: A Pivotal Clinical Trial". Aesthetic Plast Surg, 2014.
Paradossi et al., "Poly(vinyl alcohol) as versatile biomaterial for potential biomedical applications," Journal of Materials Science: Materials in Medicine, 2003, pp. 687-691, vol. 14.
Pritzker, R.N., et. al, "Updates in noninvasive and minimally invasive skin tightening". Semin Cutan Med Surg. Dec. 2014;33(4):182-7.
Pritzker, R.N., et. al., "Comparison of different technologies for noninvasive skin tightening". Journal of Cosmetic Dermatology, 13, 315-323. (2014).
Rappolee, Daniel A., et al., "Wound Macrophages Express TGF and Other Growth Factors in Vivo: Analysis by mRNA Phenotyping" Science, vol. 241, No. 4866 (Aug. 1988).
Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.
Righetti et al, "Elastographic Characterization of HIFU-Induced Lesions in Canine Livers," 1999, Ultrasound in Med & Bio, vol. 25, No. 7, pp. 1099-1113.
Rokhsar, C., et. al., "Safety and efficacy of microfocused ultrasound in tightening of lax elbow skin". Dermatol Surg. 2015; 41(7):821-6.
Rosenberg, Carol S. "Wound Healing in the Patient with Diabetes Mellitus" Nursing Clinics of North America, vol. 25, No. 1, (Mar. 1990).
Saad et al., "Ultrasound-Enhanced Effects of Adriamycin Against Murine Tumors," Ultrasound in Med. & Biol. vol. 18, No. 8, pp. 715-723 (1992).
Sabet-Peyman, E.J. et. al., "Complications Using Intense Ultrasound Therapy to TreatDeep Dermal Facial Skin and Subcutaneous Tissues". Dermatol Surg 2014; 40:1108-1112.
Sandulache, Vlad C. et al., "Prostaglandin E2 inhibition of keloid fibroblast migration, contraction, and transforming growth factor (TGF)-B1-induced collagen synthesis" Wound Rep Reg 15 122-133, 2007. (2007).
Sanghvi, N.T., et al., "Transrectal Ablation of Prostate Tissue Using Focused Ultrasound," 1993 Ultrasonics Symposium, IEEE, pp. 1207-1210.
Sasaki, G.H. et. al., "Clinical Efficacy and Safety of Focused-Image Ultrasonography: A 2-Year Experience". Aesthet Surg J, 2012.
Sasaki, G.H. et. al., "Microfocused Ultrasound for Nonablative Skin and Subdermal Tightening to the Periorbitum and Body Sites: Preliminary Report on Eighty-Two Patients". Journal of Cosmetics, Dermatological Sciences and Applications, 2012, 2, 108-116.
Sassen, Sander, "ATI's R520 architecture, the new king of the hill?" http://www.hardwareanalysis.com/content/article/1813, Sep. 16, 2005, 2 pages.
Seip, Ralf, et al., "Noninvasive Detection of Thermal Effects Due to Highly Focused Ultrasonic Fields," IEEE Symposium, pp. 1229-1232, vol. 2, Oct. 3-Nov. 1993.
Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.
Simon et al., "Applications of Lipid-Coated Microbubble Ultrasonic Contrast to Tumor Therapy," Ultrasound in Med. & Biol. vol. 19, No. 2, pp. 123-125 (1993).
Sklar, L.R., et. al., "Use of transcutaneous ultrasound for lipolysis and skin tightening: a review". Aesthetic Plast Surg, 2014. 38(2): p. 429-41.
Smith, Nadine Barrie, et al., "Non-invasive In Vivo Temperature Mapping of Ultrasound Heating Using Magnetic Resonance Techniques", 1994 Ultrasonics Symposium, pp. 1829-1832, vol. 3.
Suh, D.H., et. al., "A intense-focused ultrasound tightening for the treatment of infraorbital laxity". J Cosmet Laser Ther, 2012. 14(6): p. 290-5.
Suh, D.H., et. al., "Comparative histometric analysis of the effects of high-intensity focused ultrasound and radiofrequency on skin". J Cosmet Laser Ther. Mar. 24, 2015:1-7.
Suh, D.H., et. al., "Intense Focused Ultrasound Tightening in Asian Skin: Clinical and Pathologic Results" American Society for Dermatologic Surgery, Inc.; 37:1595-1602. (2011).
Surry et al., "Poly(vinyl alcohol) cryogel phantoms for use in ultrasound and MR imaging," Phys. Med. Biol., Dec. 6, 2004, pp. 5529-5546, vol. 49.
Syka J. E. P. et al., "Peptide and Protein Sequence Analysis by Electron Transfer Dissociation Mass Spectrometry," Proceedings of

(56) References Cited

OTHER PUBLICATIONS the National Academy of Sciences of USA, National Academy of Science, Washington, DC, vol. 101, No. 26, Jun. 29, 2004, pp. 9528-9533.
Talbert, D. G., "An Add-On Modification for Linear Array Real-Time Ultrasound Scanners to Produce 3D Displays," UTS Int'l 1977 Brighton, England (Jun. 28-30, 1977) pp. 57-67.
Tata et al., "Interaction of Ultrasound and Model Membrane Systems: Analyses and Predictions,"American Chemical Society, Phys. Chem. 1992, 96, pp. 3548-3555.
Ueno, S., et al., "Ultrasound Thermometry in Hyperthermia", 1990 Ultrasonic Symposium, pp. 1645-1652.
Verhofstad, Michiel H.J. et al., "Collagen Synthesis in rat skin and ileum fibroblasts is affected differently by diabetes-related factors" Int. J. Exp. Path. (1998), 79, 321-328.
Wang, H., et al., "Limits on Focused Ultrasound for Deep Hyperthermia", 1994 Ultrasonic Symposium, Nov. 1-4, 1994, pp. 1869-1872, vol. 3.
Wasson, Scott, "NVIDIA's GeForce 7800 GTX graphics processor Power MADD," http://techreport.com/reviews/2005q2/geforce-7800gtx/index.x?pg=1, Jun. 22, 2005, 4 pages.
Weiss, M., "Commentary: noninvasive skin tightening: ultrasound and other technologies: where are we in 2011?" Dermatol Surg, 2012. 38(1): p. 28-30.
White et al "Selective Creating of Thermal Injury Zones in the Superficial Musculoaponeurotic System Using Intense Ultrasound Therapy," Arch Facial Plastic Surgery, Jan./Feb. 2007, vol. 9, No. 1 (pp. 22-29).
White, W. M., et al., "Selective Transcutaneous Delivery of Energy to Facial Subdermal Tissues Using the Ultrasound Therapy System" [abstr]. American Society for Laser Medicine and Surgery Abstracts, p. 37 #113 (Apr. 2006).
White, W. Matthew, et al., "Selective Transcutaneous Delivery of Energy to Porcine Soft Tissues Using Intense Ultrasound (IUS)" Lasers in Surgery and Medicine 40:67-75 (2008).
Woodward, J.A., et. al. "Safety and Efficacy of Combining Microfocused Ultrasound With Fractional CO2 Laser Resurfacing for Lifting and Tightening the Face and Neck". Dermatol Surg, Dec. 2014 40:S190-S193.
Zelickson, Brian D. et al., "Histological and Ultrastructural Evaluation of the Effects of a Radiofrequency-Based Nonablative Dermal Remodeling Device, A Pilot Study" Arch Dermatol, vol. 140, (Feb 2004).
Ulthera, Inc., Petition for *Inter Partes* Review filed Jul. 19, 2016 in Re U.S. Pat. No. 6,113,559; IPR2016-01459; 63 pages (filed Jul. 19, 2016).
Ulthera Exhibit 1001, U.S. Pat. No. 6,113,559 to Klopotek, filed Jul. 19, 2016 in re IPR2016-01459.
Ulthera Exhibit 1002, Patent file history of U.S. Pat. No. 6,113,559 Klopotek filed Jul. 19, 2016 in re IPR2016-01459.
Ulthera Exhibit 1003, Declaration of Expert Witness Mark E. Schafer, Ph.D. filed Jul. 19, 2016 in re IPR2016-01459.
Ulthera Exhibit 1004, Curriculum Vitae of Mark E. Schafer, Ph.D. filed Jul. 19, 2016 in re IPR2016-01459.
Ulthera Exhibit 1005, International PCT Publication WO96/34568 Knowlton filed Jul. 19, 2016 in re IPR2016-01459.
Ulthera Exhibit 1006, French Patent No. 2,672,486, Technomed patent filed Jul. 19, 2016 in re IPR2016-01459.
Ulthera Exhibit 1007, English translation of French Patent No. 2,672,486, Technomed filed Jul. 19, 2016 in re IPR2016-01459.
Ulthera Exhibit 1008, International PCT Publication WO93/12742, Technomed PCT filed Jul. 19, 2016 in re IPR2016-01459.
Ulthera Exhibit 1009, English translation of International PCT Publication WO93/12742, Technomed PCT filed Jul. 19, 2016 in re IPR2016-01459.
Ulthera Exhibit 1010, U.S. Pat. No. 5,601,526, which claims priority to Technomed PCT filed Jul. 19, 2016 in re IPR2016-01459.
Ulthera Exhibit 1011, Patent file history for European Patent Application No. 98964890.2, Klopotek filed Jul. 19, 2016 in re IPR2016-01459.
Ulthera Exhibit 1012, Translator Declaration filed Jul. 19, 2016 in re IPR2016-01459.
Ulthera Exhibit 1013, U.S. Pat. No. 5,230,334 to Klopotek filed Jul. 19, 2016 in re IPR2016-01459.
Ulthera Exhibit 1014, U.S. Pat. No. 5,755,753 to Knowlton filed Jul. 19, 2016 in re IPR2016-01459.
Ulthera Exhibit 1015, Excerpts from The American Medical Association Encyclopedia of Medicine (1989) filed Jul. 19, 2016 in re IPR2016-01459.
Ulthera Exhibit 1016, The Simultaneous Study of Light Emissions and Shock Waves Produced by Cavitation Bubbles, G. Gimenez, J. Acoust. Soc. Am. 71(4), Apr. 1982, pp. 839-847 (filed Jul. 19, 2016 in re IPR2016-01459).
Ulthera Exhibit 1017, Excerpts from Gray's Anatomy (1995) (filed Jul. 19, 2016 in re IPR2016-01459).
Ulthera Exhibit 1018, Anatomy of the Superficial Venous System, Comjen G.M., Dermatol. Surg., 1995; 21:35-45 (filed Jul. 19, 2016 in re IPR2016-01459).
Ulthera Exhibit 1019, Section 2.6 from Ultrasonics Theory and Application, by G.L. Gooberman (Hart Publishing Co., 1969) (filed Jul. 19, 2016 in re IPR2016-01459).
Ulthera Exhibit 1020, Deep Local Hyperthermia for Cancer Therapy: External Electromagnetic and Ultrasound Techniques, A.Y. Cheung and A. Neyzari, Cancer Research (Suppl.), vol. 44, pp. 4736-4744 (1984) (filed Jul. 19, 2016 in re IPR2016-01459).
Decision on Institution of Inter Partes Review in Re U.S. Pat. No. 6,113,559; IPR2016-01459; 20 pages [011] (dated Jan. 23, 2017).
Dermafocus Response to Institution of Inter Partes Review in Re U.S. Pat. No. 6,113,559; IPR2016-01459; 73 pages [018] (dated Apr. 26, 2017).
Dermafocus Exhibit List in Re U.S. Pat. No. 6,113,559; IPR2016-01459; 5 pages [019] (dated Apr. 26, 2017).
Dermafocus Exhibit 2002, Declaration of Mark Palmeri, in Re U.S. Pat. No. 6,113,559; IPR2016-01459; 136 pages (filed Apr. 26, 2017).
Dermafocus Exhibit 2003, Deposition of Dr. Mark Schafer, in Re U.S. Pat. No. 6,113,559; IPR2016-01459; 327 pages (filed Apr. 26, 2017).
Dermafocus Exhibit 2004, Amendment No. 4 to Ulthera Form S-1, in Re U.S. Pat. No. 6,113,559; IPR2016-01459; 308 pages (filed Apr. 26, 2017).
Dermafocus Exhibit 2005, Excerpt from Churchill Livingstone, Gray's Anatomy (38th ed. 1995), in Re U.S. Pat. No. 6,113,559; IPR2016-01459; 7 pages (filed Apr. 26, 2017).
Dermafocus Exhibit 2006, Bo Eklof et al., "Revision of the CEAP Classification for Chronic Venous Disorders: Consensus Statement," ACTA FAC MED NAISS, vol. 25, No. 1 (2008), 3-10 in Re U.S. Pat. No. 6,113,559; IPR2016-01459; 7 pages (filed Apr. 26, 2017).
Dermafocus Exhibit 2007, WebMD, "Varicose Veins and Spider Veins" downloaded from http://www.webmd.com/skin-problems-andtreatments/guide/varicose-spider-veins#1 in Re U.S. Pat. No. 6,113,559; IPR2016-01459; 3 pages (filed Apr. 26, 2017).
Dermafocus Exhibit 2008, John M. Porter et al, "Reporting Standards in Venous Disease: an Update," Journal of Vascular Surgery, vol. 21, No. 4 (1995), 635-645 in Re U.S. Pat. No. 6,113,559; IPR2016-01459; 11 pages (filed Apr. 26, 2017).
Dermafocus Exhibit 2009, Kullervo Hynynen, "Review of Ultrasound Therapy," 1997 Ultrasonics Symposium (1997), 1305-1313, in Re U.S. Pat. No. 6,113,559; IPR2016-01459; 9 pages (filed Apr. 26, 2017).
Dermafocus Exhibit 2010, A.G. Visioli et al, "Preliminary Results of a Phase I Dose Escalation Clinical Trial Using Focused Ultrasound in the Treatment of Localised Tumours," European Journal of Ultrasound, vol. 9 (1999), 11-18, in Re U.S. Pat. No. 6,113,559; IPR2016-01459; 8 pages (filed Apr. 26, 2017).
Dermafocus Exhibit 2011, U.S. Pat. No. 5,143,063, dated Sep. 1,1992, Fellner, in Re U.S. Pat. No. 6,113,559; IPR2016-01459; 6 pages (filed Apr. 26, 2017).
Dermafocus Exhibit 2012, Hugh G. Beebe et al, "Consensus Statement: Classification and Grading of Chronic Venous Disease in the Lower Limbs," European Journal of Vascular and Endovascular

(56) References Cited

OTHER PUBLICATIONS

Surgery, vol. 12 (1996), 487-492, in Re U.S. Pat. No. 6,113,559; IPR2016-01459; 6 pages (filed Apr. 26, 2017).
Dermafocus Exhibit 2013, Excerpt from Mosby's Medical Dictionary (3rd ed. 1990), in Re U.S. Pat. No. 6,113,559; IPR2016-01459; 4 pages (filed Apr. 26, 2017).
Dermafocus Exhibit 2014, Excerpt from Miller-Keane Encyclopedia & Dictionary of Medicine, Nursing, & Allied Health (5th ed. 1992), in Re U.S. Pat. No. 6,113,559; IPR2016-01459; 6 pages (filed Apr. 26, 2017).
Dermafocus Exhibit 2015, David J. Tibbs et al, Varicose Veins, Venous Disorders, and Lymphatic Problems in the Lower Limbs (1997), Chapter 4: Clinical Patterns of Venous Disorder I, 47-67, in Re U.S. Pat. No. 6,113,559; IPR2016-01459; 24 pages (filed Apr. 26, 2017).
Dermafocus Exhibit 2016, Mitchel P. Goldman et al, Varicose Veins and Telangiectasias (2nd ed. 1999), Chapter 22: Treatment of Leg Telangiectasias with Laser and High-Intensity Pulsed Light, 470-497, in Re U.S. Pat. No. 6,113,559; IPR2016-01459; 31 pages (filed Apr. 26, 2017).
Dermafocus Exhibit 2017, Email from Anderson to Klopotek dated May 25, 2004, in Re U.S. Pat. No. 6,113,559; IPR2016-01459; 1 page (filed Apr. 26, 2017).
Dermafocus Exhibit 2018, List of Klopotek Patents, in Re U.S. Pat. No. 6,113,559; IPR2016-01459; 411 pages (filed Apr. 26, 2017).
Dermafocus Exhibit 2019, Declaration of Peter Klopotek Civil Action 15-cv-654-SLR, dated Nov. 2, 2016, in Re U.S. Pat. No. 6,113,559; IPR2016-01459; 1 page (filed Apr. 26, 2017).
Dermafocus Exhibit 2020, "Our Technology," downloaded from http://jobs.ulthera.com/about on Apr. 10, 2017, in Re U.S. Pat. No. 6,113,559; IPR2016-01459; 4 pages (filed Apr. 26, 2017).
Dermafocus Exhibit 2021, C. Damianou and K. Hynynen, "Focal Spacing and Near-Field Heating During Pulsed High Temperature Ultrasound Therapy," Ultrasound in Medicine & Biology, vol. 19, No. 9 (1993), 777-787, in Re U.S. Pat. No. 6,113,559; IPR2016-01459; 11 pages (filed Apr. 26, 2017).
Dermafocus Exhibit 2022, Excerpt from Mosby's Medical Dictionary (5th ed. 1997), in Re U.S. Pat. No. 6,113,559; IPR2016-01459; 5 pages (filed Apr. 26, 2017).
Dermafocus Exhibit 2023, Excerpt from Miller-Keane Encyclopedia & Dictionary of Medicine, Nursing, & Allied Health (6th ed. 1997), in Re U.S. Pat. No. 6,113,559; IPR2016-01459; 7 pages (filed Apr. 26, 2017).
Dermafocus Exhibit 2024, Excerpt from Stedman 's Concise Medical Dictionary (3 rd ed. 1997), in Re U.S. Pat. No. 6,113,559; IPR2016-01459; 4 pages (filed Apr. 26, 2017).
Dermafocus Exhibit 2025, Excerpt from Taber's Cyclopedic Medical Dictionary (18th ed. 1997), in Re U.S. Pat. No. 6,113,559; IPR2016-01459; 9 pages (filed Apr. 26, 2017).
Dermafocus Exhibit 2026, Bo Eklof et al, "Revision of the CEAP Classification for Chronic Venous Disorders: Consensus Statement," Journal ofVascular Surgery, vol. 40, No. 6 (2004), 1248-1252.el, in Re U.S. Pat. No. 6,113,559; IPR2016-01459; 6 pages (filed Apr. 26, 2017).
Ulthera, Inc., Reply in Support of Petition for Inter Partes Review in Re U.S. Pat. No. 6,113,559; IPR2016-01459; 33 pages (filed Aug. 2, 2017).
Ulthera Exhibit 1022, Use of the Argon and Carbon Dioxide Lasers for Treatment of Superficial Venous Varicosities of the Lower Extremity, D. Apfelberg et al., Lasers in Surgery and Medicine, vol. 4.3, pp. 221-231 (1984) (filed Aug. 2, 2017 in re IPR2016-01459).
Ulthera Exhibit 1023, 532-Nanometer Green Laser Beam Treatment of Superficial Varicosities of the Lower Extremities, T. Smith et al., Lasers in Surgery and Medicine, vol. 8.2, pp. 130-134 (1988) (filed Aug. 2, 2017 in re IPR2016-01459).
Ulthera Exhibit 1024, Deposition Transcript of Dr. Mark Palmeri on Jul. 11, 2017 (filed Aug. 2, 2017 in re IPR2016-01459).
Carruthers et al., "Consensus Recommendations for Combined Aesthetic Interventions in the Face Using Botulinum Toxin, Fillers,and Energy-Based Devices" Dermatol Surg 2016 (pp. 1-12).
Casabona, G., et. al., "Microfocused Ultrasound with Visualization and Calcium Hydroxylapatite for Improving Skin Laxity and Cellulite Appearance"; Plast Reconstr Surg Glob Open. Jul. 25, 2017;5(7):e1388, 8 pages.
Hexsel et al., "A Validated Photonumeric Cellulite Severity Scale"; J Eur Acad Dermatol Venereol. May 2009; 23(5):523-8, 6 pages.
Microchip microID 125 kHz EFID System Design Guide, Microchip Technology Inc. (2004).
Ulthera Exhibit 1025, Ulthera Oral Proceeding Demonstrative Slides (filed Oct. 2, 2017 in re IPR2016-01459).
Dermafocus Exhibit 2027, DermaFocus Oral Proceeding Demonstrative Slides (filed Oct. 2, 2017 in re IPR2016-01459).
PTAB Record of Oral Hearing held Oct. 4, 2017 in Re U.S. Pat. No. 6,113,559; IPR2016- 01459; 67 pages (PTAB Document sent to Ulthera on Nov. 1, 2017).
Final Written Decision of Inter Partes Review in Re U.S. Pat. No. 6,113,559; IPR2016-01459; 37 pages [030] (Entered Jan. 19, 2018).
Ulthera, Inc., Petitioner Notice of Appeal to Federal Circuit 2018-1542 re: IPR2016-01459; 4 pages from [001] (no appendices) (filed Feb. 9, 2018).
Federal Circuit Order Granting Ulthera Motion to Remand, re: 2018-1542; 4 pages [022] (dated May 25, 2018).
Adams et al., "High Intensity Focused Ultrasound Ablation of Rabbit Kidney Tumors" Sonablate High-Intensity Focused Ultrasound device; Journal of Endourology vol. 10, No. 1, (Feb. 1996).
Driller et al., "Therapeutic Applications of Ultrasound: A Review" IEEE Engineering in Medicine and Biology; (Dec. 1987) pp. 33-40.
Sonocare, Inc. Therapeutic Ultrasound System Model CST-100 Instruction Manual (1985).
Webster et al. "The role of ultrasound-induced cavitation in the 'in vitro' stimulation of collagen synthesis in human fibroblasts"; Ultrasonics pp. 33-37(Jan. 1980).
Ulthera Brief (Corrected), Fed. Cir. Appeal Case 19-1006 from re: IPR2016-01459; 136 pages [030] (dated Apr. 3, 2019).
DermaFocus Brief (Corrected), Fed. Cir. Appeal Case 19-1006 from re: IPR2016-01459; 73 pages [032] (dated Apr. 4, 2019).
Supplemental European Search Report in EP15780378 dated Nov. 21, 2017 (131EP).
Brown J A et al: "Fabrication and performance of 40-60 MHz annular arrays", 2003 IEEE Ultrasonics Symposium Proceedings. Honolulu, Hawaii, Oct. 5-8, 2003; [IEEE Ultrasonics Symposium Proceedings], New York, NY : IEEE, US, vol. 1, Oct. 5, 2003 (Oct. 5, 2003), pp. 869-872.
Ketterling J. A. et al.: "Design and fabrication of a 40-MHz annular array transducer", IEEE Transactions on Ultrasonics, Ferroelectrics and Frequency Control, IEEE, US, vol. 52, No. 4, Apr. 1, 2005 (Apr. 1, 2005), pp. 672-681.

\* cited by examiner

Isoeffective Dosages To Theoretically Achieve 1% Survival Fraction

| Temperature (°C) | Exposure time (min) | Exposure Time (sec) |
|---|---|---|
| 43 | 100.00 | 6000 |
| 44 | 50.00 | 3000 |
| 45 | 25.00 | 1500 |
| 46 | 12.50 | 750 |
| 47 | 6.25 | 375 |
| 48 | 3.13 | 188 |
| 49 | 1.56 | 94 |
| 50 | 0.78 | 47 |
| 51 | 0.39 | 23 |
| 52 | 0.20 | 12 |
| 53 | 0.10 | 6 |
| 54 | 0.05 | 3 |
| 55 | 0.02 | 1 |

*FIG. 41*

3-Factor 3-Level DOE to Determine Settings for an Isoeffective Dosage Study

| Power | Time-on | Time-off | Spacing | #"TCPs" | Energy/Line | Energy/Pass |
|---|---|---|---|---|---|---|
| [W] | [ms] | [ms] | [mm] | [#] | [J] | [J] |
| 10 | 30 | 34 | 0.3 | 84 | 0.3 | 25.2 |
| 15 | 20 | 34 | 0.3 | 84 | 0.3 | 25.2 |
| 15 | 30 | 34 | 0.2 | 125 | 0.45 | 56.3 |
| 15 | 30 | 34 | 0.3 | 84 | 0.45 | 37.8 |
| 15 | 40 | 34 | 0.3 | 84 | 0.6 | 50.4 |
| 20 | 30 | 34 | 0.3 | 84 | 0.6 | 50.4 |
| 15 | 30 | 34 | 0.1 | 250 | 0.45 | 112.5 |

FIG. 47

Time-Temperature Goals for Thermal Dosage Testing

| Site | Target Time [min] | Target Time [sec] | Target Temperature [°C] |
|---|---|---|---|
| C1 | 0.10 | 6 | 60 |
| 1 | 5.00 | 300 | 45 |
| 2 | 1.00 | 60 | 45 |
| 3 | 5.00 | 300 | 48 |
| 4 | 1.00 | 60 | 48 |
| 5 | 0.20 | 12 | 48 |
| 6 | 1.00 | 60 | 51 |
| 7 | 0.20 | 12 | 52 |

*FIG. 49*

3.5Mhz, 22mm width, 6.0mm Depth Cylindrical Transducer Treatment Settings For Isoeffective Thermal Dosage Study

| Power [W] | Time-on [ms] | Time-off [ms] | Spacing [mm] | #"TCPs" [#] | Energy/Line [J] | Energy/Pass [J] |
|---|---|---|---|---|---|---|
| 15 | 30 | 34 | 0.3 | 84 | 0.45 | 37.8 |
| 15 | 60 | 67 | 0.7 | 36 | 0.9 | 32.4 |

*FIG. 50*

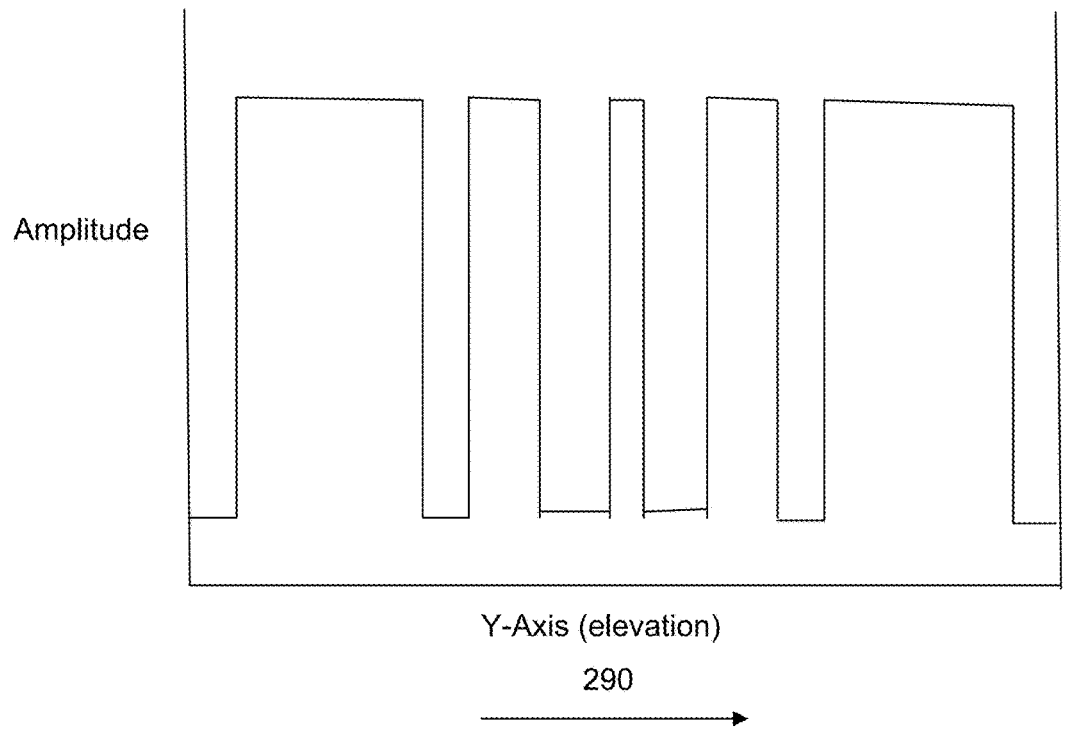
FIG. 58
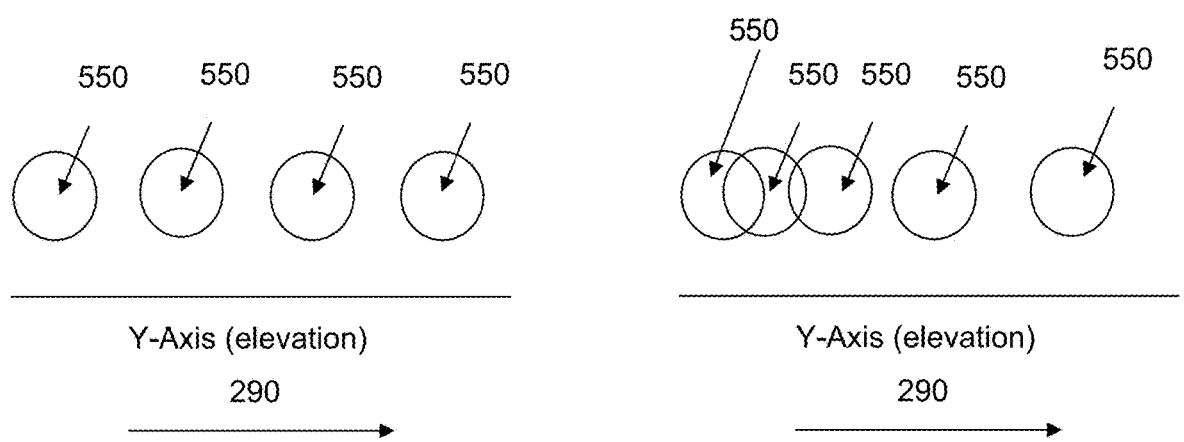
FIG. 59  FIG. 60

BAND TRANSDUCER ULTRASOUND THERAPY

CROSS-REFERENCE TO RELATED APPLICATIONS

This application is a continuation from U.S. application Ser. No. 15/302,436 filed Oct. 6, 2016, a National Phase from International App. No. PCT/US2015/025581 filed Apr. 13, 2015, published in English as WO 2015/160708, which claims the benefit of priority from U.S. Provisional Application No. 61/981,660 filed Apr. 18, 2014, each of which is incorporated in its entirety by reference, herein.

FIELD

Several embodiments of the present invention generally relate to noninvasive, semi-invasive, and/or invasive energy-based treatments to achieve cosmetic and/or medical effects. For example, some embodiments generally relate to devices, systems and methods with linear, curved, planar, and/or three-dimensional ultrasound treatment focus zones for performing various treatment procedures safely and effectively. Various embodiments of a treatment system can improve cosmetic results and patient outcomes through reduced treatment time and/or reduced treatment energy, which can increase comfort and cosmetic outcomes. In various embodiments, ultrasound transducers have treatment focus zones in the form of one or more lines, belts, bands, and/or planes.

DESCRIPTION OF THE RELATED ART

Many cosmetic procedures involve invasive procedures that may require invasive surgery, which can places more requirements on biocompatibility and sterility. Patients not only have to endure weeks of recovery time, but also are frequently required to undergo risky anesthetic procedures for aesthetic treatments. Traditional cosmetic procedures involving piercing or cutting the skin surface to access target tissue under the skin surface tend to involve higher requirements on biocompatibility and sterility. Certain traditional energy based treatments, such as with radio-frequency (RF) and laser treatments must heat or treat tissue starting from the skin surface affecting all the intermediary tissue between the skin surface and a target tissue at a depth under the skin surface.

SUMMARY

Although energy-based treatments have been disclosed for cosmetic and medical purposes, no procedures are known to Applicant, other that Applicant's own work, that successfully achieve an aesthetic tissue heating and/or treatment effect using targeted and precise ultrasound to cause a visible and effective cosmetic results via a thermal pathway by using band shaped treatment focus zone techniques to expand the area and volume of tissue treated at a specific, targeted area. Treatment can include heating, coagulation, and/or ablation (including, for example, hyperthermia, thermal dosimetry, apoptosis, and lysis). In various embodiments, band treatment provides improved thermal heating and treatment of tissue compared to diathermy or general bulk heating techniques. In various embodiments, band treatment provides the capability of heating and/or treating tissue at specific depth ranges without affecting proximal tissues. In general, diathermy and bulk heating techniques usually involve heating a skin surface and conducting the heat through the skin surface and all underlying tissue to reach a tissue at a target depth below the skin surface. In various embodiments, band treatment provides targeted heating and treatment at a specific, prescribed depth range below the skin surface without heating the skin surface and/or intermediary tissue between the skin surface and the target tissue. This offset band treatment reduces damage and associated pain at the skin surface, and treats tissue only at the prescribed, targeted tissue depth. Thus, embodiments of the present invention can be used to treat tissue in a specific range of depths below the skin surface without heating the skin surface. In some embodiments, band treatment can also be used to prepare tissue at target depths for a second, ultrasound treatment by pre-heating the target tissue to an elevated temperature so the secondary treatment can be performed with reduced time and/or energy and increased comfort.

In accordance with various embodiments, a cosmetic ultrasound treatment system and/or method can non-invasively produce single or multiple cosmetic treatment zones and/or thermal treatment points, lines, bands, belts, planes, areas, volumes, and/or shapes, where ultrasound is focused in one or more locations in a region of treatment in tissue at one or more depths under a skin surface. Some systems and methods provide cosmetic treatment at different locations in tissue, with treatment areas at various depths, heights, widths, and/or positions. In one embodiment, a method and system comprise a transducer system configured for providing ultrasound treatment to more than one region of interest, such as between at least two treatment positions and/or regions of interest. In one embodiment, a method and system comprise a transducer system configured for providing ultrasound treatment to more than one region of interest, such as between at least two lines in various locations (e.g. at a fixed or variable depth, height, width, orientation, etc.) in a region of interest in tissue. In various embodiments, lines can be straight, curved, continuous, and/or non-continuous. In some embodiments, the energy beam is split to focus at two, three, four, or more focal zones (e.g., multiple focal lines, multi-focal lines) for cosmetic treatment zones and/or for imaging in a region of interest in tissue. Position of the focal zones can be positioned axially, laterally, or otherwise within the tissue. Some embodiments can be configured for spatial control, such as by the location of a focus line, changing the distance or angle between a transducer and an optional motion mechanism, and/or changing the angles of energy focused or unfocused to the region of interest, and/or configured for temporal control, such as by controlling changes in the frequency, drive amplitude and timing of the transducer. In some embodiments the position of multiple treatment zones can be enabled through poling, phasic poling, biphasic poling, and/or multi-phasic poling. As a result, changes in the location of the treatment region, the number, shape, size and/or volume of treatment zones, heating zones, and/or lesions in a region of interest, as well as the thermal conditions, can be dynamically controlled over time. Additional details regarding poling and modulation are disclosed in U.S. application Ser. No. 14/193,234 filed on Feb. 28, 2014 and published as U.S. Publication No. 2014-0257145, which is incorporated in its entirety by reference herein.

In one embodiment, an aesthetic imaging and treatment system includes a hand held probe with a housing that encloses an ultrasound transducer configured to apply ultrasound therapy to tissue at a focal zone. In one embodiment, the focal zone is a line. In one embodiment, the focal zone is a two dimensional region or plane. In one embodiment, the focal zone is a volume. In various embodiments, the focal zone treats a treatment area that is linear, curved, rectangular, and/or planar. In various embodiments, the size of the treatment area depends on the size of the transducer. The treatment can be performed in lines and/or planes. In various embodiments, the width of the treatment focal zone is 5-50 mm, 5-30 mm, 5-25 mm, 10-25 mm, 10 mm-15 mm, 15 mm-20 mm, 10 mm, 15 mm, 20 mm, 25 mm, or any range therein (including but not limited to 12 mm-22 mm). In various embodiments, a focal zone can be moved to sweep a volume between a first position and a second position. In various embodiments, one or more a focal zone locations are positioned in a substantially linear sequence within a cosmetic treatment zone. In various embodiments, one or more a focal zone locations are positioned with one, two, or more motion mechanisms to form any shape for a treatment area within a cosmetic treatment zone. In one embodiment, a first set of locations is positioned within a first cosmetic treatment zone and a second set of locations is positioned within a second cosmetic treatment zone, the first zone being different from the second zone. In one embodiment, the first cosmetic treatment zone includes a substantially linear sequence of the first set of locations and the second cosmetic treatment zone includes a substantially linear sequence of the second set of locations. In some non-limiting embodiments transducers can be configured for a treatment zone at a tissue depth below a skin surface of 1.5 mm, 3 mm, 4.5 mm, 6 mm, less than 3 mm, between 1.5 mm and 3 mm, between 1.5 mm and 4.5 mm, more than more than 4.5 mm, more than 6 mm, and anywhere in the ranges of 0.1 mm-3 mm, 0.1 mm-4.5 mm, 3 mm-7 mm, 3 mm-9 mm, 0.1 mm-25 mm, 0.1 mm-100 mm, and any depths therein (including, for example, 4.5 mm-6 mm, 1 mm-20 mm, 1 mm-15 mm, 1 mm-10 mm, 5 mm-25 mm, and any depths therein). In one embodiment, cosmetic treatment zones are continuous. In one embodiment, cosmetic treatment zones have no spacing. In one embodiment, a sequence of individual cosmetic treatment zones with a treatment spacing in a range from about 0.05 mm to about 25 mm (e.g., 0.05-0.1 mm, 0.05-1 mm, 0.2-0.5 mm, 0.5-2 mm, 1-10 mm, 0.5-3 mm, 5-12 mm). In various embodiments, the treatment spacing has a constant pitch, a variable pitch, an overlapping pitch, and/or a non-overlapping pitch.

In one embodiment, the ultrasonic transducer is configured to provide therapeutic intensity on the transducer surface in a range of between about 1 W/cm$^2$ to 100 W/cm$^2$ (e.g., 1-50, 10-90, 25-75, 10-40, 50-80 W/cm$^2$ and any ranges and values therein). In one embodiment, the ultrasonic transducer is configured to provide an acoustic power of the ultrasonic therapy in a range of between about 1 W to about 100 W and a frequency of about 1 MHz to about 10 MHz to thermally heat the tissue. In various embodiments, the transducer module is configured to provide an acoustic power of the ultrasonic therapy in a range of between about 1 W to about 100 W (e.g., 5-40 W, 10-50 W, 25-35 W, 35-60 W, 35 W, 40 W, 50 W, 60 W) and a frequency of about 1 MHz to about 10 MHz to thermally heat the tissue. In one embodiment, the acoustic power can be from a range of 1 W to about 100 W in a frequency range from about 1 MHz to about 12 MHz (e.g., 3.5 MHz, 4 MHz, 4.5 MHz, 7 MHz, 10 MHz, 3-5 MHz), or from about 10 W to about 50 W at a frequency range from about 3 MHz to about 8 MHz. In one embodiment, the acoustic power and frequencies are about 40 W at about 4.3 MHz and about 30 W at about 7.5 MHz. In various embodiments, the transducer module is configured to deliver energy with no pitch or a pitch of 0.1-2 mm (e.g., 0.4, 0.5, 0.6, 0.7, 0.8, 0.9, 1.0, 1.1, 1.2, 1.5 mm). In various embodiments, the pitch is constant or variable. In various embodiments, the transducer module is configured to deliver energy with an on-time of 10-500 ms (e.g., 30-100, 90-200, 30, 32, 35, 40, 50, 60, 64, 75, 90, 100, 112, 200, 300, 400 ms and any range therein). In various embodiments, the transducer module is configured to deliver energy with an off-time of 1-200 ms (e.g., 4, 10, 22, 45, 60, 90, 100, 150 ms and any range therein). In one embodiment, an acoustic energy produced by this acoustic power can be between about 0.01 joule ("J") to about 10 J or about 2 J to about 5 J. In one embodiment, the acoustic energy is in a range less than about 3 J. In various embodiments, an acoustic energy produced by this acoustic power in a single dose pass can be between about 1-500 J (e.g., 20-310, 70, 100, 120, 140, 150, 160, 200, 250, 300, 350, 400, 450 J and any range therein). In various embodiments, a treatment can involve 1, 2, 3, 4, 5, 10 or more dose passes.

In several embodiments disclosed herein, non-invasive ultrasound is used to achieve one or more of the following effects: tissue heating, tissue pre-heating, a face lift, a brow lift, a chin lift, an eye treatment, a wrinkle reduction, a scar reduction, a burn treatment, a tattoo removal, a vein removal, a vein reduction, a treatment on a sweat gland, a treatment of hyperhidrosis, a fat or adipose and/or cellulite reduction, a sun spot removal, an acne treatment, a pimple reduction. Treatment of the décolletage is provided in several embodiments. In another embodiment the system, device and/or method may be applied in the genital area (e.g., vaginal rejuvenation and/or vaginal tightening, such as for tightening the supportive tissue of the vagina). In several of the embodiments described herein, the procedure is entirely cosmetic and not a medical act. For example, in one embodiment, the methods described herein need not be performed by a doctor, but at a spa or other aesthetic institute. In some embodiments, a system can be used for the non-invasive cosmetic treatment of skin.

In one embodiment, a method of reducing variance in focal gain of a cylindrical ultrasound transducer includes providing a cylindrical transduction element comprising a convex surface and a concave surface, wherein one of the surfaces (e.g., the concave surface) comprises a plurality of electrodes (or e.g., electrical conductor or electrical material), and subsequently applying a current to the electrode, thereby directing ultrasound energy to a linear focal zone at a focal depth. The ultrasound energy produces a reduced variance in focal gain at the linear focal zone. The concave surface can be plated with silver. The convex surface can include an uncoated region and a plurality of coated regions. The plurality of coated regions can include fired silver to form the plurality of electrodes. The features on the convex surface can instead be on the concave surface.

In one embodiment, the reduction of edge noise facilitates the efficient and consistent treatment of tissue, wherein the cylindrical transduction element is configured to apply ultrasonic therapy to a linear tissue thermal treatment zone at a focal depth.

In one embodiment, the reduction of edge noise facilitates the efficient and consistent heating of a material, wherein the material is any one of the group consisting of a compound, an adhesive, and food.

In one embodiment, an ultrasound transduction system for reducing edge noise at a focal line includes a cylindrical transduction element and a power source configured to drive the cylindrical transduction element. The cylindrical transduction element is configured to apply ultrasonic energy to a linear focal zone at a focal depth. The cylindrical transduction element includes a convex surface and a concave surface. The concave surface is plated with an electrical conductor, such as silver. The convex surface includes an uncoated region and one or more coated regions, wherein the one or more coated regions includes silver to form an electrode. The power source is in electric communication with the electrode. The coated regions are configured to reduce variance in focal gain at the linear focal zone at the focal depth.

In one embodiment, an ultrasound transduction system for reducing edge noise at a focal line includes a cylindrical transduction element and a power source configured to drive the cylindrical transduction element. The cylindrical transduction element is configured to apply ultrasonic energy to a linear focal zone at a focal depth. The cylindrical transduction element includes a convex surface and a concave surface. The convex surface plated with silver. The concave surface includes an uncoated region and one or more coated regions, wherein the one or more coated regions includes silver to form an electrode. The power source is in electric communication with the electrode. The coated regions are configured to reduce variance in focal gain at the linear focal zone at the focal depth.

In one embodiment, a coated transducer for reducing variance in focal gain at a focal zone includes a cylindrical transduction element comprising a convex surface and a concave surface. The concave surface is plated with silver. The convex surface includes an uncoated region and a plurality of coated regions. The plurality of coated regions includes silver to form a plurality of electrodes. The cylindrical transduction element is configured to apply ultrasonic therapy to a linear focal zone at a focal depth. The coated regions are configured to reduce variance in focal gain at the linear focal zone.

In one embodiment, a coated transducer for reducing variance in focal gain at a focal zone includes a cylindrical transduction element comprising a convex surface and a concave surface. In one embodiment the convex surface is plated. In one embodiment the concave surface is plated. In one embodiment the concave surface includes an uncoated region and a plurality of coated regions. In one embodiment the convex surface includes an uncoated region and a plurality of coated regions. The plurality of coated regions includes a conductor to form a plurality of electrodes. The cylindrical transduction element is configured to apply ultrasonic therapy to a linear focal zone at a focal depth. The coated regions are configured to reduce variance in focal gain at the linear focal zone.

In one embodiment, an aesthetic treatment system includes a cylindrical transduction element comprising a convex surface and a concave surface. In one embodiment the concave surface is plated with silver to form an electrode. In one embodiment the convex surface is plated with silver to form an electrode. In one embodiment the convex surface includes an uncoated region and one or more coated regions, wherein the one or more coated regions includes silver to form an electrode. In one embodiment the concave surface includes an uncoated region and one or more coated regions, wherein the one or more coated regions includes silver to form an electrode. The cylindrical transduction element is configured to apply ultrasonic therapy to a linear tissue thermal treatment zone at a focal depth. The coated regions are configured to reduce variance in focal gain at the thermal treatment zone. The cylindrical transduction element is housed within an ultrasonic hand-held probe. In one embodiment, the ultrasonic probe includes a housing, the cylindrical transduction element, and a motion mechanism. The ultrasound transducer is movable within the housing. The motion mechanism is attached to the ultrasound transducer and configured to move the ultrasound transducer along a linear path within the housing.

In one embodiment, an aesthetic imaging and treatment system includes an ultrasonic probe that includes a housing, a coated ultrasound transducer, and a motion mechanism. The ultrasound transducer is movable within the housing, the ultrasound transducer including a cylindrical transduction element and an imaging element. The cylindrical transduction element is configured to apply ultrasonic therapy to a linear tissue thermal treatment zone at a focal depth. The cylindrical transduction element has an opening configured for placement of the imaging element. The cylindrical transduction element includes a convex surface and a concave surface. In one embodiment, the entire concave surface is plated with silver. In one embodiment, the entire convex surface is plated with silver. In one embodiment, the convex surface includes an uncoated portion and one or more coated regions. In one embodiment, the concave surface includes an uncoated portion and one or more coated regions. The coated region includes silver to form an electrode. The coated regions are configured to reduce variance in focal gain at the thermal treatment zone. The motion mechanism is attached to the ultrasound transducer and configured to move the ultrasound transducer along a linear path within the housing.

As provided herein, one of the surfaces of the transduction element (either the convex or the concave surface) is fully coated (or at least 90% coated) with an electrically conductive material (including but not limited to silver or another metal or alloy) and the other surface (either the convex or the concave surface) has regions (or a pattern or patchwork) of coated and uncoated portions that are coated with an electrically conductive material (including but not limited to silver or another metal or alloy). This, in several embodiments, can be advantageous because it facilitates uniform heating (e.g., reducing temperature spikes or fluctuations). In some embodiments, both surfaces (convex and concave surfaces) contain regions (or a pattern or patchwork) of coated and uncoated portions. Although convex and concave surfaces are described herein, one or both of these surfaces may be planar in some embodiments. Additionally, convex or concave surfaces as described herein may be multi-faceted (e.g., with multiple convexities and/or concavities) and also include surfaces with a curvature (e.g., one or more angles less than 180 degrees). In several embodiments, the pattern of coated and uncoated regions can include one, two or more coated regions and one, two or more uncoated regions, wherein the coated regions cover at least 60%, 70%, 80%, or 90% of the surfaces. Further, the uncoated region may be considered uncoated to the extent it does not have an electrically conductive coating—the uncoated region may have other types of surface coatings in certain embodiments.

In various embodiments, an ultrasound system includes a transducer with a transduction element (e.g., a flat, round, circular, cylindrical, annular, have rings, concave, convex, contoured or other shaped transduction element).

In various embodiments, an ultrasound transduction system, includes a transduction element (e.g., a cylindrical transduction element), and a power source configured to drive the transduction element, wherein the transduction element is configured to apply ultrasonic energy to a linear focal zone at a focal depth, wherein the transduction element comprises a first surface and a second surface, wherein the first surface comprises an electrically conductive coating, wherein the second surface comprises at least one electrically conductive coated region and at least one uncoated region that is not coated with an electrically conductive coating, wherein the at least one coated region on the second surface comprises a conductive material that forms an electrode when the power source is in electric communication with the at least one coated region, wherein the at least one coated region on the second surface is configured to reduce edge noise at the linear focal zone at the focal depth.

In various embodiments, an ultrasound transduction system includes a cylindrical transduction element and a power source configured to drive the cylindrical transduction element, wherein the cylindrical transduction element is configured to apply ultrasonic energy to a linear focal zone at a focal depth. In some embodiments, the cylindrical transduction element comprises a first surface and a second surface, wherein the first surface comprises a coating, wherein the second surface comprises at least one coated region and at least one uncoated region, wherein the at least one coated region on the second surface comprises a conductive material that forms an electrode when the power source is in electric communication with the at least one coated region, wherein the at least one coated region on the second surface is configured to reduce edge noise at the linear focal zone at the focal depth.

In an embodiment, the uncoated region does not comprise a conductive material. In an embodiment, the conductive material is a metal (e.g., silver, gold, platinum, mercury, and/or copper, or an alloy). In an embodiment, the first surface is a concave surface and the second surface is a convex surface. In an embodiment, the first surface is a convex surface and the second surface is a concave surface. In an embodiment, the cylindrical transduction element is housed within an ultrasonic hand-held probe, wherein the ultrasonic probe includes a housing, the cylindrical transduction element, and a motion mechanism, wherein the ultrasound transducer is movable within the housing, wherein the motion mechanism is attached to the ultrasound transducer and configured to move the ultrasound transducer along a linear path within the housing. In an embodiment, the motion mechanism automatically moves the cylindrical transduction element to heat a treatment area at the focal depth to a temperature in a range between 40-65 degrees Celsius (e.g., 40-45, 40-50, 40-55, 45-60, 45-55, 45-50 degrees Celsius, and any values therein). In an embodiment, the reduction of edge noise facilitates the production of a uniform (e.g., completely uniform, substantially uniform, about uniform) temperature in a treatment area. In an embodiment, the reduction of edge noise facilitates the efficient and consistent treatment of a tissue, wherein the cylindrical transduction element is configured to apply ultrasonic therapy to a treatment zone at the focal depth in the tissue. In an embodiment, the reduction of edge noise reduces a peak such that a variance around the focal depth is reduced by 75-200% (e.g., 75-100, 80-150, 100-150, 95-175%, and any values therein). In an embodiment, the reduction of edge noise reduces a peak such that a variance of an intensity around the focal depth is 5 mm or less (e.g., 4.5, 4, 3.5, 3, 2.5, 2, 1.5, 1, 0.5 or less). In an embodiment, the reduction of edge noise reduces a variance in focal gain in a range of 0.01-10 (e.g., 1-5, 2-8, 0.5-3, and any any values therein). In an embodiment, the power source is configured to drive the cylindrical transduction element to produce a temperature in a range of 42-55 degrees Celsius (e.g., 43-48, 45-53, 45-50 degrees Celsius, and any values therein) in a tissue at the focal depth. In an embodiment, a temperature sensor is located on the housing proximate an acoustic window in the housing configured to measure a temperature at a skin surface. In an embodiment, a system includes one or more imaging elements, wherein the cylindrical transduction element has an opening configured for placement of the one or more imaging elements. In an embodiment, the imaging element is configured to confirm a level of acoustic coupling between the system and a skin surface. In an embodiment, the imaging element is configured to confirm a level of acoustic coupling between the system and a skin surface via any one of the group consisting of: defocused imaging and Voltage Standing Wave Ratio (VSWR). In an embodiment, the imaging element is configured to measure a temperature at a target tissue at the focal depth below a skin surface. In an embodiment, the imaging element is configured to measure a temperature at a target tissue at the focal depth below a skin surface with any one of the group of Acoustic Radiation Force Impulse (ARFI), Shear Wave Elasticity Imaging (SWEI), and measurement of attenuation.

In several embodiments, a method of heating tissue with a cylindrical ultrasound transducer includes providing a cylindrical transduction element comprising a first surface, a second surface, a coated region, and an uncoated region. In some embodiments, the coated region comprises an electrical conductor. In some embodiments, the uncoated region does not comprise an electrical conductor. In some embodiments, the first surface comprises at least one coated region, wherein the second surface comprises the uncoated region and a plurality of coated regions, applying a current to the coated region, thereby directing ultrasound energy to a linear focal zone at a focal depth, wherein the ultrasound energy produces a reduction in focal gain at the linear focal zone.

In several embodiments, a cosmetic method of non-invasively and non-ablatively heating tissue with a heating source (e.g., a cylindrical ultrasound transducer) to heat the region under a subject's skin by between 5-25 degrees Celsius) while causing the temperature at the skin surface to stay the same or increases to a temperature that does not causing discomfort (e.g., by 1-5, 1-10, 1-15 degrees Celsius). This differential aids in the comfort of the subject. The heating, in one embodiment, occurs in increments over a period of 5-120 minutes with a graded or gradual increase in temperature. The heating can be performed by the cylindrical ultrasound transducer systems described herein. Optionally, an ablative or coagulative energy can subsequently be applied by increasing the temperature by another 5-25 degrees Celsius. The initial pre-heating step or bulk heating is advantageous because it allows less energy to be applied to achieve the coagulative/ablative state. In one embodiment, the initial pre-heating step is performed with a heating source other than an ultrasound transducer. For example, radiofrequency, microwave, light, convective, conversion, and/or conductive heat sources can be used instead of or in addition to ultrasound.

In several embodiments, a non-invasive, cosmetic method of heating tissue includes applying a cosmetic heating system to a skin surface, wherein the cosmetic heating system comprises a hand-held probe. In some embodiments, the hand-held probe comprises a housing that encloses an ultrasound transducer configured to heat tissue below the skin surface to a tissue temperature in the range of 40-50 degrees Celsius (e.g., 44-47, 41-49, 45-50 degrees Celsius, and any values therein). In some embodiments, the ultrasound transducer comprises a cylindrical transduction element comprising a first surface, a second surface, a coated region, and an uncoated region, wherein the coated region comprises an electrical conductor, wherein the first surface comprises at least one coated region, wherein the second surface comprises the uncoated region and a plurality of coated regions. In some embodiments, the method includes applying a current to the plurality of coated regions, thereby directing ultrasound energy to a linear focal zone at a focal depth, wherein the ultrasound energy produces a reduction in focal gain at the linear focal zone, thereby heating the tissue at the focal depth in the linear focal zone to the tissue temperature in the range of 40-50 degrees Celsius for a cosmetic treatment duration of less than 1 hour (e.g., 1-55, 10-30, 5-45, 15-35, 20-40 minutes and any values therein), thereby reducing a volume of an adipose tissue in the tissue.

In an embodiment, the reduction of focal gain facilitates the efficient and consistent treatment of tissue, wherein the cylindrical transduction element is configured to apply ultrasonic therapy to a thermal treatment zone at a focal depth. In an embodiment, the reduction of focal gain reduces a peak such that a variance around the focal depth is reduced by 25-100% (e.g., 30-50, 45-75, 50-90%, and any values therein). In an embodiment, the reduction of focal gain reduces a peak such that a variance of an intensity around the focal depth is 5 mm or less (e.g., 1, 2, 3, 4 mm or less). In an embodiment, the reduction of focal gain reduces a variance in focal gain in a range of 0.01-10 (e.g., 0.06, 3, 4.5, 8, or any values therein). In an embodiment, the electrical conductor is a metal. In an embodiment, the first surface is a concave surface and the second surface is a convex surface. In an embodiment, the first surface is a convex surface and the second surface is a concave surface. In an embodiment, the cylindrical transduction element is housed within an ultrasonic hand-held probe, wherein the ultrasonic probe includes a housing, the cylindrical transduction element, and a motion mechanism, wherein the ultrasound transducer is movable within the housing, wherein the motion mechanism is attached to the ultrasound transducer and configured to move the ultrasound transducer along a linear path within the housing. In an embodiment, the motion mechanism automatically moves the cylindrical transduction element to heat a treatment area at the focal depth to a temperature in a range between 40-65 degrees Celsius. In an embodiment, the cylindrical transduction element produces a temperature in a range of 42-55 degrees Celsius in a tissue at the focal depth. In an embodiment, the method also includes imaging tissue with one or more imaging elements, wherein the cylindrical transduction element has an opening configured for placement of the one or more imaging elements. In an embodiment, the method also includes confirming a level of acoustic coupling between the system and a skin surface with an image from the imaging element. In an embodiment, the method also includes confirming a level of acoustic coupling between the system and a skin surface with the imaging element using any one of the group consisting of: defocused imaging and Voltage Standing Wave Ratio (VSWR). In an embodiment, the method also includes measuring a temperature at a target tissue at the focal depth below a skin surface with the imaging element. In an embodiment, the method also includes measuring a temperature with the imaging element at a target tissue at the focal depth below a skin surface with any one of the group of Acoustic Radiation Force Impulse (ARFI), Shear Wave Elasticity Imaging (SWEI), and measurement of attenuation.

The methods summarized above and set forth in further detail below describe certain actions taken by a practitioner; however, it should be understood that they can also include the instruction of those actions by another party. Thus, actions such as "applying an ultrasound energy" include "instructing the application of ultrasound energy."

Further, areas of applicability will become apparent from the description provided herein. It should be understood that the description and specific examples are intended for purposes of illustration only and are not intended to limit the scope of the embodiments disclosed herein.

BRIEF DESCRIPTION OF THE DRAWINGS

The drawings described herein are for illustration purposes only and are not intended to limit the scope of the present disclosure in any way. Embodiments of the present invention will become more fully understood from the detailed description and the accompanying drawings wherein:

FIG. 41 is a table listing isoeffective dosages to theoretically achieve 1% survival fraction in tissue, listing temperature and time, according to an embodiment of the present invention.

FIG. 47 is a chart for setting for an isoeffective dosage study according to an embodiment of the present invention.

FIG. 49 is a table with target temperatures and time for a treatment study according to an embodiment of the present invention.

FIG. 50 is a table with various embodiments of transducers treatments settings for an isoeffective thermal dosage treatment study according to an embodiment of the present invention.

FIG. 58 is a chart illustrating velocity and position along an axis according to an embodiment of the present invention.

FIG. 59 illustrates a non-overlapping treatment according to an embodiment of the present invention.

FIG. 60 illustrates a partially overlapping and a partially non-overlapping treatment according to an embodiment of the present invention.

DETAILED DESCRIPTION

Figure 1:
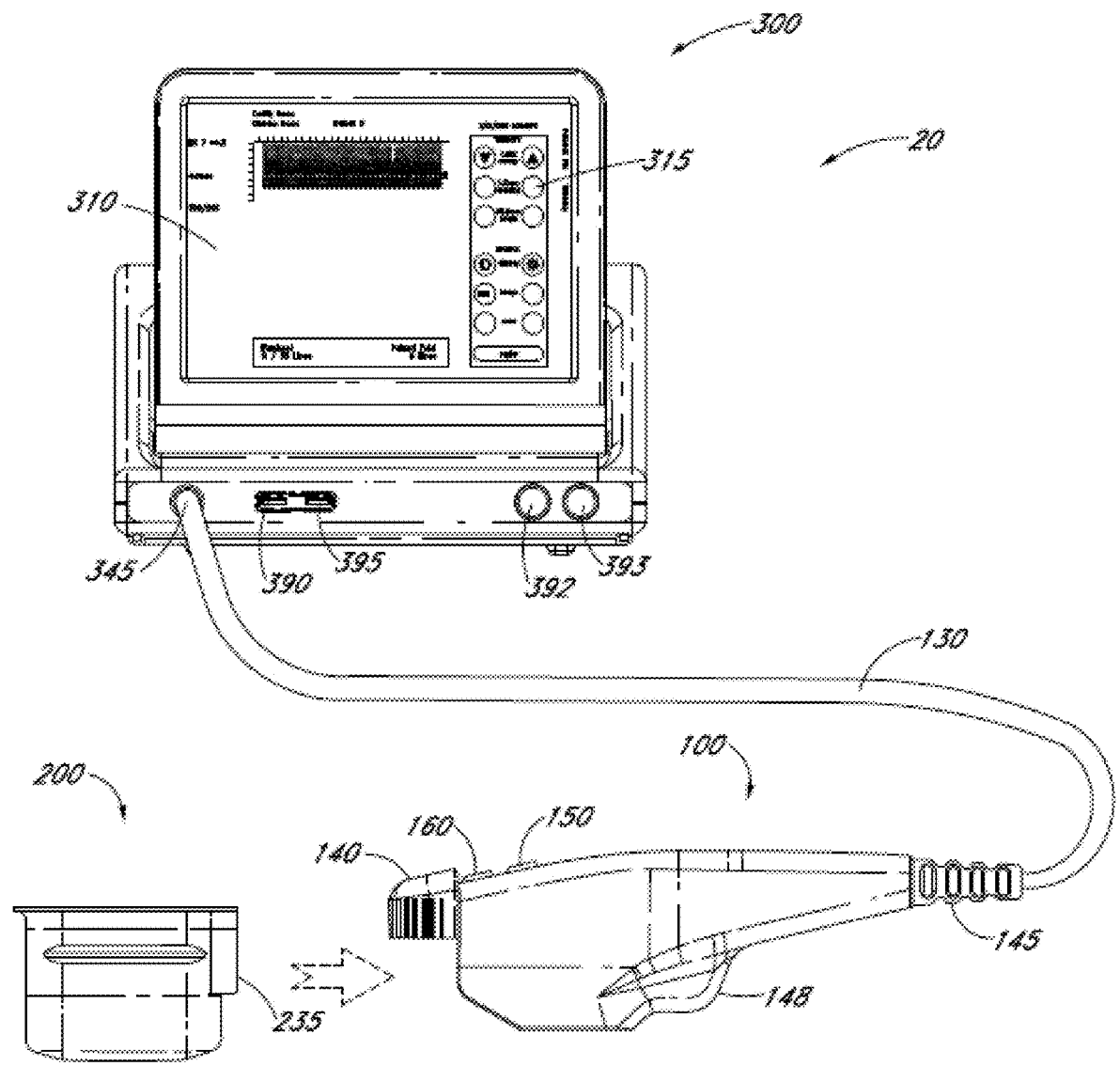
FIG. 1 is a schematic illustration of an ultrasound system according to various embodiments of the present invention.

The following description sets forth examples of embodiments, and is not intended to limit the present invention or its teachings, applications, or uses thereof. It should be understood that throughout the drawings, corresponding reference numerals indicate like or corresponding parts and features. The description of specific examples indicated in various embodiments of the present invention are intended for purposes of illustration only and are not intended to limit the scope of the invention disclosed herein. Moreover, recitation of multiple embodiments having stated features is not intended to exclude other embodiments having additional features or other embodiments incorporating different combinations of the stated features. Further, features in one embodiment (such as in one figure) may be combined with descriptions (and figures) of other embodiments.

In various embodiments, systems and methods for ultrasound treatment of tissue are configured to provide cosmetic treatment. Various embodiments of the present invention address potential challenges posed by administration of ultrasound therapy. In various embodiments, the amount of time and/or energy to create a thermal treatment zone (also referred to herein "TTZ") for a desired cosmetic and/or therapeutic treatment for a desired clinical approach at a target tissue is reduced. In various embodiments, tissue below or at a skin surface such as epidermis, dermis, platysma, lymph node, nerve, fascia, muscle, fat, and/or superficial muscular aponeurotic system ("SMAS"), are treated non-invasively with ultrasound energy. In various embodiments, tissue below or at a skin surface such as epidermis, dermis, platysma, lymph node, nerve, fascia, muscle, fat, and/or SMAS are not treated. The ultrasound energy can be focused at one or more treatment zones, can be unfocused and/or defocused, and can be applied to a region of interest to achieve a cosmetic and/or therapeutic effect. In various embodiments, systems and/or methods provide non-invasive dermatological treatment to tissue through heating, thermal treatment, coagulation, ablation, and/or tissue tightening (including, for example, hyperthermia, thermal dosimetry, apoptosis, and lysis). In one embodiment, dermal tissue volume is increased. In one embodiment, fat tissue volume is reduced, or decreased.

In various embodiments, target tissue is, but is not limited to, any of skin, eyelids, eye lash, eye brow, caruncula lacrimalis, crow's feet, wrinkles, eye, nose, mouth, tongue, teeth, gums, ears, brain, chest, back, buttocks, legs, arms, hands, arm pits, heart, lungs, ribs, abdomen, stomach, liver, kidneys, uterus, breast, vagina, penis, prostate, testicles, glands, thyroid glands, internal organs, hair, muscle, bone, ligaments, cartilage, fat, fat lobuli, adipose tissue, cellulite, subcutaneous tissue, implanted tissue, an implanted organ, lymphoid, a tumor, a cyst, an abscess, or a portion of a nerve, or any combination thereof. In several embodiments disclosed herein, non-invasive ultrasound is used to achieve one or more of the following effects: a face lift, a brow lift, a chin lift, an eye treatment, a wrinkle reduction, a scar reduction, a fat reduction, a reduction in the appearance of cellulite, a décolletage treatment, a burn treatment, a tattoo removal, a vein reduction, a treatment on a sweat gland, a treatment of hyperhidrosis, sun spot removal, an acne treatment, and a pimple removal. In some embodiments, two, three or more beneficial effects are achieved during the same treatment session, and may be achieved simultaneously.

Various embodiments of the present invention relate to devices or methods of controlling the delivery of energy to tissue. In various embodiments, various forms of energy can include acoustic, ultrasound, light, laser, radio-frequency (RF), microwave, electromagnetic, radiation, thermal, cryogenic, electron beam, photon-based, magnetic, magnetic resonance, and/or other energy forms. Various embodiments of the present invention relate to devices or methods of splitting an ultrasonic energy beam into multiple beams. In various embodiments, devices or methods can be used to alter the delivery of ultrasound acoustic energy in any procedures such as, but not limited to, therapeutic ultrasound, diagnostic ultrasound, non-destructive testing (NDT) using ultrasound, ultrasonic welding, any application that involves coupling mechanical waves to an object, and other procedures. Generally, with therapeutic ultrasound, a tissue effect is achieved by concentrating the acoustic energy using focusing techniques from the aperture. In some instances, high intensity focused ultrasound (HIFU) is used for therapeutic purposes in this manner. In one embodiment, a tissue effect created by application of therapeutic ultrasound at a particular location (e.g., depth, width) to can be referred to as creation of a thermal treatment zone. It is through creation of thermal treatment zones at particular positions that thermal and/or mechanical heating, coagulation, and/or ablation of tissue can occur non-invasively or remotely offset from the skin surface.

System Overview

Various embodiments of ultrasound treatment and/or imaging devices are described in U.S. Publication No. 2011-0112405, which is a national phase publication from International Publication WO 2009/149390, each of which is incorporated in its entirety by reference herein.

With reference to the illustration in FIG. 1, an embodiment of an ultrasound system 20 includes a hand wand 100, module 200, and a controller 300. The hand wand 100 can be coupled to the controller 300 by an interface 130, which may be a wired or wireless interface. The interface 130 can be coupled to the hand wand 100 by a connector 145. The distal end of the interface 130 can be connected to a controller connector on a circuit 345. In one embodiment, the interface 130 can transmit controllable power from the controller 300 to the hand wand 100. In various embodiments, the controller 300 can be configured for operation with the hand wand 100 and the module 200, as well as the overall ultrasound system 20 functionality. In various embodiments, a controller 300 is configured for operation with a hand wand 100 with one or more removable modules 200, 200', 200", etc. The controller 300 can include an interactive graphical display 310, which can include a touchscreen monitor and Graphic User Interface (GUI) that allows the user to interact with the ultrasound system 20. As is illustrated, the graphical display 315 includes a touchscreen interface 315. In various embodiments, the display 310 sets and displays the operating conditions, including equipment activation status, treatment parameters, system messages and prompts, and ultrasound images. In various embodiments, the controller 300 can be configured to include, for example, a microprocessor with software and input/output devices, systems and devices for controlling electronic and/or mechanical scanning and/or multiplexing of transducers and/or multiplexing of transducer modules, a system for power delivery, systems for monitoring, systems for sensing the spatial position of the probe and/or transducers and/or multiplexing of transducer modules, and/or systems for handling user input and recording treatment results, among others. In various embodiments, the controller 300 can include a system processor and various analog and/or digital control logic, such as one or more of microcontrollers, microprocessors, field-programmable gate arrays, computer boards, and associated components, including firmware and control software, which may be capable of interfacing with user controls and interfacing circuits as well as input/output circuits and systems for communications, displays, interfacing, storage, documentation, and other useful functions. System software running on the system process may be configured to control all initialization, timing, level setting, monitoring, safety monitoring, and all other ultrasound system functions for accomplishing user-defined treatment objectives. Further, the controller 300 can include various input/output modules, such as switches, buttons, etc., that may also be suitably configured to control operation of the ultrasound system 20. In one embodiment, the controller 300 can include one or more data ports 390. In various embodiments, the data ports 390 can be a USB port, Bluetooth port, IrDA port, parallel port, serial port, and the like. The data ports 390 can be located on the front, side, and/or back of the controller 300, and can be used for accessing storage devices, printing devices, computing devices, etc. The ultrasound system 20 can include a lock 395. In one embodiment, in order to operate the ultrasound system 20, the lock 395 should be unlocked so that a power switch 393 may be activated. In one embodiment, the lock 395 can be connectable to the controller 300 via a data port 390 (e.g., a USB port). The lock 395 could be unlocked by inserting into the data port 390 an access key (e.g., USB access key), a hardware dongle, or the like. The controller 300 can include an emergency stop button 392, which can be readily accessible for emergency deactivation.

As is illustrated in FIG. 1, in one embodiment, the hand wand 100 includes one or more finger activated controllers or switches, such as 150 and 160. In one embodiment, the hand wand 100 can include a removable module 200. In other embodiments, the module 200 may be non-removable. The module 200 can be mechanically coupled to the hand wand 100 using a latch or coupler 140. An interface guide 235 can be used for assisting the coupling of the module 200 to the hand wand 100. The module 200 can include one or more ultrasound transducers 280. In some embodiments, an ultrasound transducer 280 includes one or more ultrasound elements 281. The module 200 can include one or more ultrasound elements 281. The elements 281 can be therapy elements, and/or imaging elements. The hand wand 100 can include imaging-only modules 200, treatment-only modules 200, imaging-and-treatment modules 200, and the like. In one embodiment, the imaging is provided through the hand wand 100. In one embodiment, the control module 300 can be coupled to the hand wand 100 via the interface 130, and the graphic user interface 310 can be configured for controlling the module 200. In one embodiment, the control module 300 can provide power to the hand wand 100. In one embodiment, the hand wand 100 can include a power source. In one embodiment, the switch 150 can be configured for controlling a tissue imaging function and the switch 160 can be configured for controlling a tissue treatment function In one embodiment, the module 200 can be coupled to the hand wand 100. The module 200 can emit and receive energy, such as ultrasonic energy. The module 200 can be electronically coupled to the hand wand 100 and such coupling may include an interface which is in communication with the controller 300. In one embodiment, the interface guide 235 can be configured to provide electronic communication between the module 200 and the hand wand 100. The module 200 can comprise various probe and/or transducer configurations. For example, the module 200 can be configured for a combined dual-mode imaging/therapy transducer, coupled or co-housed imaging/therapy transducers, separate therapy and imaging probes, and the like. In one embodiment, when the module 200 is inserted into or connected to the hand wand 100, the controller 300 automatically detects it and updates the interactive graphical display 310.

Figure 2:
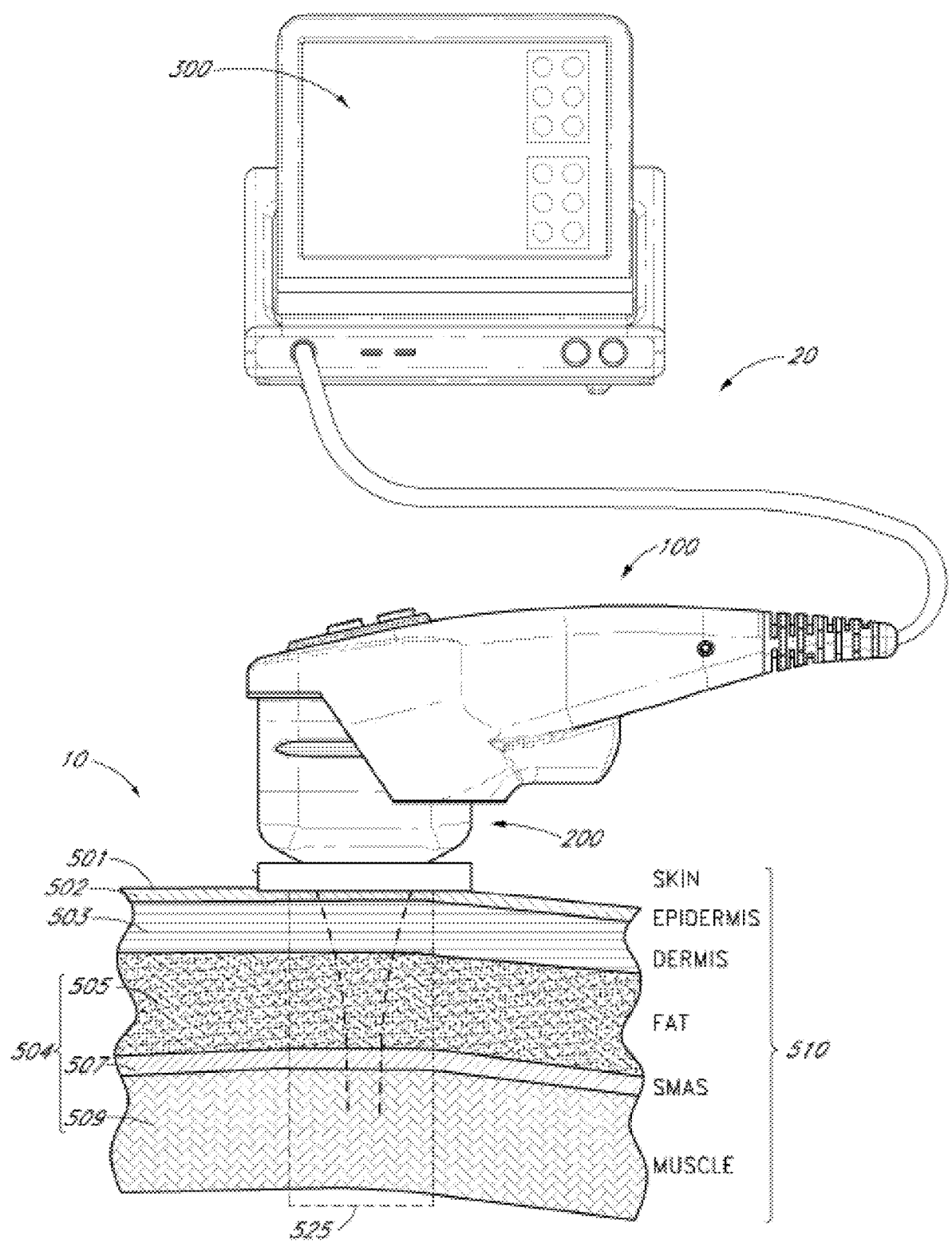
FIG. 2 is a schematic illustration of an ultrasound system coupled to a region of interest according to various embodiments of the present invention.

In various embodiments, tissue below or even at a skin surface such as epidermis, dermis, hypodermis, fascia, and SMAS, and/or muscle are treated non-invasively with ultrasound energy. Tissue may also include blood vessels and/or nerves. The ultrasound energy can be focused, unfocused or defocused and applied to a region of interest containing at least one of epidermis, dermis, hypodermis, fascia, and SMAS to achieve a therapeutic effect. FIG. 2 is a schematic illustration of the ultrasound system 20 coupled to a region of interest 10, such as with an acoustic gel. With reference to the illustration in FIG. 2, an embodiment of the ultrasound system 20 includes the hand wand 100, the module 200, and the controller 300. In various embodiments, tissue layers of the region of interest 10 can be at any part of the body of a subject. In various embodiments, the tissue layers are in the head, face, neck and/or body region of the subject. The cross-sectional portion of the tissue of the region of interest 10 includes a skin surface 501, an epidermal layer 502, a dermal layer 503, a fat layer 505, a SMAS 507, and a muscle layer 509. The tissue can also include the hypodermis 504, which can include any tissue below the dermal layer 503. The combination of these layers in total may be known as subcutaneous tissue 510. Also illustrated in FIG. 2 is a treatment zone 525 which is the active treatment area below the surface 501. In one embodiment, the surface 501 can be a surface of the skin of a subject 500. Although an embodiment directed to therapy at a tissue layer may be used herein as an example, the system can be applied to any tissue in the body. In various embodiments, the system and/or methods may be used on muscles (or other tissue) of the face, neck, head, arms, legs, or any other location in the body. In various embodiments, the therapy can be applied to a face, head, neck, submental region, shoulder, arm, back, chest, buttock, abdomen, stomach, waist, flank, leg, thigh, or any other location in or on the body.

Band Therapy Using a Cylindrical Transducer

In various embodiments, a transducer 280 can comprise one or more therapy elements 281 that can have various shapes that correspond to various focal zone geometries. In one embodiment, the transducer 280 comprises a single therapy element 281. In one embodiment, the transducer 280 does not have a plurality of elements. In one embodiment, the transducer 280 does not have an array of elements. In several embodiments, the transducers 280 and/or therapy elements 281 described herein can be flat, round, circular, cylindrical, annular, have rings, concave, convex, contoured, and/or have any shape. In some embodiments, the transducers 280 and/or therapy elements 281 described herein are not flat, round, circular, cylindrical, annular, have rings, concave, convex, and/or contoured. In one embodiment, the transducers 280 and/or therapy elements 281 have a mechanical focus. In one embodiment, the transducers 280 and/or therapy elements 281 do not have a mechanical focus. In one embodiment, the transducers 280 and/or therapy elements 281 have an electrical focus. In one embodiment, the transducers 280 and/or therapy elements 281 do not have an electrical focus. Although a cylinder transducer and/or a cylindrical element is discussed here, the transducer and/or element need not be cylindrical. In several embodiments, the transducer and/or element has one or more shapes or configurations that cause edge effects, such as variance, spikes or other inconsistencies in the delivery of ultrasound. For example, the transducer and/or element may have one or more non-linear (e.g., curved) portions. A transducer may be comprised of one or more individual transducers and/or elements in any combination of focused, planar, or unfocused single-element, multi-element, or array transducers, including 1-D, 2-D, and annular arrays; linear, curvilinear, sector, or spherical arrays; spherically, cylindrically, and/or electronically focused, defocused, and/or lensed sources. In one embodiment, the transducer is not a multi-element transducer. In one embodiment, a transducer 280 can include a spherically shaped bowl with a diameter and one or more concave surfaces (with respective radii or diameters) geometrically focused to a single point TTZ 550 at a focal depth 278 below a tissue surface, such as skin surface 501. In one embodiment, a transducer 280 may be radially symmetrical in three dimensions. For example, in one embodiment, transducer 280 may be a radially symmetrical bowl that is configured to produce a focus point in a single point in space. In some embodiments, the transducer is not spherically shaped. In some embodiments, the element is not spherically shaped.

In various embodiments, increasing the size (e.g. width, depth, area) and/or number of focus zone locations for an ultrasonic procedure can be advantageous because it permits treatment of a patient at varied tissue widths, heights and/or depths even if the focal depth 278 of a transducer 280 is fixed. This can provide synergistic results and maximizing the clinical results of a single treatment session. For example, treatment at larger treatment areas under a single surface region permits a larger overall volume of tissue treatment, which can heat larger tissue volumes, and which can result in enhanced collagen formation and tightening. Additionally, larger treatment areas, such as at different depths, affects different types of tissue, thereby producing different clinical effects that together provide an enhanced overall cosmetic result. For example, superficial treatment may reduce the visibility of wrinkles and deeper treatment may induce skin tightening and/or collagen growth. Likewise, treatment at various locations at the same or different depths can improve a treatment. In various embodiments, a larger treatment area can be accomplished using a transducer with a larger focus zones (e.g., such as a linear focus zone compared to a point focus zone).

Figure 3:
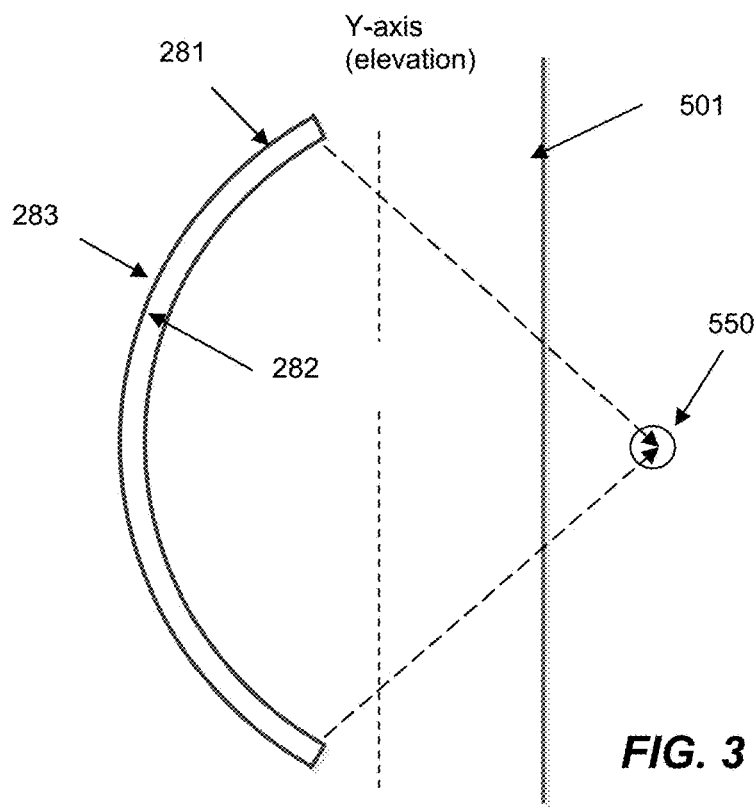
FIG. 3 illustrates a schematic cross-sectional side view of a cylindrical transducer in a cosmetic treatment system according to an embodiment. Although a cylinder transducer is illustrated here, the transducer need not be cylindrical. In several embodiments, the transducer has one or more shapes or configurations that cause edge effects, such as variance, spikes or other inconsistencies in the delivery of ultrasound. For example, the transducer may have one or more non-linear (e.g., curved) portions.
Figure 4:
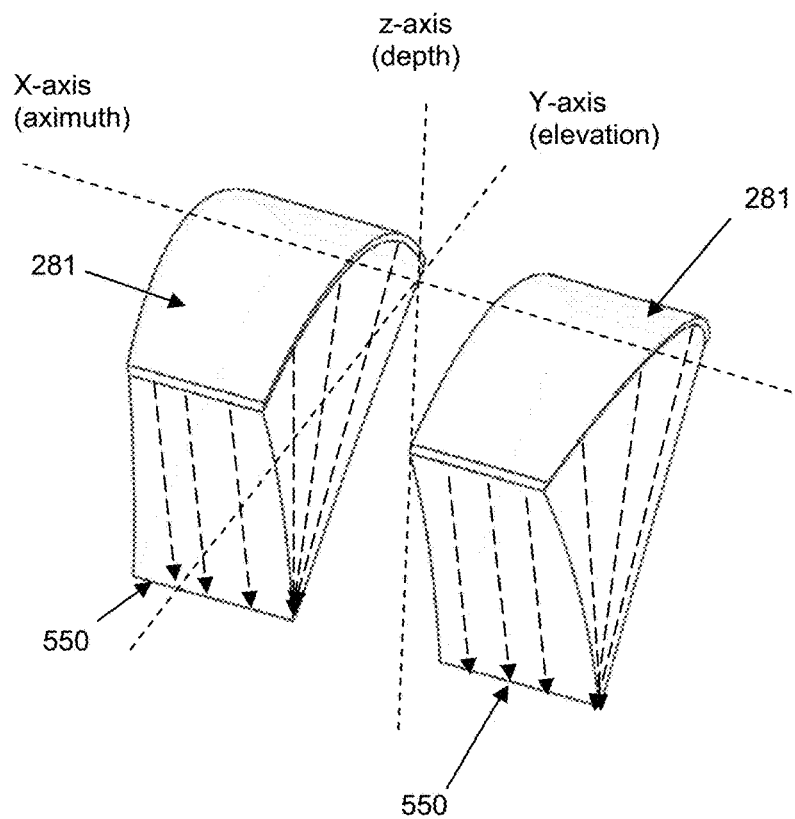
FIG. 4 illustrates a schematic isometric side view of a sectioned cylindrical transducer of FIG. 3.
Figure 5A:
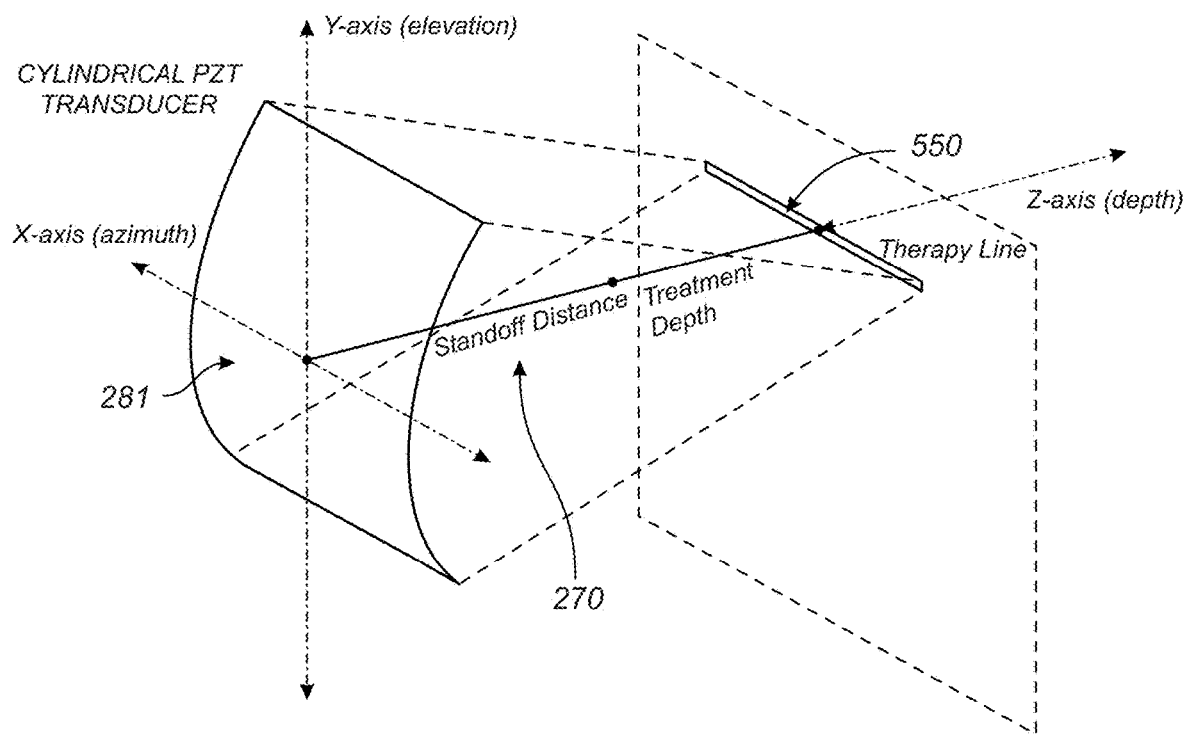
FIGS. 5A-5B illustrate a schematic isometric side view of a cylindrical transducer being moved by a motion mechanism in a cosmetic treatment system, wherein the thermal treatment zone (TTZ) sweeps a treatment area, according to an embodiment.
Figure 5B:
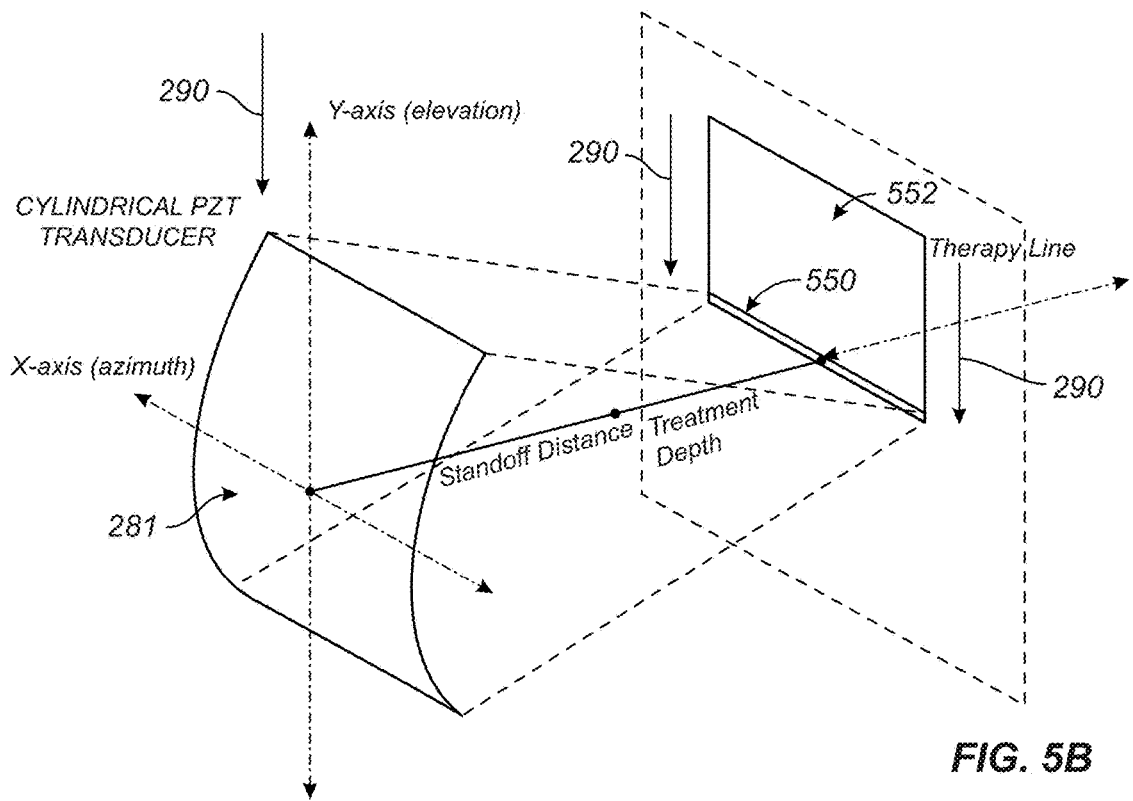

In one embodiment, as illustrated in FIGS. 3 and 4, a transducer 280 comprises a cylindrical transduction element 281. In FIG. 4, the view of the cylindrical transduction element 281, which has a concave surface 282 and a convex surface 283, is sectioned to show energy emission from the concave surface to a linear TTZ 550. The cylindrical transduction element 281 extends linearly along its longitudinal axis (X-axis, azimuth) with a curved cross section along a Y-axis (elevation). In one embodiment, the cylindrical surface has a radius at a focal depth (z-axis) at the center of the curvature of the cylindrical surface, such that the TTZ 550 is focused at the center of the radius. For example, in one embodiment, cylindrical transduction element 281 has a concave surface that extends like a cylinder that produces a focus zone that extends along a line, such as a therapy line, such as TTZ 550. The focus zone TTZ 550 extends along the width (along the X-axis, azimuth) of the cylindrical transduction element 281, in a line parallel to the longitudinal axis of the cylindrical transduction element 281. As illustrated in FIG. 3, the TTZ 550 is a line extending in and/or out of the page. In various embodiments of the cylindrical transduction element 281, a concave surface directs ultrasound energy to a linear TTZ 550. Cylindrical transduction element 281 need not be cylindrical; in some embodiments, element 281 is a transduction element having one or more curved or non-linear portions.

In various embodiments, transducers 280 can comprise one or more transduction elements 281. The transduction elements 281 can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In various embodiments, in addition to, or instead of, a piezoelectrically active material, transducers can comprise any other materials configured for generating radiation and/or acoustical energy. In one embodiment, when cylindrical transduction element 281 comprises a piezoelectric ceramic material that is excited by an electrical stimulus, the material may expand or contract. The amount of expansion or contraction is related to boundary conditions in the ceramic as well as the magnitude of the electric field created in the ceramic. In some embodiments of conventional HIFU design, the front surface (e.g. subject side) is coupled to water and the back surface of a transducer 280 is coupled to a low impedance medium which is typically air. In some embodiments, although the ceramic is free to expand at the back interface, essentially no mechanical energy is coupled from the ceramic to the air because of the significant acoustic impedance disparity. This results in this energy at the back of the ceramic reflecting and exiting the front (or subject side) surface. As illustrated in an embodiment in FIGS. 3-5B, the focus is created by forming, casting, and/or machining the ceramic to the correct radius-of-curvature. In one embodiment, a flat transducer material is bent to form a cylindrical transducer. In various embodiments, transducers 280 and/or therapy elements 281 can be configured to operate at different frequencies and treatment depths. Transducer properties can be defined by a focal length ($F_L$), sometimes referred to as a focal depth 278. The focal depth 278 is the distance from the concave cylindrical surface to the focal zone TTZ 550. In various embodiments, the focal depth 278 is the sum of a standoff distance 270 and a treatment depth 279 when the housing of a probe is placed against a skin surface. In one embodiment, the standoff distance 270, or offset distance 270, is the distance between the transducer 280 and a surface of an acoustically transparent member 230 on the housing of a probe. The treatment depth 279 is a tissue depth 279 below a skin surface 501, to a target tissue. In one embodiment, the height of the aperture in the curved dimension is increased or maximized to have a direct effect on overall focal gain, which correlates to the ability to heat tissue. For example, in one embodiment, the height of the aperture in the curved dimension is maximized for a treatment depth of 6 mm or less. In one embodiment, as the aperture is increased (e.g. decreasing the f#), the actual heating zone gets closer to the surface.

In one embodiment, a transducer can be configured to have a focal depth 278 of 6 mm, 2-12 mm, 3-10 mm, 4-8 mm, 5-7 mm. In other embodiments, other suitable values of focal depth 278 can be used, such as focal depth 278 of less than about 15 mm, greater than about 15 mm, 5-25 mm, 10-20 mm, etc. Transducer modules can be configured to apply ultrasonic energy at different target tissue depths. In one embodiment, a therapy of 20 mm or less (e.g., 0.1 mm-20 mm, 5-17 mm, 10-15 mm). In one embodiment, a devices that goes to 6 mm or less has a radius of curvature (ROC) of 13.6 mm, with a ratio of treatment depth to ROC at approximately 44%. In one embodiment, the height of the element is 22 mm. In one embodiment, using an aspect ratio for a treatment depth of 20 mm, the aperture height would be 74.5 mm with a ROC of 45 mm.

As illustrated in FIGS. 5A-5B, 7, 9 and 10 in several embodiments, a system may comprise a movement mechanism 285 configured to move a transducer 280 comprising a cylindrical transduction element 281 in one, two, three or more directions. In one embodiment, a motion mechanism 285 can move in a linear direction, one or both ways, denoted by the arrow marked 290 in order move a TTZ 550 through tissue. In various embodiments, the motion mechanism 285 can move the transducer in one, two, and/or three linear dimensions and/or one, two, and/or three rotational dimensions. In one embodiment, a motion mechanism 285 can move in up to six degrees of freedom. Movement of the TTZ 550 can be with the transducer continuously delivering energy to create a treatment area 552. In one embodiment, a movement mechanism 285 can automatically move the cylindrical transduction element 281 across the surface of a treatment area so that the TTZ 550 can form a treatment area 552.

Figure 6:
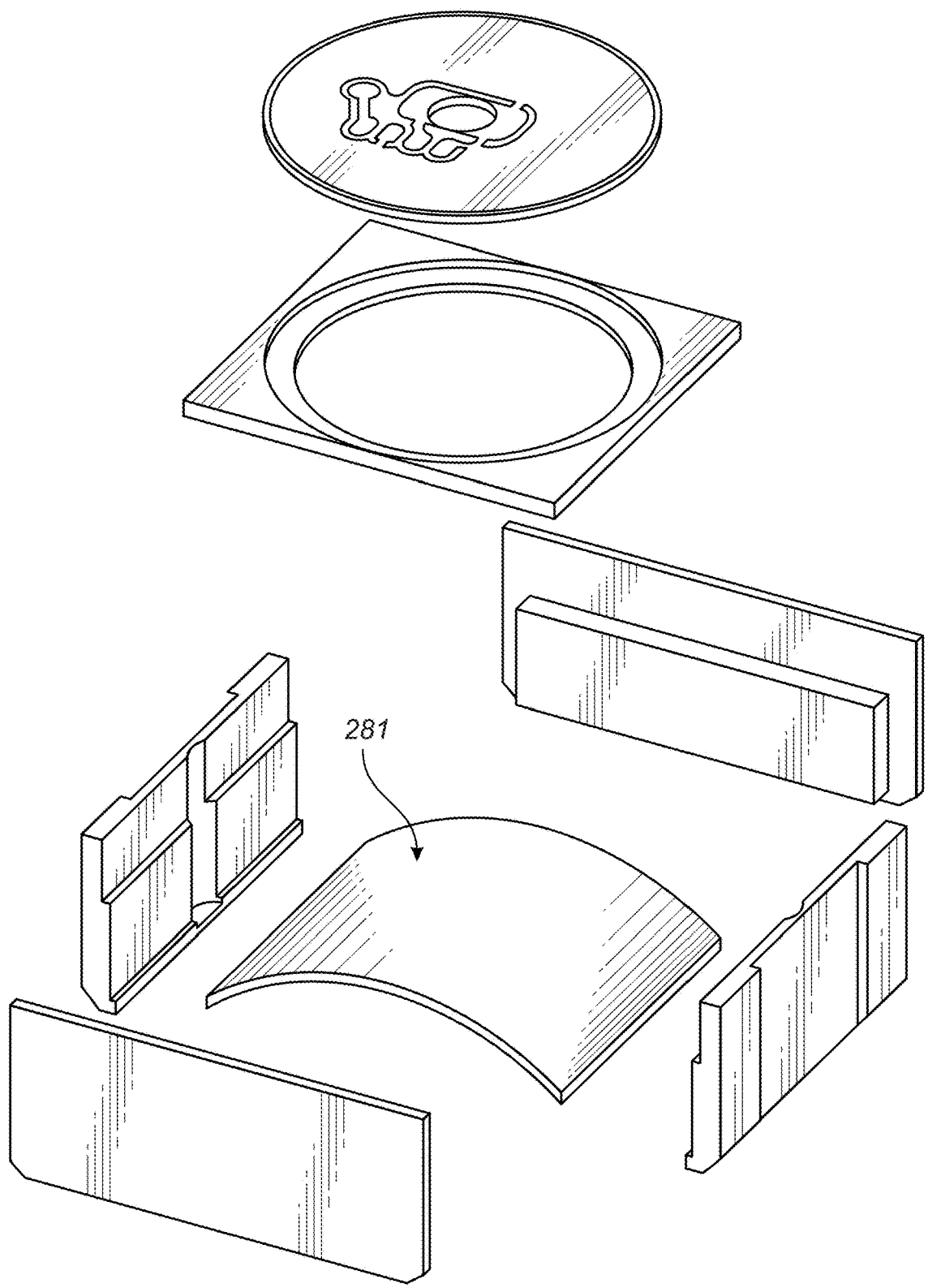
FIG. 6 illustrates a schematic exploded isometric view of a cylindrical transduction element in a cosmetic treatment system according to an embodiment.
Figure 7:
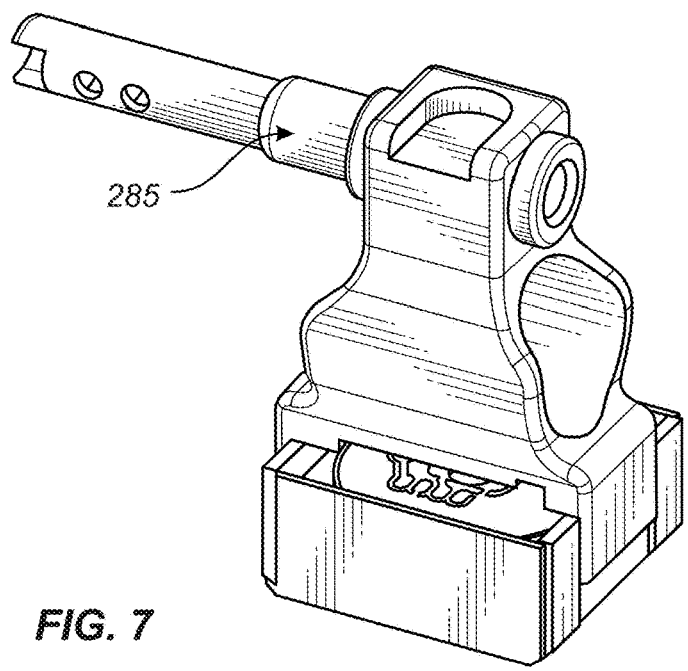
FIG. 7 illustrates a schematic isometric view of the cylindrical transduction element of FIG. 6 with a motion mechanism in a cosmetic treatment system according to an embodiment.
Figure 8:
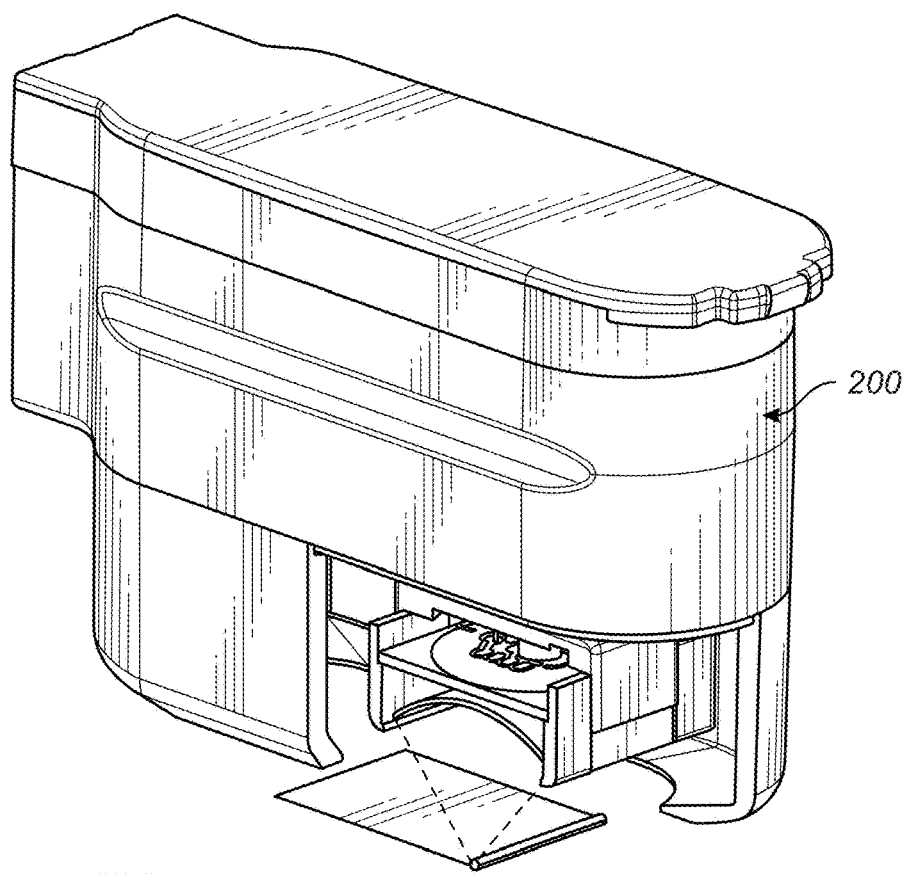
FIG. 8 illustrates a schematic isometric view of the cylindrical transduction element with a motion mechanism of FIG. 7 in a probe housing of a cosmetic treatment system according to an embodiment.

As indicated in FIGS. 6, 7, and 8, a cylindrical transduction element 281 can be connected to a motion mechanism 285 and placed inside a module 200 or a probe. In various embodiments, a movement mechanism 285, or a motion mechanism 285, moves the transducer 280 and/or treatment element 281 such that the corresponding TTZ 550 moves to treat a larger treatment area 552. In various embodiments, a movement mechanism 285 is configured to move a transducer within a module or a probe. In one embodiment, a transducer is held by a transducer holder. In one embodiment, the transducer holder includes a sleeve which is moved along motion constraining bearings, such as linear bearings, namely, a bar (or shaft) to ensure a repeatable linear movement of the transducer. In one embodiment, sleeve is a spline bushing which prevents rotation about a spline shaft, but any guide to maintain the path of motion is appropriate. In one embodiment, the transducer holder is driven by a motion mechanism 285, which may be located in a hand wand or in a module, or in a probe. In one embodiment, a motion mechanism 285 includes any one or more of a scotch yoke, a movement member, and a magnetic coupling. In one embodiment, the magnetic coupling helps move the transducer. One benefit of a motion mechanism 285 is that it provides for a more efficient, accurate and precise use of an ultrasound transducer, for imaging and/or therapy purposes. One advantage this type of motion mechanism has over conventional fixed arrays of multiple transducers fixed in space in a housing is that the fixed arrays are a fixed distance apart. By placing transducer on a track (e.g., such as a linear track) under controller control, embodiments of the system and device provide for adaptability and flexibility in addition to efficiency, accuracy and precision.

Real time and near real time adjustments can be made to imaging and treatment positioning along the controlled motion by the motion mechanism 285. In addition to the ability to select nearly any resolution based on the incremental adjustments made possible by the motion mechanism 285, adjustments can be made if imaging detects abnormalities or conditions meriting a change in treatment spacing and targeting. In one embodiment, one or more sensors may be included in the module. In one embodiment, one or more sensors may be included in the module to ensure that a mechanical coupling between the movement member and the transducer holder is indeed coupled. In one embodiment, an encoder may be positioned on top of the transducer holder and a sensor may be located in a portion of the module, or vice versa (swapped). In various embodiments the sensor is a magnetic sensor, such as a giant magnetoresistive effect (GMR) or Hall Effect sensor, and the encoder a magnet, collection of magnets, or multi-pole magnetic strip. The sensor may be positioned as a transducer module home position. In one embodiment, the sensor is a contact pressure sensor. In one embodiment, the sensor is a contact pressure sensor on a surface of the device to sense the position of the device or the transducer on the patient. In various embodiments, the sensor can be used to map the position of the device or a component in the device in one, two, or three dimensions. In one embodiment the sensor is configured to sense the position, angle, tilt, orientation, placement, elevation, or other relationship between the device (or a component therein) and the patient. In one embodiment, the sensor comprises an optical sensor. In one embodiment, the sensor comprises a roller ball sensor. In one embodiment, the sensor is configured to map a position in one, two and/or three dimensions to compute a distance between areas or lines of treatment on the skin or tissue on a patient.

In various embodiments, a motion mechanism 285 can be any mechanism that may be found to be useful for movement of the transducer. In one embodiment, the motion mechanism 285 comprises a stepper motor. In one embodiment, the motion mechanism 285 comprises a worm gear. In various embodiments, the motion mechanism 285 is located in a module 200. In various embodiments, the motion mechanism 285 is located in the hand wand 100. In various embodiments, the motion mechanism 285 can provide for linear, rotational, multi-dimensional motion or actuation, and the motion can include any collection of points, lines and/or orientations in space. Various embodiments for motion can be used in accordance with several embodiments, including but not limited to rectilinear, circular, elliptical, arc-like, spiral, a collection of one or more points in space, or any other 1-D, 2-D, or 3-D positional and attitudinal motional embodiments. The speed of the motion mechanism 285 may be fixed or may be adjustably controlled by a user. One embodiment, a speed of the motion mechanism 285 for an image sequence may be different than that for a treatment sequence. In one embodiment, the speed of the motion mechanism 285 is controllable by a controller.

In some embodiments, the energy transmitted from the transducer is turned on and off, forming a non-continuous treatment area 552 such that the TTZ 550 moves with a treatment spacing between individual TTZ 550 positions. For example, treatment spacing can be about 1 mm, 1.5 mm, 2 mm, 5 mm, 10 mm, etc. In several embodiments, a probe can further comprise a movement mechanism configured to direct ultrasonic treatment in a sequence so that TTZs 550 are formed in linear or substantially linear sequences. For example, a transducer module can be configured to form TTZs 550 along a first linear sequence and a second linear sequence separated by treatment spacing between about 2 mm and 3 mm from the first linear sequence. In one embodiment, a user can manually move the transducer modules across the surface of a treatment area so that adjacent linear sequences of TTZs are created.

In one embodiment, a TTZ can be swept from a first position to a second position. In one embodiment, a TTZ can be swept from the first position to the second position repeatedly. In one embodiment, a TTZ can be swept from the first position, to the second position, and back to the first position. In one embodiment, a TTZ can be swept from the first position, to the second position, and back to the first position, and repeated. In one embodiment, multiple sequences of TTZs can be created in a treatment region. For example, TTZs can be formed along a first linear sequence and a second linear sequence separated by a treatment distance from the first linear sequence.

Figure 9:
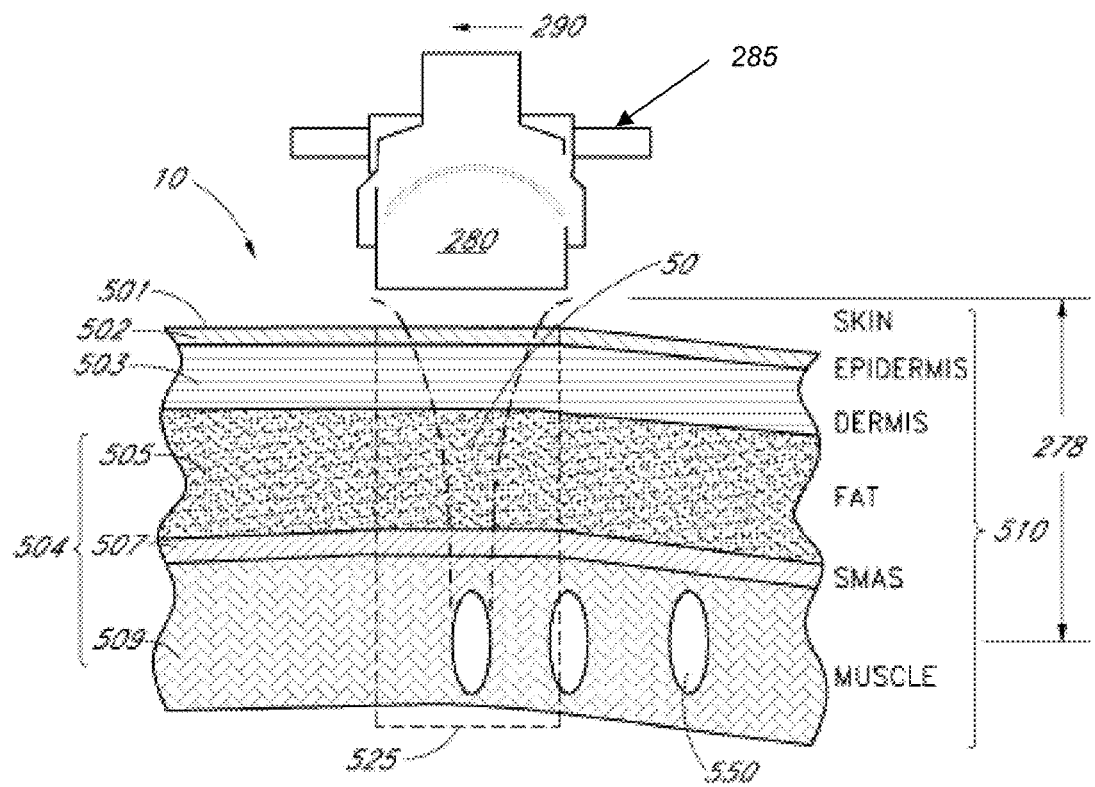
FIG. 9 is a schematic partial cut away illustration of a portion of a transducer according to various embodiments of the present invention.

In one embodiment, TTZs can be created in a linear or substantially linear zone or sequence, with each individual TTZ separated from neighboring TTZs by a treatment spacing, such as shown in FIG. 9. FIG. 9 illustrates an embodiment of an ultrasound system 20 with a transducer 280 configured to treat tissue at a focal depth 278. In one embodiment, the focal depth 278 is a distance between the transducer 280 and the target tissue for treatment. In one embodiment, a focal depth 278 is fixed for a given transducer 280. In one embodiment, a focal depth 278 is variable for a given transducer 280. As illustrated in FIG. 9, in various embodiments, delivery of emitted energy 50 at a suitable focal depth 278, distribution, timing, and energy level is provided by the module 200 through controlled operation by the control system 300 to achieve the desired therapeutic effect of controlled thermal injury to treat at least one of the epidermis layer 502, dermis layer 503, fat layer 505, the SMAS layer 507, the muscle layer 509, and/or the hypodermis 504. FIG. 9 illustrates one embodiment of a depth that corresponds to a depth for treating muscle. In various embodiments, the depth can correspond to any tissue, tissue layer, skin, epidermis, dermis, hypodermis, fat, SMAS, muscle, blood vessel, nerve, or other tissue. During operation, the module 200 and/or the transducer 280 can also be mechanically and/or electronically scanned along the surface 501 to treat an extended area. Before, during, and after the delivery of ultrasound energy 50 to at least one of the epidermis layer 502, dermis layer 503, hypodermis 504, fat layer 505, the SMAS layer 507 and/or the muscle layer 509, monitoring of the treatment area and surrounding structures can be provided to plan and assess the results and/or provide feedback to the controller 300 and the user via a graphical interface 310. In one embodiment, an ultrasound system 20 generates ultrasound energy which is directed to and focused below the surface 501. This controlled and focused ultrasound energy 50 creates the thermal treatment zone (TTZ) 550. In one embodiment, the TTZ 550 is a line. In one embodiment, the TTZ 550 is a point. In one embodiment, the TTZ 550 is a two dimensional region or plane. In one embodiment, the TTZ 550 is a volume. In one embodiment, the ultrasound energy 50 heat treats the subcutaneous tissue 510. In various embodiments, the emitted energy 50 targets the tissue below the surface 501 which heats, cuts, ablates, coagulates, micro-ablates, manipulates, and/or causes a lesion in the tissue portion 10 below the surface 501 at a specified focal depth 278. In one embodiment, during the treatment sequence, the transducer 280 moves in a direction denoted by the arrow marked 290 to move the TTZ 550.

Figure 10:
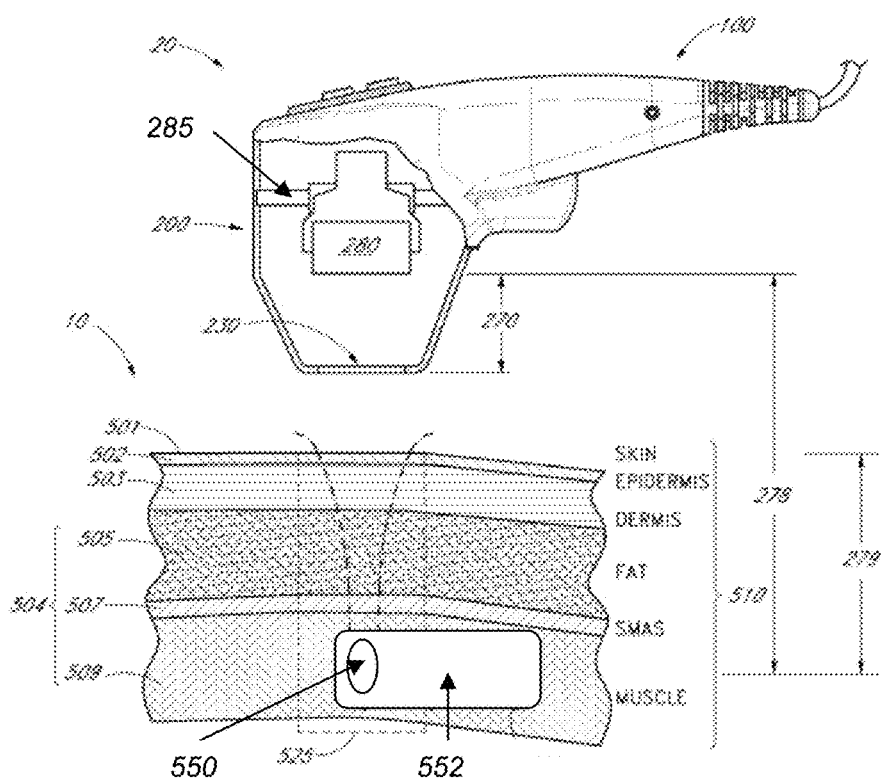
FIG. 10 is a partial cut away side view of an ultrasound system according to various embodiments of the present invention.
Figure 11A:
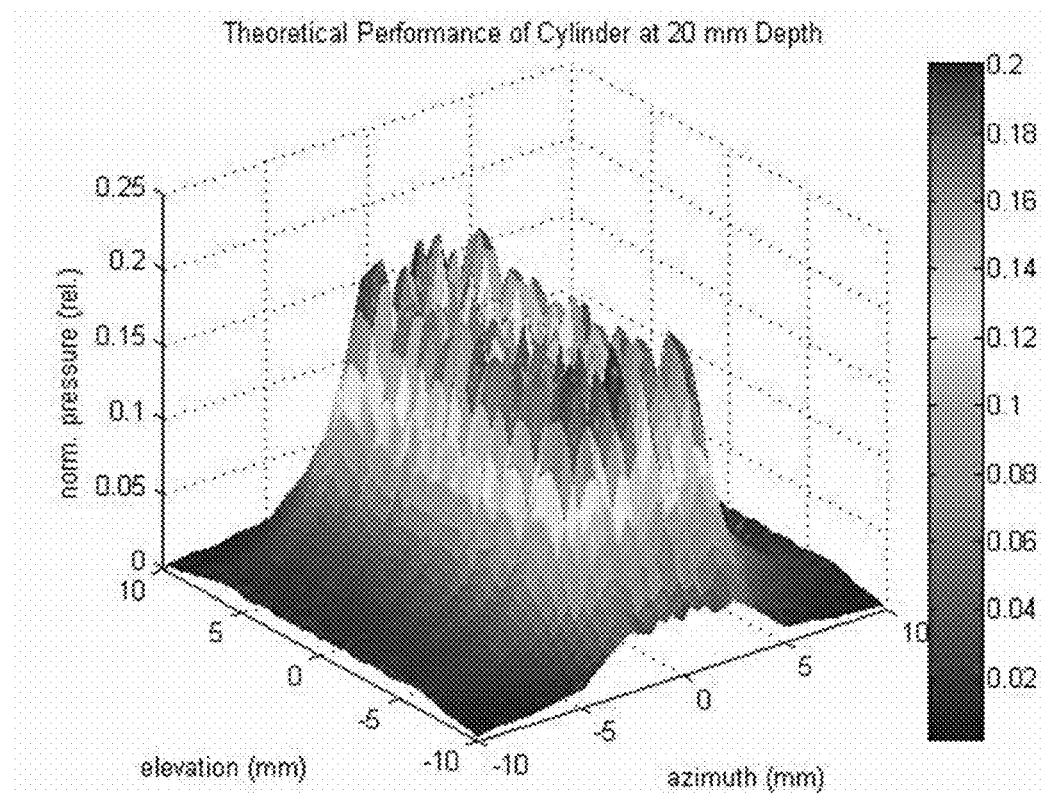
FIGS. 11A-11B are schematic illustrations and plots illustrating normalized pressure intensity distributions at a depth of 20 mm according to an embodiment of a transducer comprising a cylindrical transduction element.
Figure 11B:
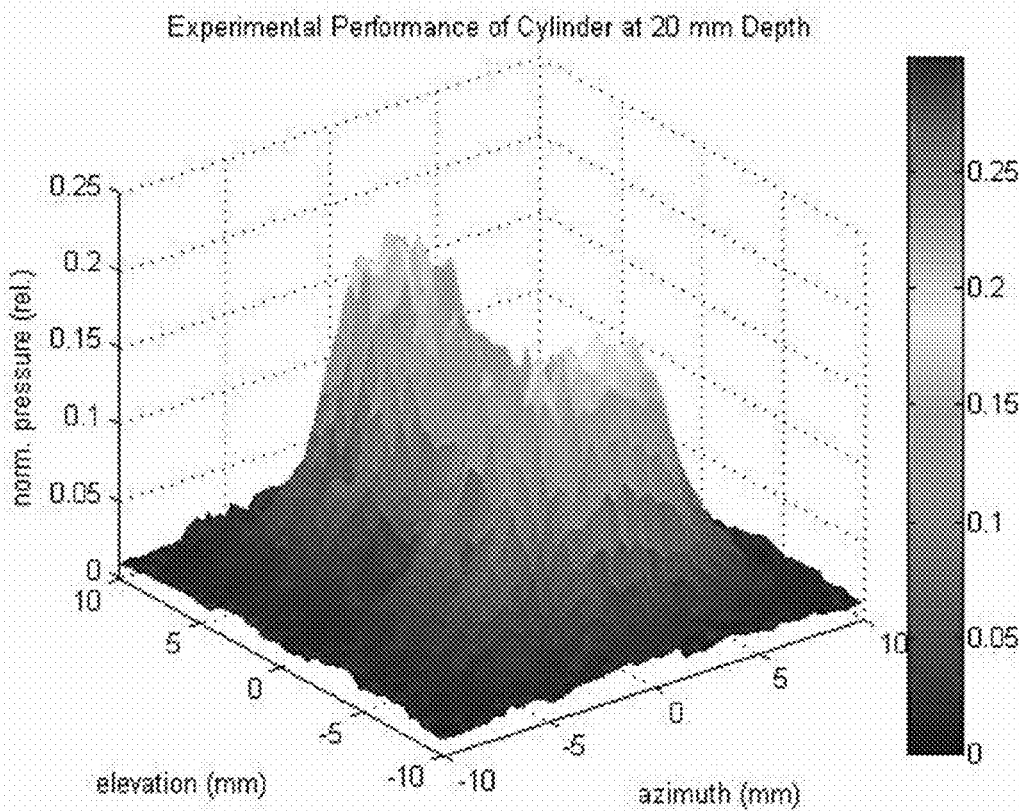
Figure 12A:
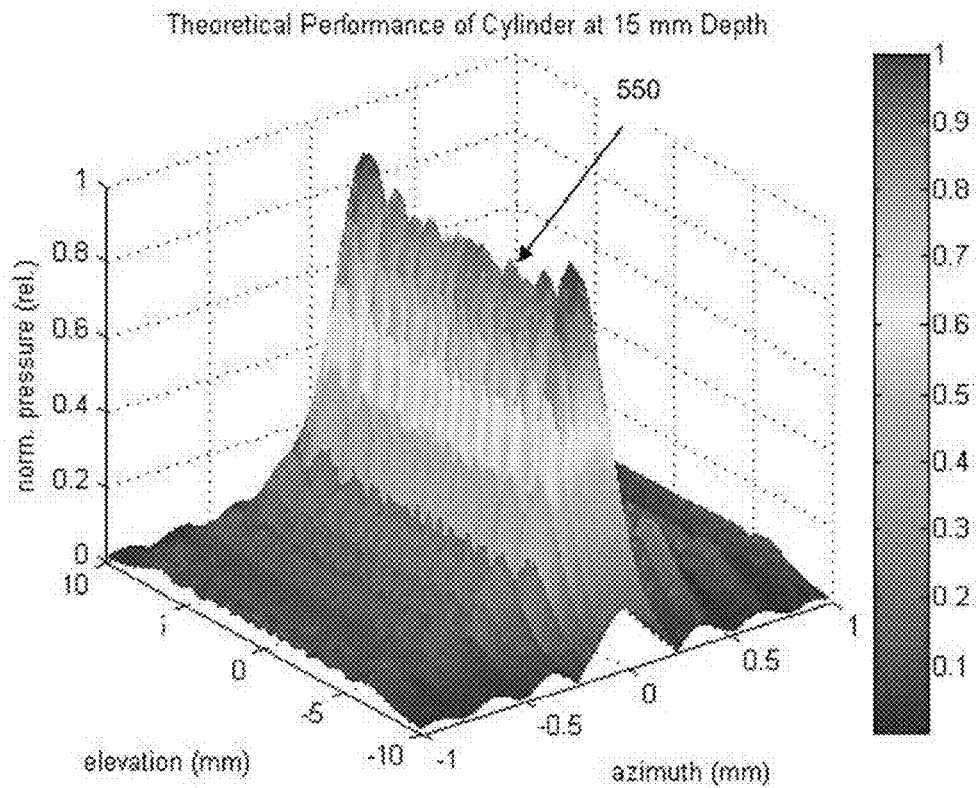
FIGS. 12A-12B are schematic illustrations and plots illustrating normalized pressure intensity distributions at a depth of 15 mm according to the embodiment of a transducer comprising a cylindrical transduction element of FIG. 11A-11B.
Figure 12B:
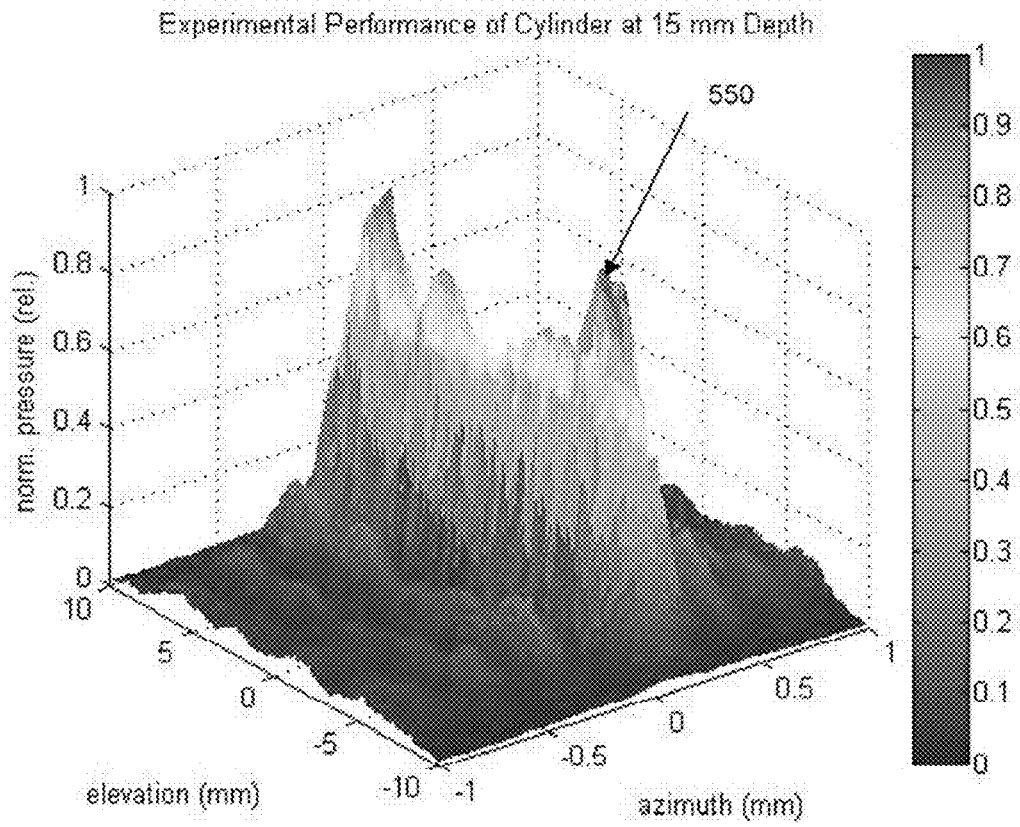
Figure 13A:
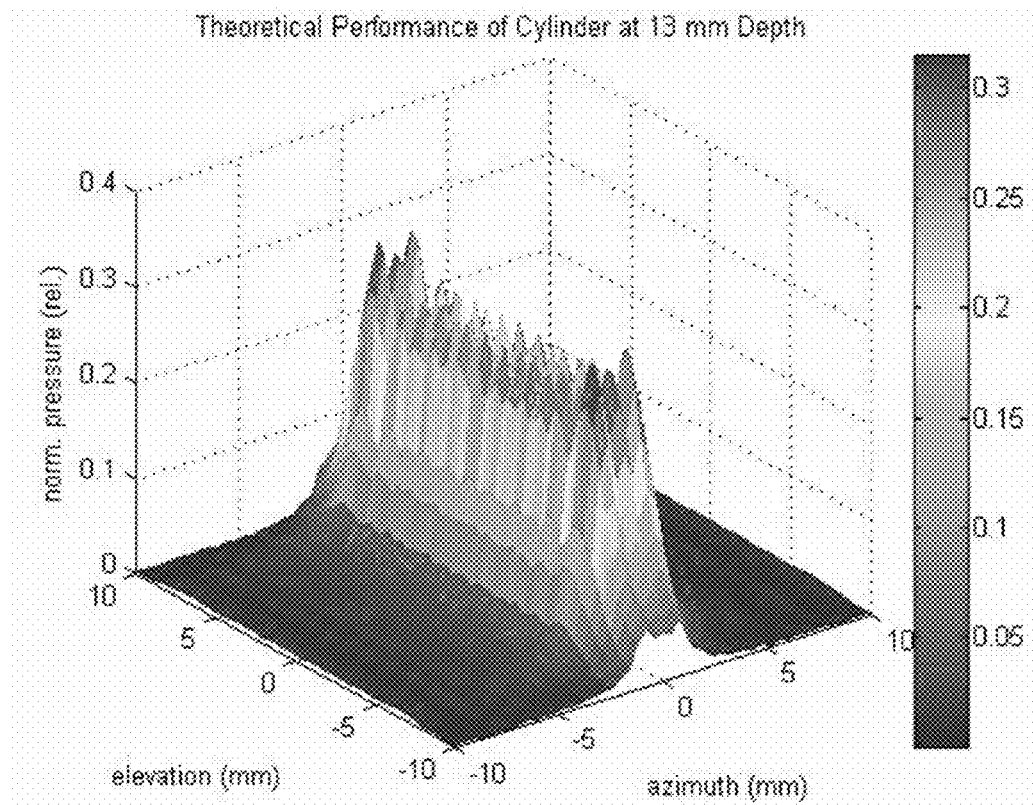
FIGS. 13A-13B are schematic illustrations and plots illustrating normalized pressure intensity distributions at a depth of 13 mm according to the embodiment of a transducer comprising a cylindrical transduction element of FIG. 11A-11B.
Figure 13B:
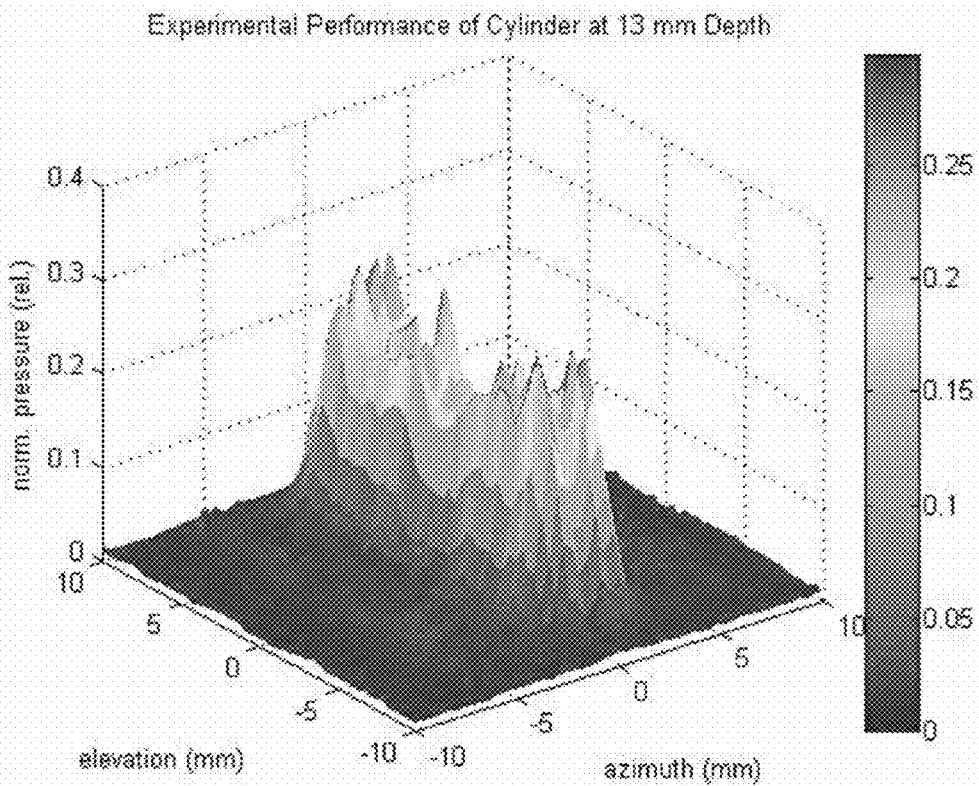

In various embodiments, an active TTZ can be moved (continuously, or non-continuously) through tissue to form a treatment area 552, such as shown in FIG. 10. With reference to the illustration in FIG. 10, the module 200 can include a transducer 280 which can emit energy through an acoustically transparent member 230. In various embodiments, a depth may refer to the focal depth 278. In one embodiment, the transducer 280 can have an offset distance 270, which is the distance between the transducer 280 and a surface of the acoustically transparent member 230. In one embodiment, the focal depth 278 of a transducer 280 is a fixed distance from the transducer. In one embodiment, a transducer 280 may have a fixed offset distance 270 from the transducer to the acoustically transparent member 230. In one embodiment, an acoustically transparent member 230 is configured at a position on the module 200 or the ultrasound system 20 for contacting the skin surface 501. In various embodiments, the focal depth 278 exceeds the offset distance 270 by an amount to correspond to treatment at a target area located at a tissue depth 279 below a skin surface 501. In various embodiments, when the ultrasound system 20 placed in physical contact with the skin surface 501, the tissue depth 279 is a distance between the acoustically transparent member 230 and the target area, measured as the distance from the portion of the hand wand 100 or module 200 surface that contacts skin (with or without an acoustic coupling gel, medium, etc.) and the depth in tissue from that skin surface contact point to the target area. In one embodiment, the focal depth 278 can correspond to the sum of an offset distance 270 (as measured to the surface of the acoustically transparent member 230 in contact with a coupling medium and/or skin 501) in addition to a tissue depth 279 under the skin surface 501 to the target region. In various embodiments, the acoustically transparent member 230 is not used.

In various embodiments, therapeutic treatment advantageously can be delivered at a faster rate and with improved accuracy by using a transducer configured to deliver energy to an expanded TTZ. This in turn can reduce treatment time and decrease pain experienced by a subject. In several embodiments, treatment time is reduced by creating a TTZ and sweeping the TTZ through an area or volume for treatment from a single transducer. In some embodiments, it is desirable to reduce treatment time and corresponding risk of pain and/or discomfort experienced by a patient. Therapy time can be reduced by treating larger areas in a given time by forming larger a TTZ 550, multiple TTZs simultaneously, nearly simultaneously, or sequentially, and/or moving the TTZ 550 to form larger treatment areas 552. In one embodiment, a reduction in treatment time is reduced by treating a given area or volume with multiple TTZs reduces the overall amount of movement for a device. In some embodiments, overall treatment time can be reduced 10%, 20%, 25%, 30%, 35%, 40%, 4%, 50%, 55%, 60%, 65%, 70%, 75%, 80% or more by through creation of continuous treatment areas 552 or discrete, segmented treatment areas 552 from a sequence of individual TTZs. In various embodiments, therapy time can be reduced by 10-25%, 30-50%, 40-80%, 50-90%, or approximately 40%, 50%, 60%, 70%, and/or 80%. Although treatment of a subject at different locations in one session may be advantageous in some embodiments, sequential treatment over time may be beneficial in other embodiments. For example, a subject may be treated under the same surface region at one depth in time one, a second depth in time two, etc. In various embodiments, the time can be on the order of nanoseconds, microseconds, milliseconds, seconds, minutes, hours, days, weeks, months, or other time periods. For example, in some embodiments, the transducer module is configured to deliver energy with an on-time of 10 ms-100 minutes (e.g., 100 ms, 1 second, 1-60 seconds, 1 minute-10 minutes, 1 minute-60 minutes, and any range therein). The new collagen produced by the first treatment may be more sensitive to subsequent treatments, which may be desired for some indications. Alternatively, multiple depth treatment under the same surface region in a single session may be advantageous because treatment at one depth may synergistically enhance or supplement treatment at another depth (due to, for example, enhanced blood flow, stimulation of growth factors, hormonal stimulation, etc.). In several embodiments, different transducer modules provide treatment at different depths. In one embodiment, a single transducer module can be adjusted or controlled for varied depths.

In one embodiment, an aesthetic treatment system includes an ultrasonic probe with a removable module that includes an ultrasound transducer configured to apply ultrasonic therapy to tissue at in a focal zone. In one embodiment, the focal zone is a point. In one embodiment, the focal zone is a line. In one embodiment, the focal zone is a two dimensional region or plane. In one embodiment, the focal zone is a volume. In various embodiments, a focal zone can be moved to sweep a volume between a first position and a second position. In various embodiments, one or more a focal zone locations are positioned in a substantially linear sequence within a cosmetic treatment zone. In one embodiment, a first set of locations is positioned within a first cosmetic treatment zone and a second set of locations is positioned within a second cosmetic treatment zone, the first zone being different from the second zone. In one embodiment, the first cosmetic treatment zone includes a substantially linear sequence of the first set of locations and the second cosmetic treatment zone includes a substantially linear sequence of the second set of locations.

In one embodiment, the transducer module 280 can provide an acoustic power in a range of about 1 W or less, between about 1 W to about 100 W, and more than about 100 W. In one embodiment, the transducer module 280 can provide an acoustic power at a frequency of about 1 MHz or less, between about 1 MHz to about 10 MHz, and more than about 10 MHz. In one embodiment, the module 200 has a focal depth 278 for a treatment at a tissue depth 279 of about 4.5 mm below the skin surface 501. Some non-limiting embodiments of transducers 280 or modules 200 can be configured for delivering ultrasonic energy at a tissue depth of 3 mm, 4.5 mm, 6 mm, less than 3 mm, between 3 mm and 4.5 mm, between 4.5 mm and 6 mm, more than more than 4.5 mm, more than 6 mm, etc., and anywhere in the ranges of 0.1-3 mm, 0.1-4.5 mm, 0.1-6 mm, 0.1-25 mm, 0.1-100 mm, etc. and any depths therein. In one embodiment, the ultrasound system 20 is provided with two or more removable transducer modules 280. In one embodiment, a transducer 280 can apply treatment at a tissue depth (e.g., about 6 mm). For example, a first transducer module can apply treatment at a first tissue depth (e.g., about 4.5 mm) and a second transducer module can apply treatment at a second tissue depth (e.g., of about 3 mm), and a third transducer module can apply treatment at a third tissue depth (e.g., of about 1.5-2 mm). In one embodiment, at least some or all transducer modules can be configured to apply treatment at substantially same depths. In various embodiments, the tissue depth can be 1.5 mm, 2 mm, 3 mm, 4.5 mm, 7 mm, 10 mm, 12 mm, 14 mm, 15 mm, 17 mm, 18 mm, and/or 20 mm, or any range therein (including but not limited to 12-20 mm, or higher).

In one embodiment, a transducer module permits a treatment sequence at a fixed depth at or below the skin surface. In one embodiment, a transducer module permits a treatment sequence at a range of depths below the skin surface. In several embodiments, the transducer module comprises a movement mechanism configured to move the ultrasonic treatment at the TTZ. In one embodiment, the linear sequence of individual TTZs has a treatment spacing in a range from about 0.01 mm to about 25 mm. For example, the spacing can be 1.1 mm or less, 1.5 mm or more, between about 1.1 mm and about 1.5 mm, etc. In one embodiment, the individual TTZs are discrete. In one embodiment, the individual TTZs are overlapping. In one embodiment, the movement mechanism is configured to be programmed to provide variable spacing between the individual TTZs. In several embodiments, a transducer module comprises a movement mechanism configured to direct ultrasonic treatment in a sequence so that TTZs are formed in linear or substantially linear sequences separated by a treatment distance. For example, a transducer module can be configured to form TTZs along a first linear sequence and a second linear sequence separated by a treatment distance from the first linear sequence. In one embodiment, treatment distance between adjacent linear sequences of individual TTZs is in a range from about 0.01 mm to about 25 mm. For example, the treatment distance can be 2 mm or less, 3 mm or more, between about 2 mm and about 3 mm, etc. In several embodiments, a transducer module can comprise one or more movement mechanisms configured to direct ultrasonic treatment in a sequence so that TTZs are formed in linear or substantially linear sequences of individual thermal lesions separated by a treatment distance from other linear sequences. In one embodiment, the treatment distance separating linear or substantially linear TTZs sequences is the same or substantially the same. In one embodiment, the treatment distance separating linear or substantially linear TTZs sequences is different or substantially different for various adjacent pairs of linear TTZs sequences.

Band Therapy Using a Cylindrical Transducer with an Imaging Element

Figure 21:
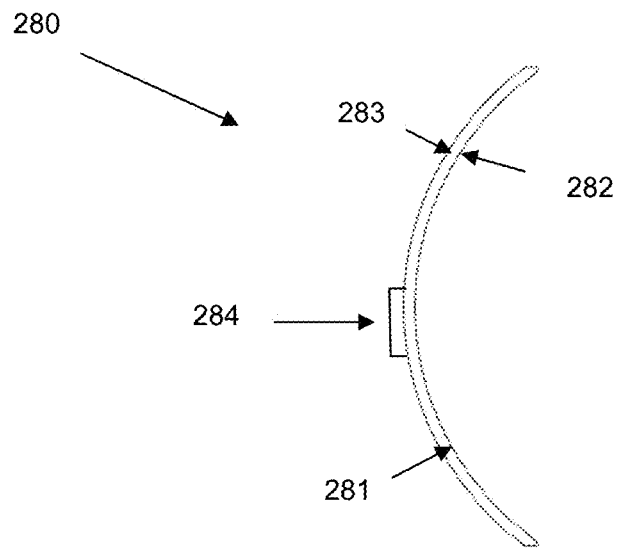
FIG. 21 is a cross-section view of a combined imaging and cylindrical therapy transducer according to an embodiment of the present invention.
Figure 22:
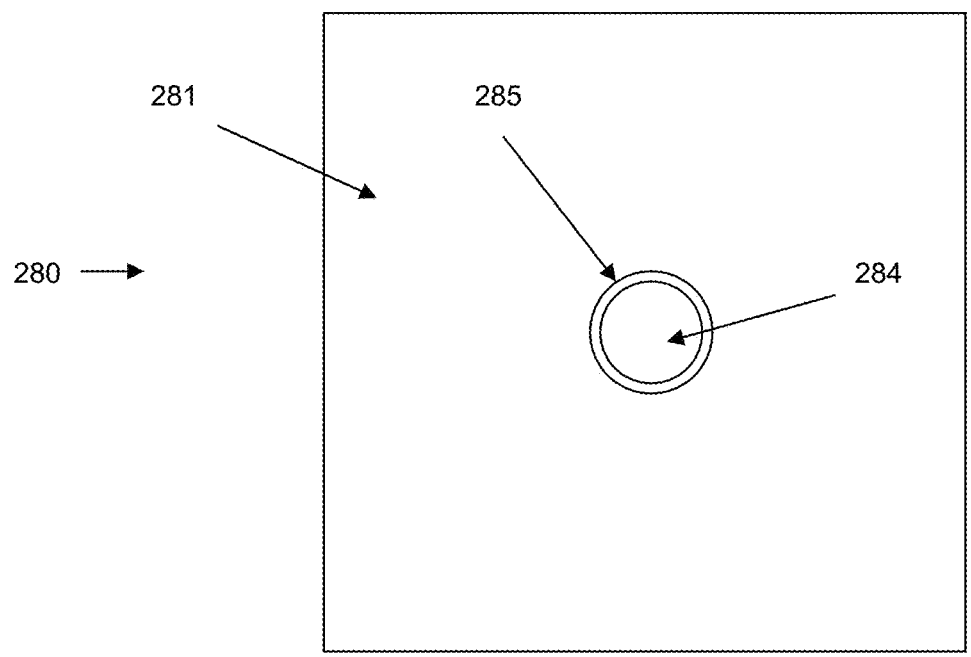
FIG. 22 is a side view of a combined imaging and cylindrical therapy transducer according to FIG. 21.

In various embodiments, including an imaging transducer or imaging element with a cylindrical transduction element 281 can be used to improve safety and/or efficacy of a treatment. In one embodiment, an imaging element can be used to confirm acceptable coupling between the ultrasound therapy transducer and/or identify target tissue below the skin surface. As illustrated at FIGS. 21 and 22, in various embodiments, a transducer 280 comprises a cylindrical transduction element 281 and one or more imaging elements 284. The imaging element 284 is configured to image a region of interest at any suitable tissue depths 279. In one embodiment, an imaging element is centered on a therapy element. In one embodiment, an imaging element is axis symmetric with a therapy element. In one embodiment, an imaging element is not axis symmetric with a therapy element. In one embodiment, the imaging axis may be pointed in a completely different direction and translated from the therapy beam axis. In one embodiment, the number of imaging elements in the aperture may be greater than one. For example, in one embodiment, the imaging elements may be located on each corner of a cylinder pointed straight ahead and/or in the middle. In one embodiment, a combined imaging and cylindrical therapy transducer 280 comprises a cylindrical transduction element 281 and one or more imaging elements 284. In one embodiment, a combined imaging and cylindrical therapy transducer 280 comprises a cylindrical transduction element 281 with an opening 285 through which one imaging element 284 is configured to operate. In one embodiment, the opening 284 is a circular hole through the wall thickness of the cylindrical transduction element 281 at the center of the X-axis (azimuth) and Y-axis (elevation) of the cylindrical transduction element 281. In one embodiment, the imaging element 284 is circular in cross-section and fits in the opening 284.

In one embodiment, first and second removable transducer modules are provided. In one embodiment, each of the first and second transducer modules are configured for both ultrasonic imaging and ultrasonic treatment. In one embodiment, a transducer module is configured for treatment only. In one embodiment, an imaging transducer may be attached to a handle of a probe or a hand wand. The first and second transducer modules are configured for interchangeable coupling to a hand wand. The first transducer module is configured to apply ultrasonic therapy to a first treatment area, while the second transducer module is configured to apply ultrasonic therapy to a second treatment area. The second treatment area can be at a different depth, width, height, position, and/or orientation than the first treatment area.

Band Therapy Using a Coated Transducer Configured to Reduce Edge Effects

Figure 23:
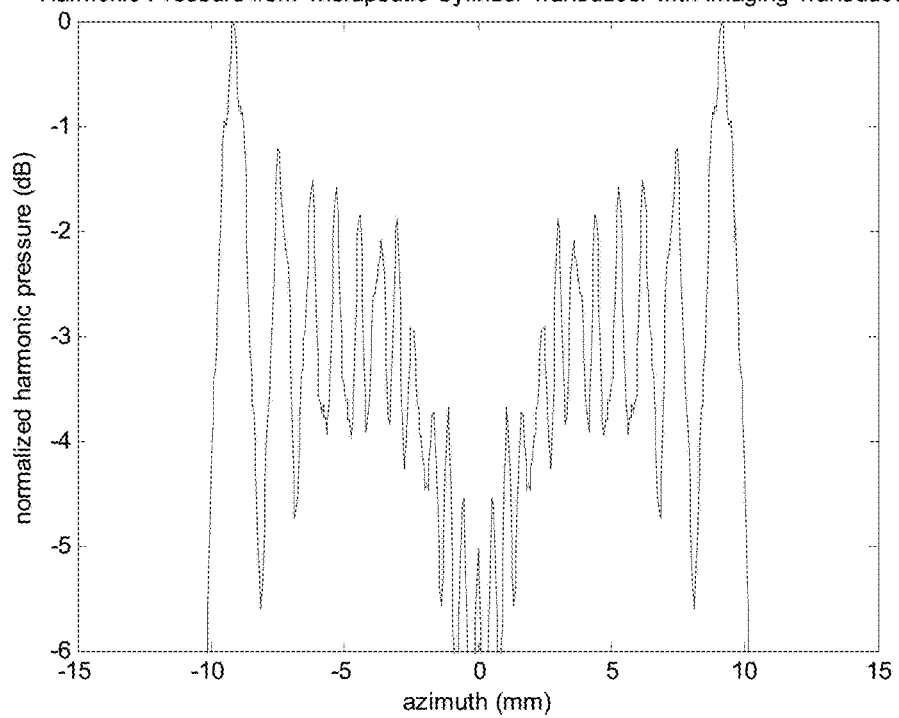
FIG. 23 is a plot illustrating harmonic pressure across an azimuth of an embodiment of a cylindrical element with an imaging element.

In various embodiments, treatment advantageously can be delivered with improved accuracy. Further, efficiency, comfort and safety can be increased if variance is reduced in a treatment area. This in turn can reduce treatment time and decrease pain experienced by a subject. In some instances, non-uniform heating at a focal zone can result from geometric aspects of a transducer. Inconsistencies in pressure or temperature profiles can be attributed to edge effects, which can cause spikes in pressure or temperature around the focal zone of a transducer. Thus, with edge effects, instead of achieving a uniform line segment of heating, the segment is broken into many isolated hot spots which may fail to meet an objective a more uniform heat distribution at the focal zone. This phenomenon is further exacerbated at high heating rates which relate to elevated acoustic pressures. This is due to the generation of nonlinear harmonics created especially in areas of high pressure. Energy at harmonic frequencies is more readily absorbed than energy at the fundamental frequency. In one embodiment, energy absorption is governed by the following equation:

$$H = 2 * \alpha * f * p^2 / Z \quad (1)$$

where alpha is the absorption constant in nepers per MHz cm, f is frequency in MHz, p is the pressure at that frequency, Z is the acoustic impedance of tissue, and H is the heating rate in Watt/cm$^3$. In one embodiment, the amount of harmonics produced is proportional to the intensity. FIG. 23 shows the normalized harmonic pressure at the focal depth across an azimuth of one embodiment of a cylindrical element with an imaging element. FIG. 23 shows the rapid swings in harmonic pressure at this depth which causes hot spots and non-uniform heating.

In one embodiment, a way to combat these hot and cold spots that are the result from edge effects is to reduce the average intensity at the focal depth and/or increase the heating time. These two processes can reduce the amount on nonlinear heating as well as allow for the conduction of the heat away from the hot spot into the cold areas. The thermal conduction of tissue effectively acts as a low pass filter to the acoustic intensity distribution as the heating time increases. Although these methods may reduce the non-uniform heating issues, they can also reduce the localization of the heating zone and can also increase the treatment time. Therefore, three performance areas of ultrasound therapy, e.g. efficacy, comfort, and treatment time, are adversely affected. In one embodiment, a more normalized pressure profile results in more consistent therapy, such that temperature increase through heating, coagulation, and/or ablation is more predictable and can better ensure the desired or targeted temperature profiles are obtained in the TTZ 550. In various embodiments, apodization of edge effects is accomplished with transducers coated in specific regions.

Figure 24:
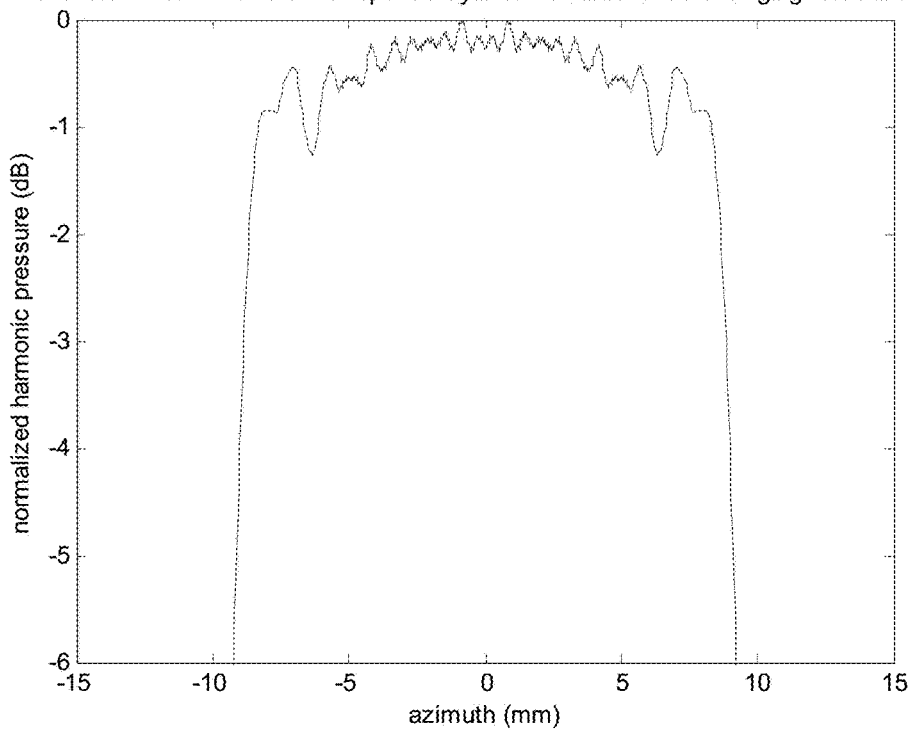
FIG. 24 is a plot illustrating harmonic pressure across an azimuth of an embodiment of a coated cylindrical element with an imaging element.

In one embodiment, use of coatings, or shadings, can help circumvents these issues such that efficacy, comfort and treatment time are optimized. FIG. 24 shows a harmonic pressure distribution from an embodiment of a shaded aperture, or a coated element, that has an imaging transducer. In one embodiment, the coated element is a coated cylindrical element with an imaging element. The variation in harmonic pressure across the treatment line varies by less the 1.5 dB with the highest intensity near the center and sharp edges at −10 mm and +10 mm. In one embodiment, the coated element design does not require the conduction of heat away from hot spots since the tissue along the focused line has a uniform temperature increase during the absorption. Therefore, the amount of intensity at the focus can be increased to localize the heating zone and reduce treatment time.

Figure 25:
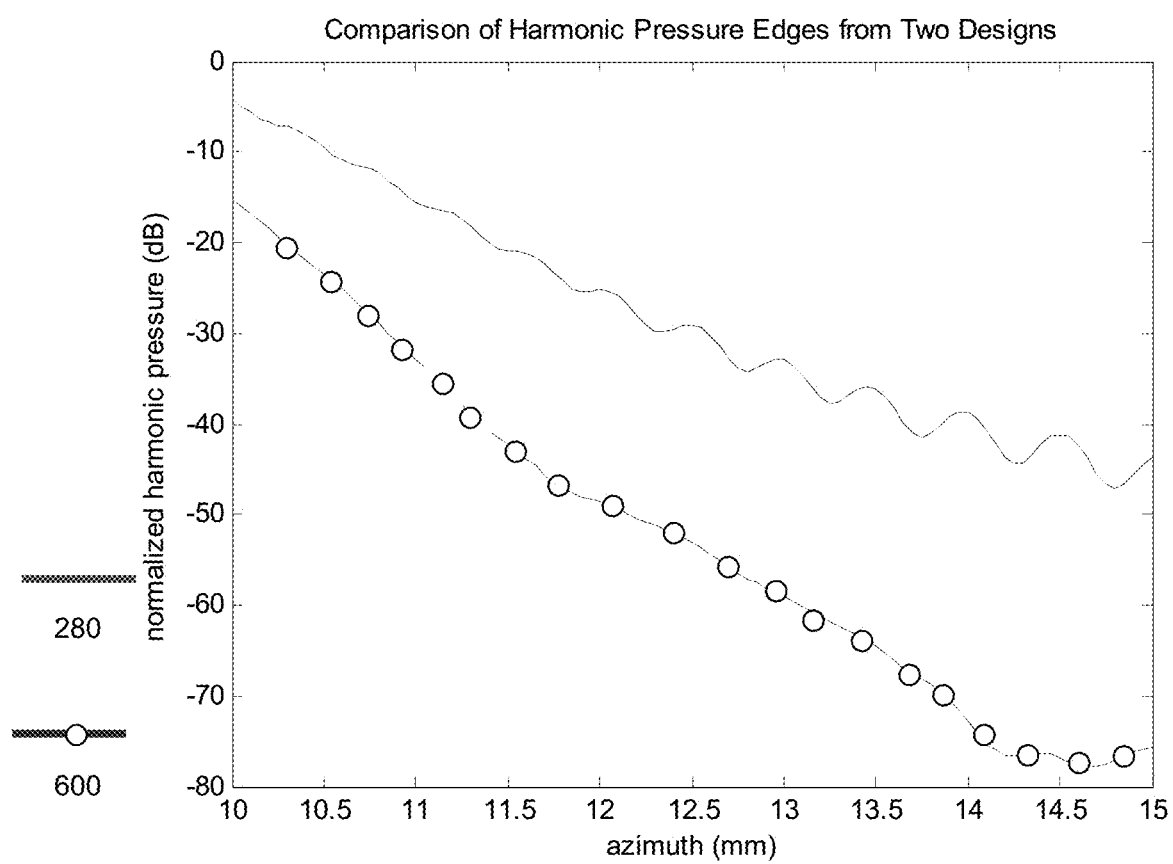
FIG. 25 is a plot illustrating harmonic pressure across an azimuth of an embodiment of a cylindrical element with an imaging element compared to an embodiment of a coated cylindrical element with an imaging element.
Figure 27:
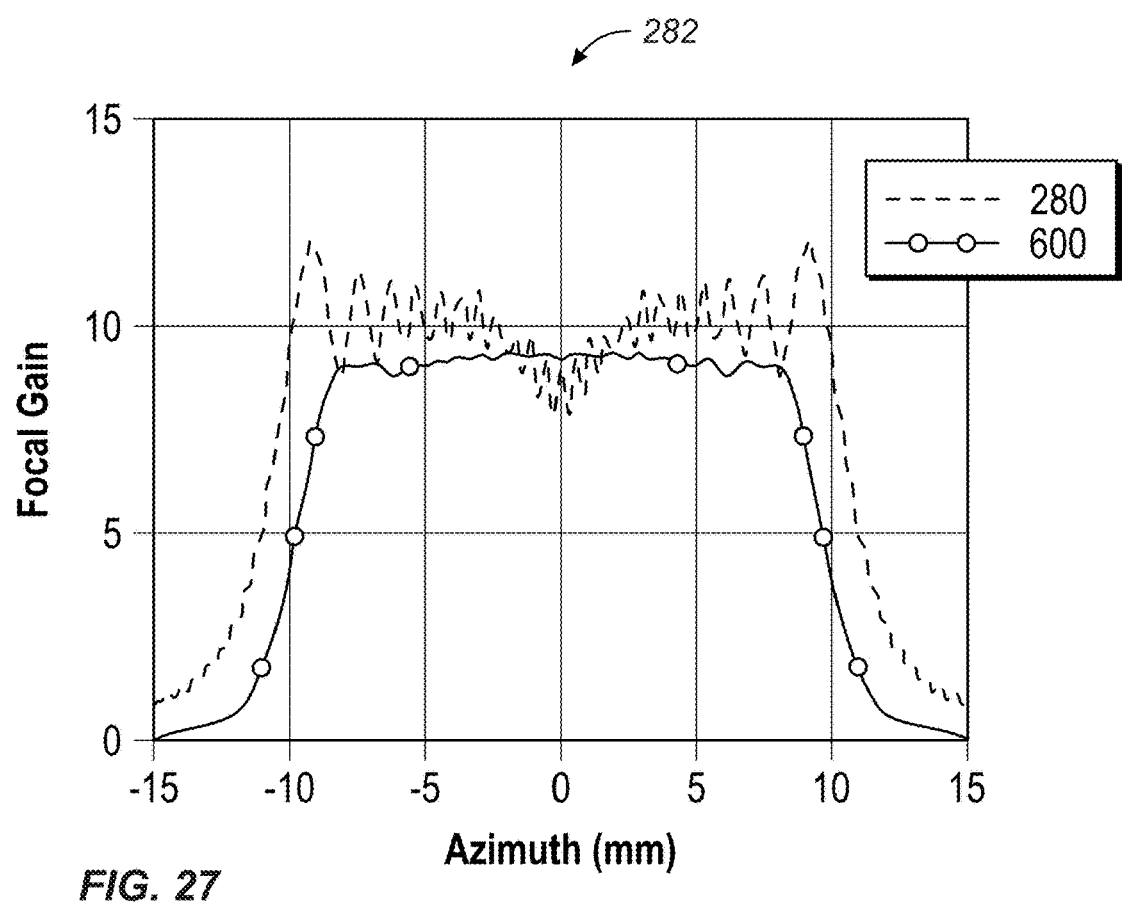
FIG. 27 is a plot illustrating focal gain across the azimuth of two embodiments of cylindrical transduction elements.

In one embodiment, the coated element is a shaded therapeutic cylinder. In one embodiment, a coated element also has benefits outside the intended heating zone. In one embodiment, the boundary between the heated and unheated junction is vastly improved when compared to an uncoated element. FIG. 25 shows a comparison of harmonic pressure across an azimuth of an embodiment of a cylindrical element 280 compared to an embodiment of a coated cylindrical element 600 at this boundary. FIG. 25 shows that, in one embodiment, the possible harmonic pressures are approximately 20 dB lower for the shaded aperture with a coated cylindrical element 600, which helps confine the heating zone and maximize comfort. In one embodiment, areas of plating or non-plating are initially used to define regions where the piezoelectric material will be poled or not poled. Regions where there is plating define regions that will be poled or actually mechanically vibrating. In one embodiment, a cylindrical element 280 can be uncoated. Further, an uncoated region may be considered uncoated to the extent it does not have an electrically conductive coating—the uncoated region may have other types of surface coatings in certain embodiments. In one embodiment, a cylindrical element is completely coated. For example, in one embodiment, a first transducer 280 includes a first coated region 287 that fully plates the concave surface 282 of the cylindrical transduction element and a second coated region 287 that fully plates the convex surface 283 of the cylindrical transduction element. A second coated transducer 600 includes a first coated region 287 that fully plates the concave surface 282 of the cylindrical transduction element and at least a second coated region 287 that partially plates the convex surface 283 of the cylindrical transduction element. As shown in FIG. 27, the fully coated first transducer 281 demonstrates the spikes in focal gain due to edge effects.

Referring to FIGS. 11A-13B, in one embodiment, transducer treatment profiles were plotted based on theoretical and experimental performance with a cylindrical transduction element 281 that was coated on the entire concave surface 282 and the entire convex surface 283 with a coating. In one embodiment, the coating is a metal. In one embodiment, the coating is a conductive metal. In one embodiment, the coating is an electrical conductor. In various embodiments, the coating is plated with any one or more of silver, gold, platinum, mercury, copper or other materials. In one embodiment, a coating comprises fired silver. In one embodiment, a surface is fully coated. In one embodiment, a surface is fully non-coated. In one embodiment, a surface is partially coated and partially non-coated. The normalized pressure is proportional to a thermal heating measure at the specified depth. The discontinuous spikes (pointed regions at the top of the plots) plots indicate pressure and/or temperature peaks that occur as a result of the geometric edge effects of the geometry of the cylindrical transduction element 281. In various embodiments, the spikes, or peaks, can be reduced with a coated transducer 600 comprising one or more coated regions 287. In one embodiment, the coated region 287 only partially coats a transducer surface. In one embodiment, the coated region 287 does not completely coat a transducer surface.

Figure 26:
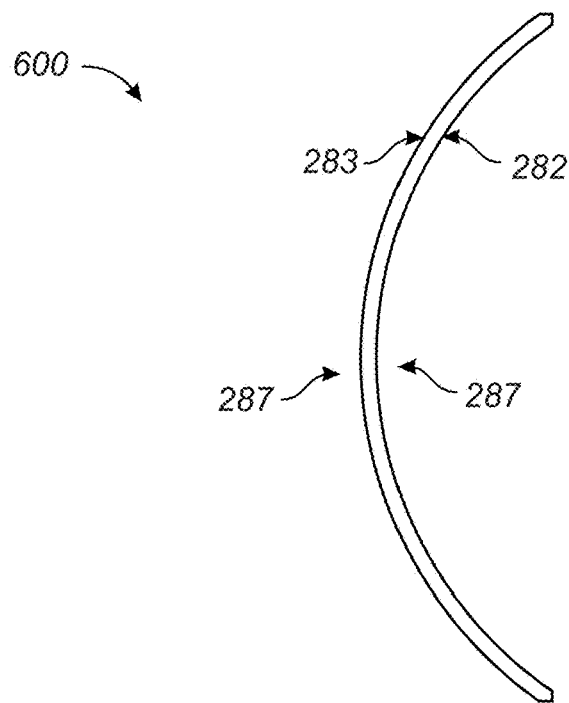
FIG. 26 is a side view of a coated transducer comprising a cylindrical transduction element with one or more coated regions according to an embodiment of the present invention.

As shown in FIG. 26, in various embodiments, a coated transducer 600 comprises a cylindrical transduction element 281 with one or more coated regions 287. In various embodiments, the coated region 287 coats part, a portion, and/or all of a surface of the transducer 600. In various embodiments, the coated region 287 coats part or all of a surface of the cylindrical transduction element 281. In various embodiments, a coated transducer 600 comprises one or more imaging elements 284. In some embodiments, one, two, three or more imaging element(s) are placed in 'unused regions' of coatings/shading for the purpose of imaging.

The edge effects from the geometry of one embodiment of a combined imaging and cylindrical therapy transducer comprising a cylindrical transduction element 281 with an opening 285 through it are more pronounced due to the additional edges of the opening 285. FIG. 27 is a plot illustrating focal gain across the azimuth of two embodiments of combined imaging and cylindrical therapy transducers with different coatings. A first transducer 280 includes a first coated region 287 that fully plates the concave surface 282 of the cylindrical transduction element and a second coated region 287 that fully plates the convex surface 283 of the cylindrical transduction element. Both the first and the second coated regions 287 of the first transducer 280 are plated with silver. A second coated transducer 600 includes a first coated region 287 that fully plates the concave surface 282 of the cylindrical transduction element and at least a second coated region 287 that partially plates the convex surface 283 of the cylindrical transduction element. Both the first and the second coated regions 287 of the second transducer 600 are plated with silver. As shown in FIG. 27, the fully coated first transducer 281 demonstrates the spikes in focal gain due to edge effects. The partially coated second transducer 600 has a more consistent, normalized performance output with the spikes substantially reduced and/or removed. In various embodiments, a coated transducer 600 reduces the peaks such that variance around the focal depth is reduced by 1-50%, 25-100%, 75-200%, and/or 10-20%, 20-40% and 60-80%. In various embodiments, a coated transducer 600 reduces the peaks such that variance of the intensity in a location around the focal depth is +/−0.01-5 mm, 5 mm or less, 4 mm or less, 3 mm or less, 2 mm or less, 1 mm or less, 0.5 mm or less, 0.25 mm or less, 0.1 mm or less, 0.05 mm or less, or any range therein. In various embodiments, a coated transducer 600 reduces the peaks in focal gain such that variance in focal gain is 0.01-0.1, 0.01-1.0, 0.01-5, 0.01-10, 1-5, 10, 9, 8, 7, 6, 5, 4, 3, 2, 1 or less, or any range therein.

Figure 28:
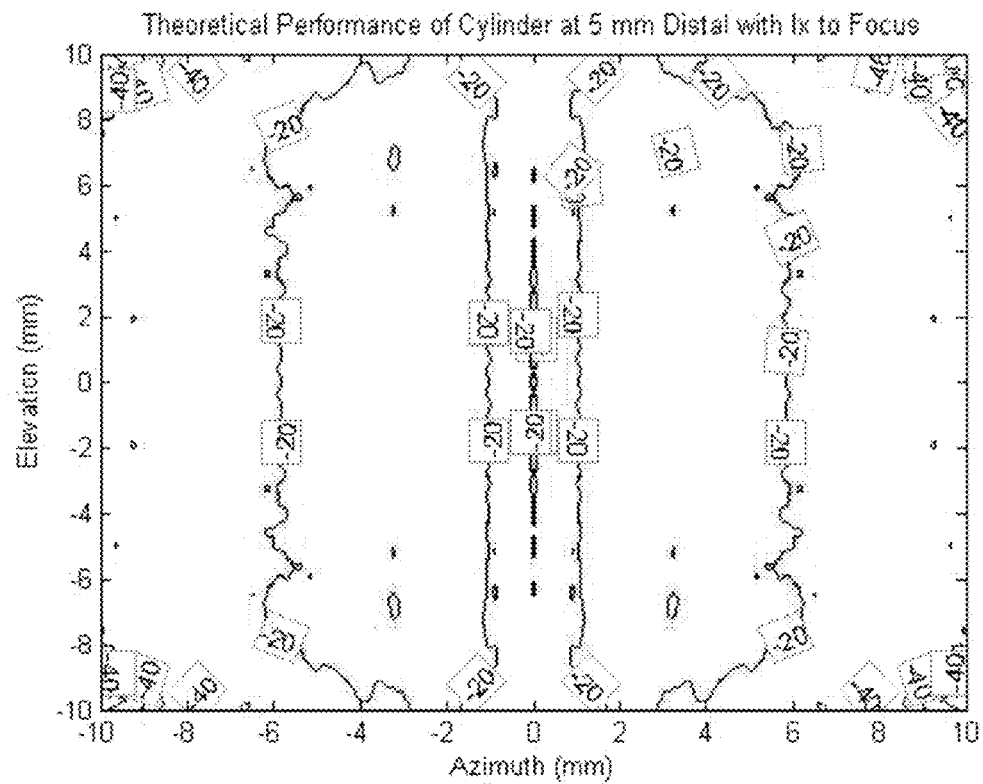
FIG. 28 is a schematic plot illustrating normalized pressure intensity distributions at a depth distal to the focal zone by about 5 mm according to an embodiment of a coated transducer comprising a cylindrical transduction element with one or more coated regions.
Figure 29:
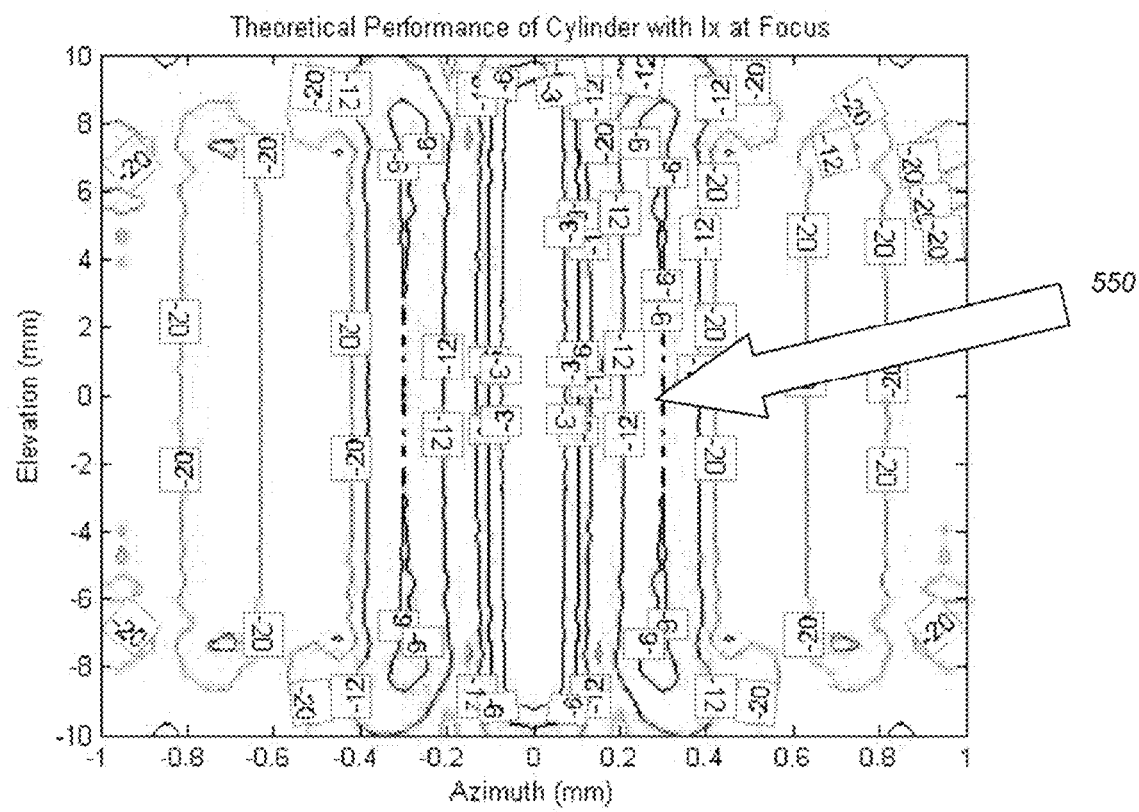
FIG. 29 is a schematic plot illustrating normalized pressure intensity distributions at a focal depth according to the embodiment of the coated transducer of FIG. 28.
Figure 30:
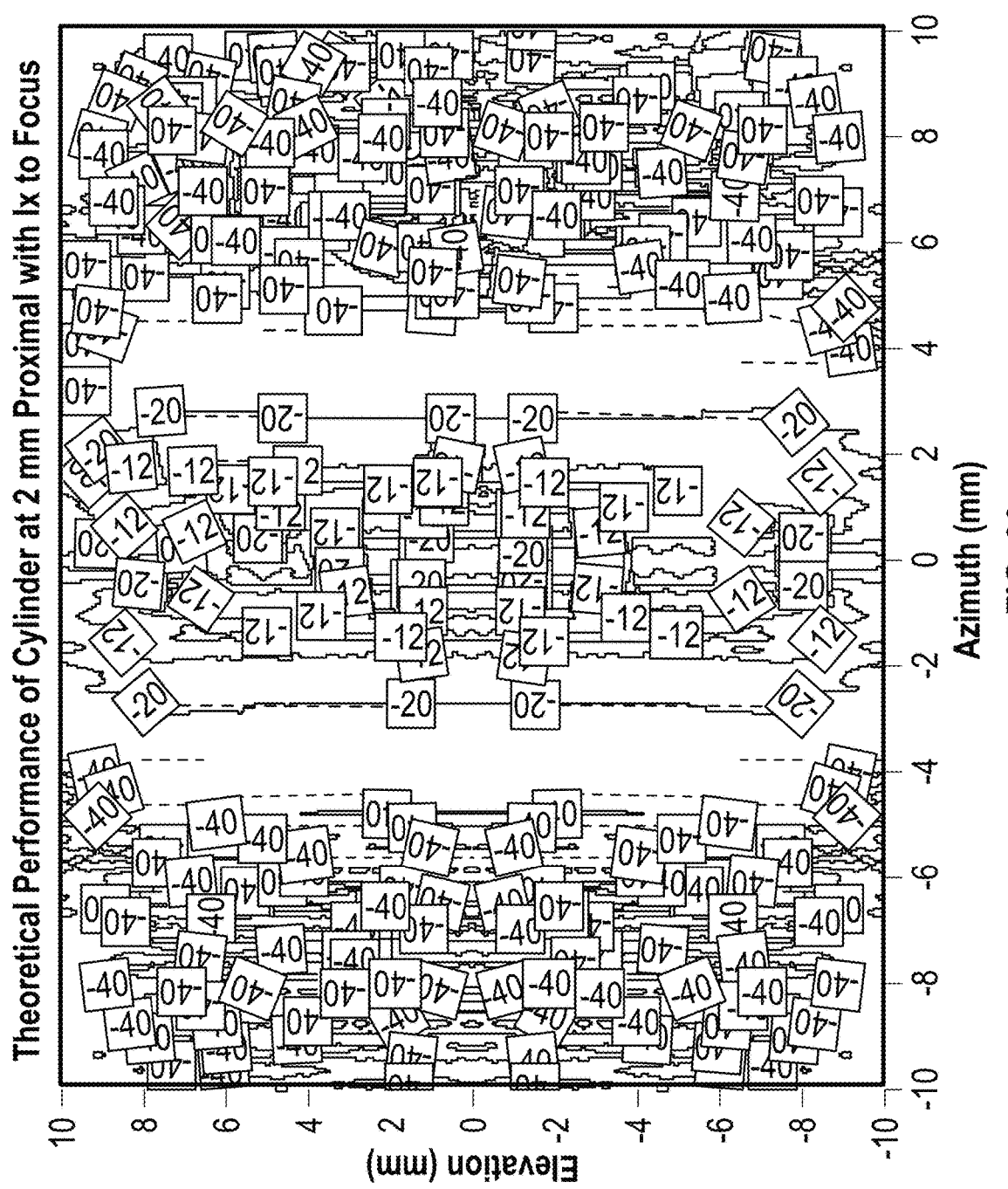
FIG. 30 is a schematic plot illustrating normalized pressure intensity distributions at a depth proximal to the focal depth by about 2 mm according to the embodiment of the coated transducer of FIG. 28.

As described in Example 2 below, FIGS. 28, 29, and 30 illustrate the embodiment of the performance of the partially coated second transducer 600 in FIG. 27 at different depths. In the illustrated embodiment, the partially coated second transducer 600 has a focal depth of 15 mm. In various embodiments, the focal depth can be at any depth. In various embodiments, the focal depth is at 7, 8, 9, 10, 12, 13, 13.6, 14, 15, 16, 17, 18, or any depth therein.

In one embodiment, the coated region 287 is plating. In one embodiment, the coated region 287 is a conductive material. In one embodiment, the coated region 287 is a semi-conductive material. In one embodiment, the coated region 287 is an insulator material. In various embodiments, the coated region 287 is silver, copper, gold, platinum, nickel, chrome, and/or any conductive material that will adhere with the surface of a piezoelectric material, or any combinations thereof. In one embodiment, the coated region 287 is silver plating.

In various embodiments, a cylindrical transduction element 281 has an azimuth (x-axis) dimension in the range of 1-50 mm, 5-40 mm, 10-20 mm, 15-25 mm, and/or 15 mm, 16 mm, 17 mm, 18 mm, 19 mm, 20 mm, 21 mm, 22 mm, 23 mm, 24 mm, and 25 mm. In various embodiments, a cylindrical transduction element 281 has an elevation (y-axis) dimension in the range of 1-50 mm, 5-40 mm, 10-20 mm, 15-25 mm, and/or 15 mm, 16 mm, 17 mm, 18 mm, 19 mm, 20 mm, 21 mm, 22 mm, 23 mm, 24 mm, and 25 mm. In various embodiments, a cylindrical transduction element 281 has focal depth (z-axis) dimension in the range of 1-50 mm, 5-40 mm, 10-20 mm, 15-25 mm, 12-17 mm, 13-15 mm, and/or 10 mm, 11 mm, 12 mm, 13 mm, 13.6 mm, 14 mm, 15 mm, 16 mm, 17 mm, 18 mm, 19 mm, 20 mm, 21 mm, 22 mm, 23 mm, 24 mm, and 25 mm. In some non-limiting embodiments transducers can be configured for a treatment zone at a tissue depth below a skin surface of 1.5 mm, 3 mm, 4.5 mm, 6 mm, less than 3 mm, between 1.5 mm and 3 mm, between 1.5 mm and 4.5 mm, more than more than 4.5 mm, more than 6 mm, and anywhere in the ranges of 0.1 mm-3 mm, 0.1 mm-4.5 mm, 3 mm-7 mm, 3 mm-9 mm, 0.1 mm-25 mm, 0.1 mm-100 mm, and any depths therein.

In various embodiments, a coated transducer 600 comprising a cylindrical transduction element 281 has one, two, three, four, or more coated regions 287. In one embodiment, a coated region 287 covers an entire surface of the element. In one embodiment, a coated region 287 covers a portion of a surface of the element. In various embodiments, the coated region 287 includes a conductive plating. In one embodiment, a coated region 287 includes a silver plating to form an electrode. When an electrical signal is applied to an electrode at a coated region 287, the coated region 287 expands and/or contracts the corresponding portion of the cylindrical transduction element 281. In various embodiments, the coated region 287 has a shape or border that is a complete or a partial point, edge, line, curve, radius, circle, oval, ellipse, parabola, star, triangle, square, rectangle, pentagon, polygon, a combination of shapes, or other shape. In various embodiments, a coated transducer 600 can also comprise an opening 285.

Figure 31:
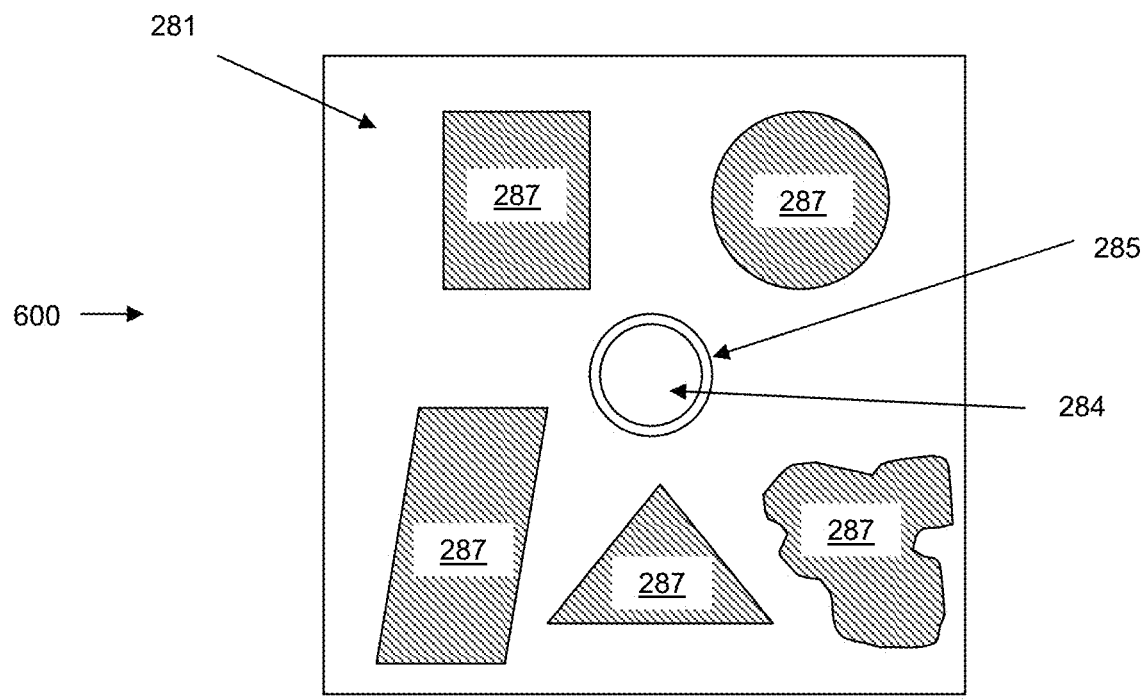
FIG. 31 is a side view of a coated transducer according to an embodiment of the present invention.

In one embodiment illustrated at FIG. 31, a partially coated transducer 600 comprising a cylindrical transduction element 281 has one, two, three, four, or more coated regions 287 of one or more shapes on a convex 283 surface. In one embodiment, a partially coated transducer 600 comprising a cylindrical transduction element 281 has one, two, three, four, or more coated regions 287 of one or more shapes on a concave 282 surface. In various embodiments, the coated region 287 has a lateral edge 293, a side edge 290, and a medial edge 291. The various edges can be straight, curved, and/or have a radius, and the sizes can be modified to result in various performance profiles.

Figure 32:
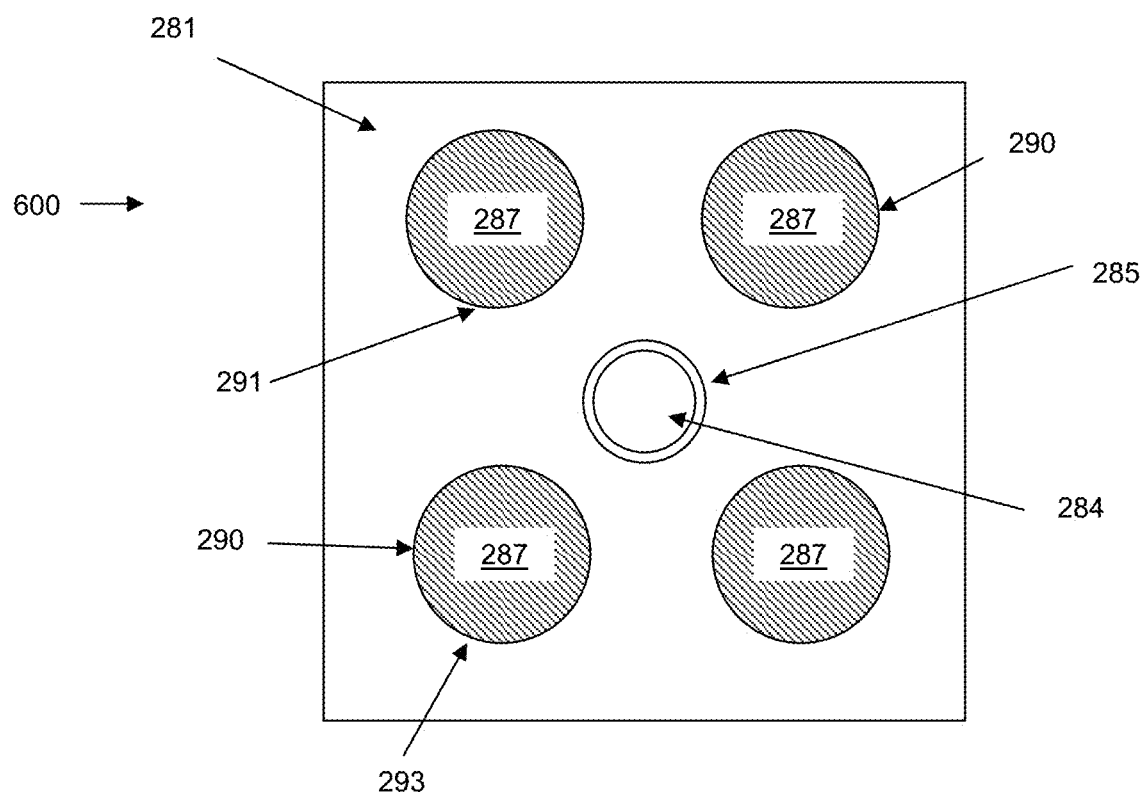
FIG. 32 is a side view of a coated transducer according to an embodiment of the present invention.

In one embodiment illustrated at FIG. 32, a partially coated transducer 600 comprising a cylindrical transduction element 281 has one, two, three, four, or more circular, round, curved and/or elliptical coated regions 287. In various embodiments, the coated region 287 has a lateral edge 293, a side edge 290, and a medial edge 291. The various edges can be straight, curved, and/or have a radius, and the sizes can be modified to result in various performance profiles.

Figure 33:
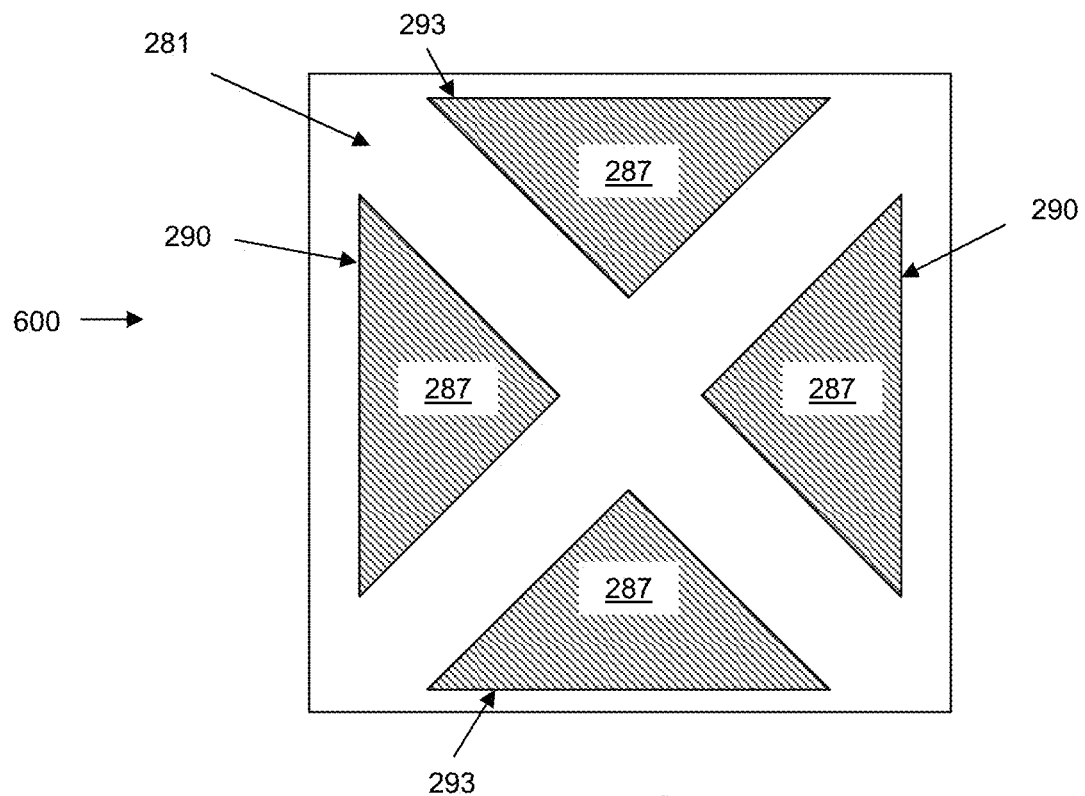
FIG. 33 is a side view of a coated transducer according to an embodiment of the present invention.

In one embodiment illustrated at FIG. 33, a partially coated transducer 600 comprising a cylindrical transduction element 281 has one, two, three, four, or more triangular coated regions 287. In various embodiments, the coated region 287 has a lateral edge 293, a side edge 290, and a medial edge 291. The various edges can be straight, curved, and/or have a radius, and the sizes can be modified to result in various performance profiles.

Figure 34:
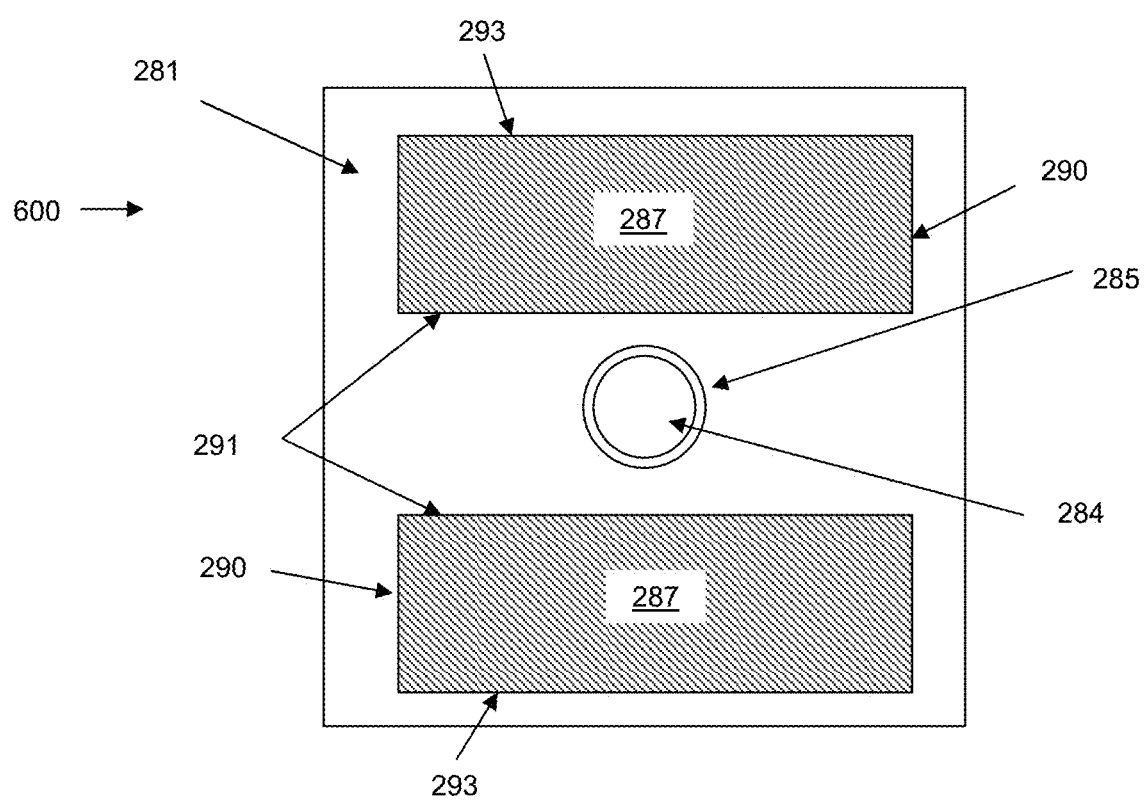
FIG. 34 is a side view of a coated transducer according to an embodiment of the present invention.

In one embodiment illustrated at FIG. 34, a partially coated transducer 600 comprising a cylindrical transduction element 281 has one, two or more square, rectangular, and/or polygon coated regions 287. In various embodiments, the coated region 287 has a lateral edge 293, a side edge 290, and a medial edge 291. The various edges and/or sizes can be modified to result in various performance profiles.

Figure 35:
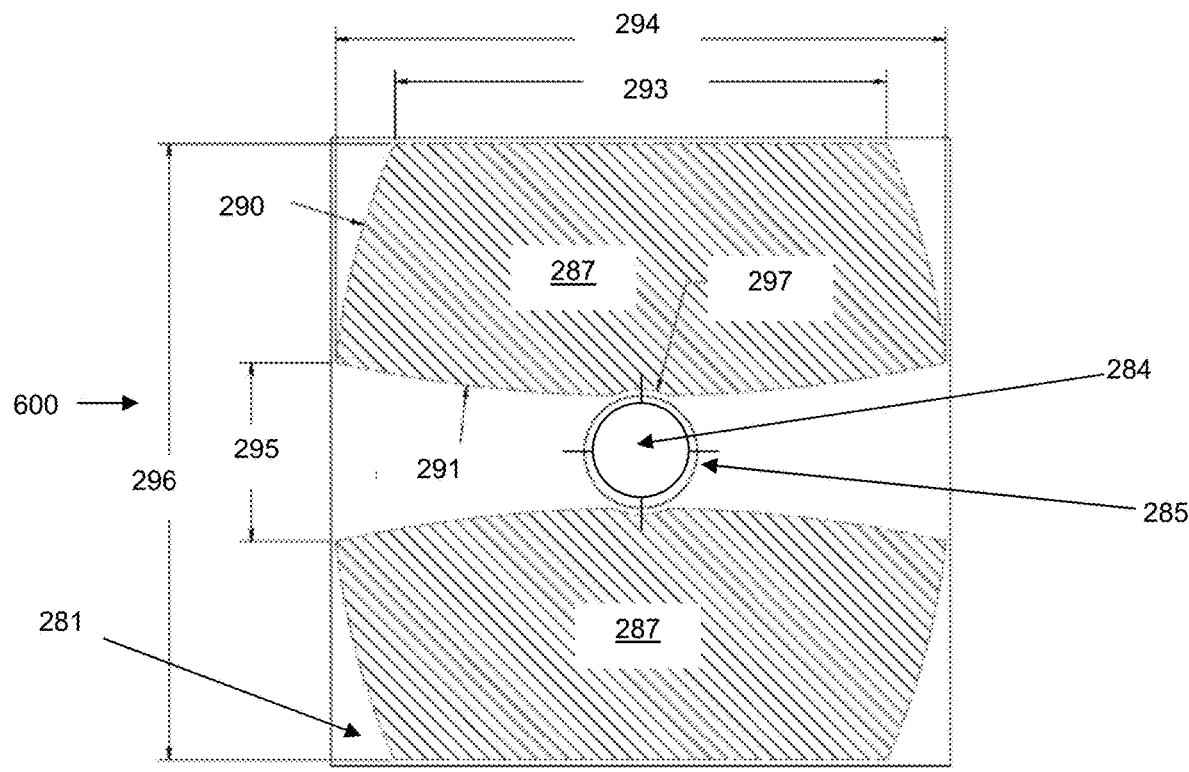
FIG. 35 is a side view of a coated transducer according to an embodiment of the present invention.

In one embodiment illustrated at FIG. 35, a partially coated transducer 600 comprising a cylindrical transduction element 281 has one, two or more combined and/or mixed shape coated regions 287. In one embodiment illustrated at FIG. 35, a partially coated transducer 600 is a combined imaging and cylindrical therapy transducer comprising a cylindrical transduction element 281 with an opening 285 for an imaging element 284. In one embodiment, the coated transducer 600 includes a concave surface 282 that is fully plated with fired silver, and has a convex surface 283 with two coated regions 287 that are plated with fired silver to form electrodes. When an electrical signal is applied to an electrode at a coated region 287, the coated region 287 expands and/or contracts the corresponding portion of the cylindrical transduction element 281. In some embodiments, the shape may be applied before or after the poling process, as vibration will occur where the electrode is located. In various embodiments, an electrode could be defined before or after poling. In various embodiments, a coating pattern may be on the concave or convex surface. In one embodiment, the coated region 287 has a lateral edge 293, a first and second side edge 290, and a medial edge 291 with a central edge 297. The various edges can be straight, curved, and/or have a radius. Various dimensions 294, 295, 296, and the various edges can be modified to result in various performance profiles. In one embodiment, the medial edge 291 along the curved dimension (elevation) is a portion of an ellipse. In one embodiment, the medial edge 291 along the curved dimension (elevation) is a portion of a parabola. In one embodiment, the first and second side edge 290 along the uncurved dimension (azimuth) is a portion of a parabola. In one embodiment, the first and second side edge 290 along the uncurved dimension (azimuth) is a portion of an ellipse.

Figure 36:
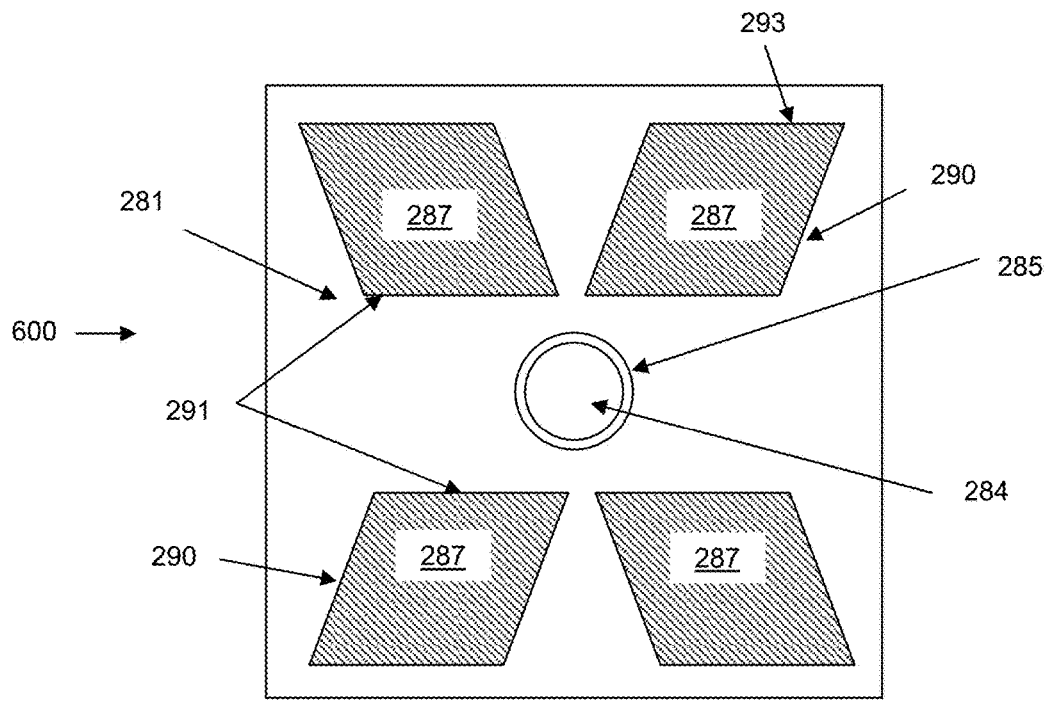
FIG. 36 is a side view of a coated transducer according to an embodiment of the present invention.

In one embodiment illustrated at FIG. 36, a partially coated transducer 600 comprising a cylindrical transduction element 281 has one, two, three, four, or more diamond, rhombus, and/or other polygon coated regions 287. In various embodiments, the coated region 287 has a lateral edge 293, a side edge 290, and a medial edge 291. The various edges and/or sizes can be modified to result in various performance profiles.

Figure 37:
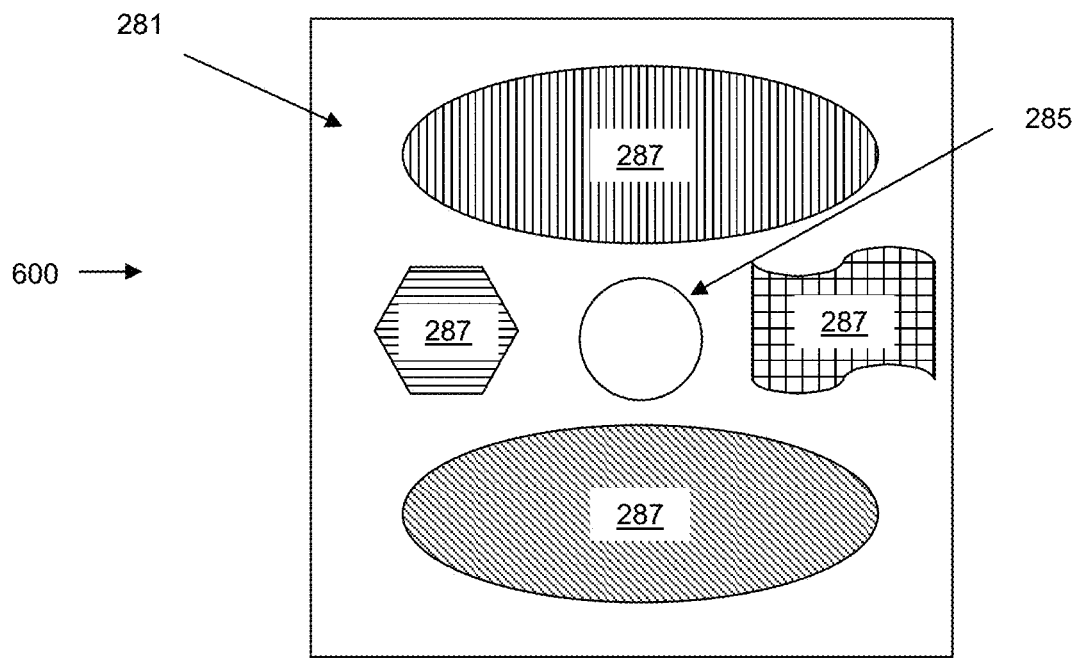
FIG. 37 is a side view of a coated transducer according to an embodiment of the present invention.
Figure 38:
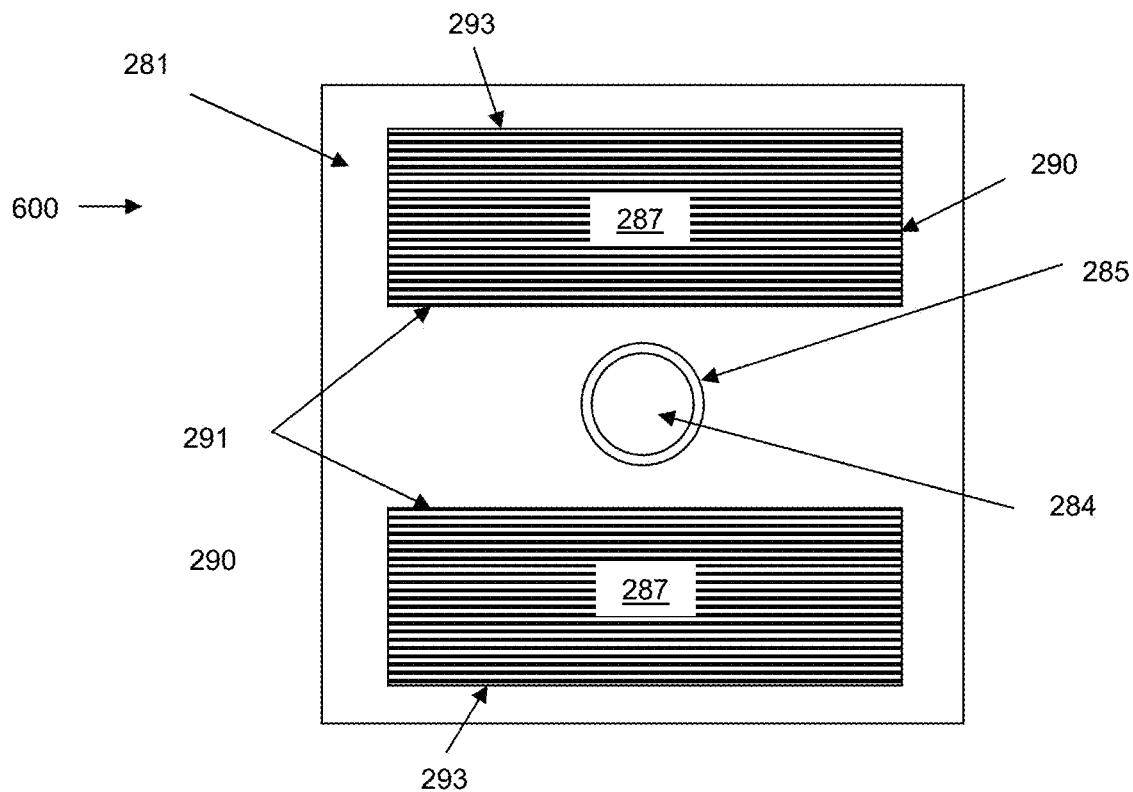
FIG. 38 is a side view of a coated transducer according to an embodiment of the present invention.

In one embodiment illustrated at FIGS. 37 and 38, a partially coated transducer 600 comprising a cylindrical transduction element 281 has one, two, three, four or more coated regions 287. In various embodiments, the coated region 287 has a lateral edge 293, a side edge 290, and a medial edge 291. In some embodiments, the coated region 287 is configured to position one, two, three, four, or more (e.g., multiple) thermal treatment zones through poling, phasic poling, biphasic poling, and/or multi-phasic poling. Various embodiments of ultrasound treatment and/or imaging devices with of multiple treatment zones enabled through poling, phasic poling, biphasic poling, and/or multi-phasic poling are described in U.S. application Ser. No. 14/193,234 filed on Feb. 28, 2014, which is incorporated in its entirety by reference herein.

Non-Therapeutic Uses of a Coated Cylindrical Transducer with Reduced Edge Effects In various embodiments, a coated cylindrical transducer 600 comprising one or more coated regions 287 is configured for non-therapeutic use.

In one embodiment, a coated cylindrical transducer 600 comprising one or more coated regions 287 is configured for materials processing. In one embodiment, a coated cylindrical transducer 600 comprising one or more coated regions 287 is configured for ultrasonic impact treatment for the enhancement of properties of a material, such as a metal, compound, polymer, adhesive, liquid, slurry, industrial material.

In one embodiment, a coated cylindrical transducer 600 comprising one or more coated regions 287 is configured for material heating. In various embodiments, the cylindrical transducer 600 is configured for cooking, heating, and/or warming materials, food, adhesives or other products.

Heating Tissue and Quantification of Thermal Dose for Ultrasound Band Therapy

As described above, in various embodiments, systems and/or methods provide non-invasive dermatological treatment to tissue through heating, hyperthermia, thermal dosimetry, thermal treatment, coagulation, ablation, apoptosis, lysis, increasing tissue volume, decreasing or reducing tissue volume, and/or tissue tightening. In one embodiment, dermal tissue volume is increased. In one embodiment, fat tissue volume is reduced, or decreased.

In various embodiments, band treatment involves metrics that quantify the magnitude of adipocyte death with heat. For example, in one embodiment, thermal dosage in a heat treatment relates time-temperature curves back to a single reference temperature, e.g. T=43 degrees Celsius, using the Arrhenius equation. In one embodiment, a band treatment is configured under a relationship that that for every 1 degree Celsius increase in tissue temperature above in a range above body temperature, the rate of cell death doubles. A theoretical survival fraction can then be determined by comparing the thermal dose to empirical data from the literature.

In various embodiments, band treatment provides improved thermal heating and treatment of tissue compared to diathermy or general bulk heating techniques. In general, normal body temperatures tend to range between about 33-37 degrees Celsius. In various embodiments, as tissue is heated in a range of about 37-43 degrees Celsius, physiological hyperthermia can take place, and exposure to this temperature range on order of, for example, a few hours, can result in increased normal tissue metabolism and/or increased normal tissue blood flow, and in some embodiments, accelerated normal tissue repair. As temperature in the tissues reaches the higher ~43 degrees Celsius range and/or the tissue is subject to the temperature for longer periods of time (e.g., 2 hours, 3, hours or more) the tissue can experience acute tissue metabolism and/or acute tissue blood flow, and in some embodiments, accelerated normal tissue repair. In one embodiment, heating (e.g., bulk heating) of tissue to a range of about 42-55 degrees Celsius is performed. In various embodiments, heating of tissue to about 43-50 degrees Celsius can be considered adjuvant synergistic hyperthermia, and exposure to this temperature range on order of, for example, a few minutes, can result in immediate or delayed cell death, apoptosis, decreased tumor metabolism, increased tissue oxygen levels, increased tissue damage, increased sensitivity to therapy, vascular status, DNA damage, cell reproductive failure, and/or cell destruction. In various embodiments, heating of tissue to about 50-100 degrees Celsius can be considered surgical hyperthermia, and exposure to this temperature range on order of, for example, a few seconds or fractions of a second, can result in coagulation, ablation, vaporization, and immediate cell destruction.

In some embodiments of the invention, the temperature of the tissue treatment site (e.g., the adipocytes) is elevated to 38-43 degrees Celsius, and according to one embodiment, thereby increasing tissue metabolism and perfusion and accelerating tissue repair mechanisms. In other embodiments, the temperature of the tissue treatment site (e.g., the adipocytes) is elevated to 43-50 degrees Celsius, which in one embodiment can increase cell damage starts and result in immediate cell death, particularly when the temperature remains elevated on the order of several minutes to an hour (or longer). In yet other embodiments, the temperature of the tissue treatment site (e.g., the adipocytes) is elevated to above 50 degrees Celsius, which in one embodiment results in protein coagulation on the order of seconds and less and can lead to immediate cell death and ablation. In various embodiments, the temperature of the tissue treatment site is heated to 40, 41, 42, 43, 44, 45, 46, 47, 48, 49, 50, 51, 52, 53, 54, 55, 56, 57, 58, 59, 60, 61, 62, 63, 64, 65, 70, 75, 80, 90, or 100 degrees Celsius, and/or any range therein. In various embodiments, a treatment area has uniform temperature, a variance of 1%, 2%, 3%, 4%, 5%, 6%, 7%, 8%, 9%, 10%, 12%, 15%, 20%, 25%, 30%, 40%, 50% or more. In various embodiments, a treatment area has a variance of +/−0, 1, 2, 3, 4, 5, 6, 7, 8, 9, 10, 12, 15, 20, 25 degrees Celsius or more.

In several embodiments, the invention comprises elevating the temperature of the tissue treatment site (e.g., the adipocytes) is elevated to 38-50 degrees Celsius for a time period between 1-120 minutes, and then optionally increasing the temperature in one, two, three, four five or more increments by 10-50%. As an example using three increments, the target temperatures may be increased as follows: (i) elevate temperature to about 40-42 degrees Celsius for 10-30 minutes, (ii) then optionally increase temperature by about 20% to elevate temperature to about 48-51 degrees Celsius for 1-10 minutes, and (iii) then optionally increase by about 10-50% for a shorter time frame. As another example, the target temperature may be increased as follows: (i) elevate temperature to about 50 degrees Celsius for 30 seconds to 5 minutes (e.g., about 1 minute) to destroy over 90%, 95% or 99% of target (e.g., adipose) cells, with an optional pre-heating step of raising the temperature to 38-49 degrees Celsius for a period of 10-120 minutes prior to the elevation to 50 degrees Celsius. As yet another example, in some embodiments, a non-invasive, cosmetic method of heating tissue, comprises applying a cosmetic heating system to a skin surface, wherein the cosmetic heating system comprises a hand-held probe, wherein the hand-held probe comprises a housing that encloses an ultrasound transducer configured to heat tissue below the skin surface to a tissue temperature in the range of 40-50 degrees Celsius, wherein the ultrasound transducer comprises a cylindrical transduction element comprising a first surface, a second surface, a coated region, and an uncoated region, wherein the coated region comprises an electrical conductor, wherein the first surface comprises at least one coated region, wherein the second surface comprises the uncoated region and a plurality of coated regions, applying a current to the plurality of coated regions, thereby directing ultrasound energy to a linear focal zone at a focal depth, wherein the ultrasound energy produces a reduction in focal gain at the linear focal zone, thereby heating the tissue at the focal depth in the linear focal zone to the tissue temperature in the range of 40-50 degrees Celsius for a cosmetic treatment duration of less than 1 hour, thereby reducing a volume of an adipose tissue in the tissue.

In one embodiment, a band therapy system uses a relationship between cell death and time-temperature dosages as quantified using the Arrhenius equation. The Arrhenius equation shows an exponential relationship exists between cell death and exposure time and temperature. Above a certain break temperature, the increase in the rate of cell killing with temperature is relatively constant. Time-temperature relationships to achieve isoeffective dose in several types of tissue appears to be conserved both in vitro and in-vivo across multiple cell types.

In some embodiments, clinical situations involve ramp-up of temperatures, cooling, and fluctuations when approaching and maintaining a steady state temperature. In various embodiments, different thermal profiles can produce the same thermal dose. In order to estimate the thermal dosage from a time-varying thermal profile, a temperature curve is discretized into small time steps, and the average temperature during each time step is calculated. The thermal dosage is then calculated as an equivalent exposure time at the break temperature (43 degrees Celsius) by integrating these temperatures according to equation (2):

$$t_{43} = \sum_{t=0}^{t=final} R^{(43-\overline{T})} \Delta t \tag{2}$$

$t_{43}$: Equivalent time at 43°C.

$\overline{T}$: Average temperature during $\Delta t$ $$R = \begin{Bmatrix} 0.5, \ T \geq 43°C. \\ 0.25, \ T < 43°C. \end{Bmatrix}$$

Figure 39:
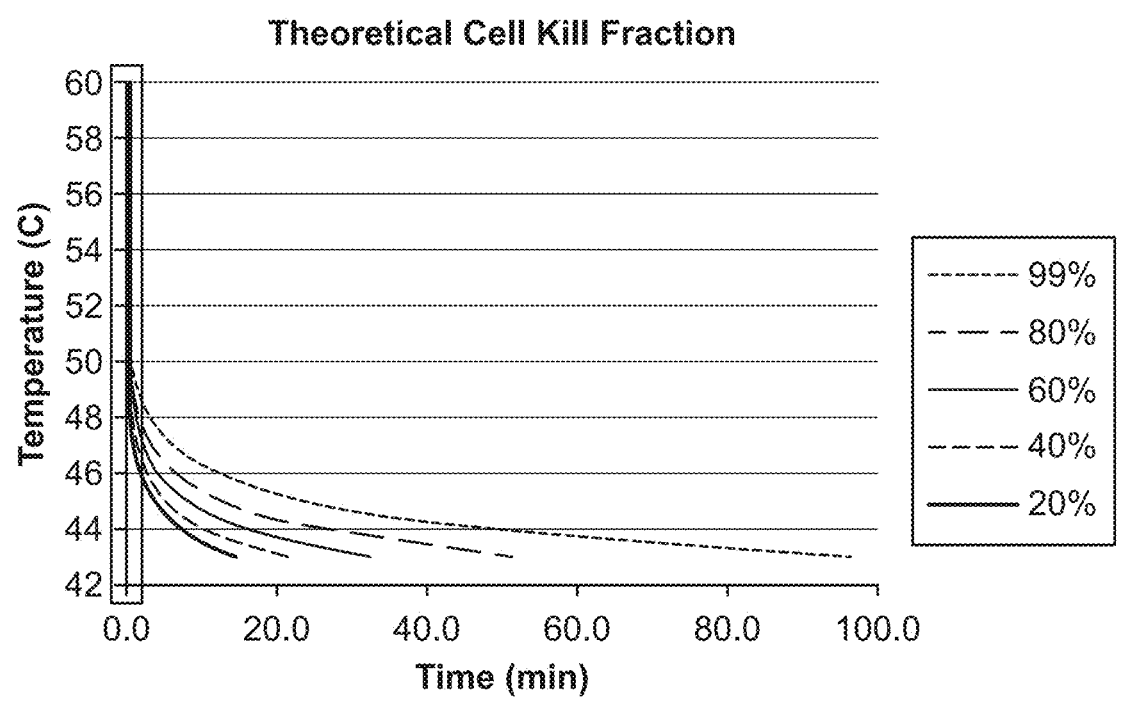
FIG. 39 illustrates a charts relating time and temperature to attain various theoretical cell kill fractions according to an embodiment of the present invention.
Figure 40:
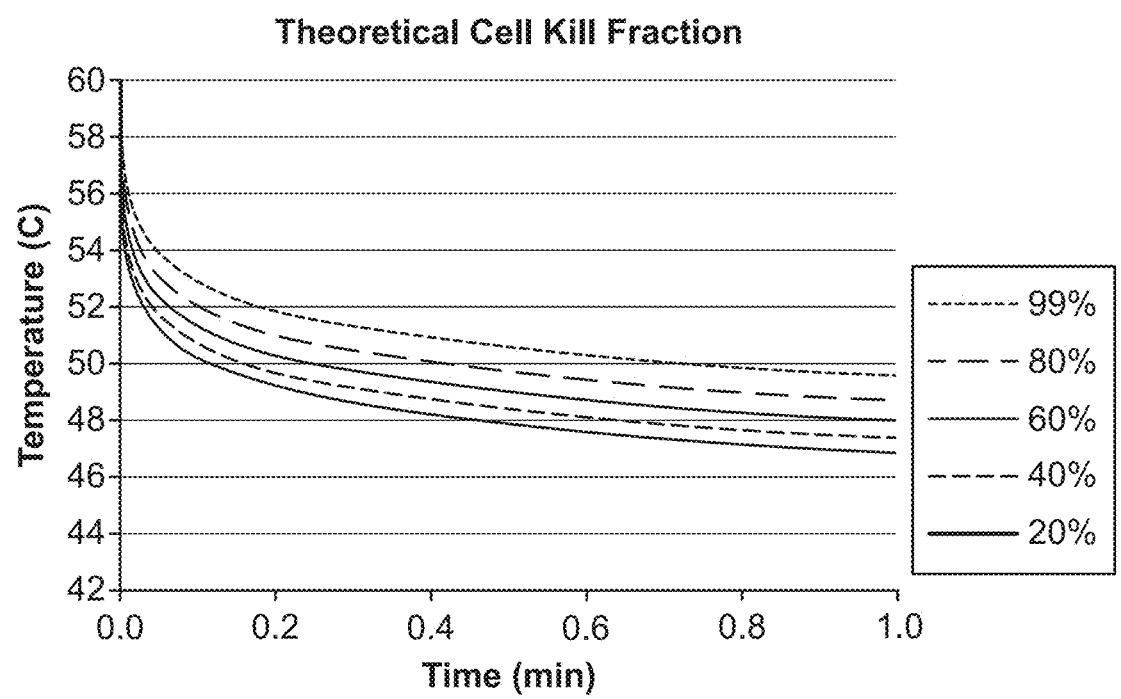
FIG. 40 illustrates charts relating time and temperature to attain various theoretical cell kill fractions according to an embodiment of the present invention.

Equation (2) suggests that the increase in the rate of killing with temperature is relatively constant. In some embodiments, a 1 degree Celsius increase above a break point results in the rate of cell death doubles. FIGS. 39 and 40 illustrate theoretical cell death fractions over time depending on tissue temperature, with higher theoretical cell killing fractions at higher temperatures and/or higher periods of time. The higher a kill fraction (such as shown with kill fractions of 99%, 80%, 50%, 40%, and 20%) the higher a temperature and/or a time is used in an embodiment of a treatment.

Once a thermal dose has been calculated, a dose survival response can be estimated from empirical data. In one embodiment, an isoeffective dose of 43 degrees Celsius for 100 minutes theoretically yields a cell survival fraction of 1%. Based on the Arrhenius relationship, a similar surviving fraction can be obtained with an isoeffective dose of 44 degrees Celsius for 50 minutes, or 25 minutes at 45 degrees Celsius, etc. as tabulated in the table listing isoeffective dosages to theoretically achieve 1% survival fraction at FIG. 41, according to embodiments of the present invention.

In various embodiment, simulations of various embodiments of band therapy using a cylindrical transducer source conditions linked to the relationship between tissue and heat equation showed that successive treatment pulses obey linear superposition, which allows for simplification of the heat transfer physics so that the heating rate may be described as a temperature rise per time (degrees Celsius/sec), and as a temperature rise per pass (degrees Celsius/button push).

Heating Tissue Via Ultrasound Band Therapy

Figure 42:
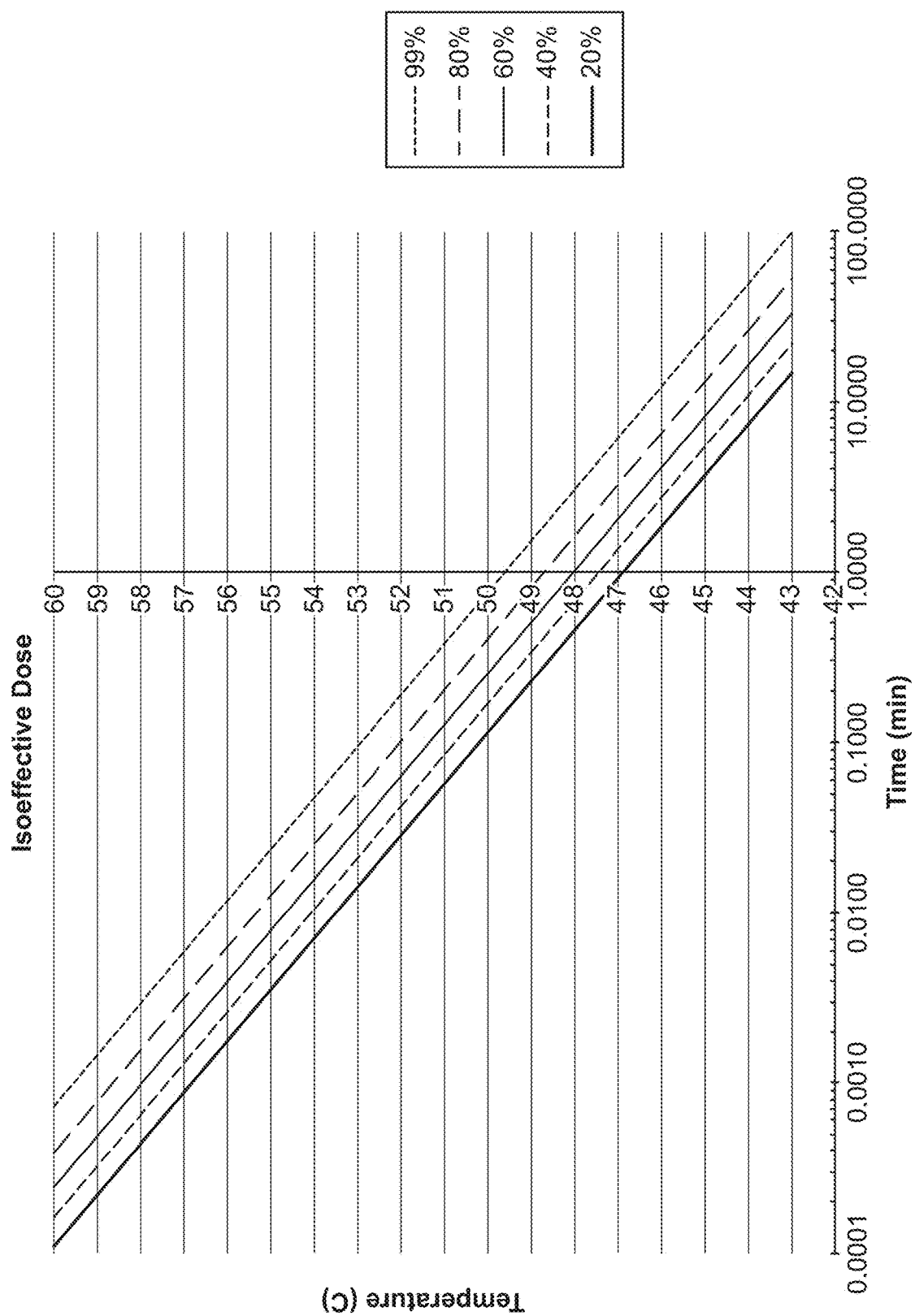
FIG. 42 is a chart relating time and temperature for isoeffective doses applied for surviving fraction of cells according to an embodiment of the present invention.

In various embodiments, a band therapy system is configured for treating the tissue. For example, in one embodiment, a band treatment is configured for treatment of supraplatysmal submental fat. In one embodiment, a treatment of fat includes selectively causing thermal heat shock followed by apoptosis to a fat layer, at a depth of about 2.5-6.0 mm, without causing any major skin surface effects. In one embodiment, the treatment involves exposing fat to a bulk heating treatment with a temperature of 42-55 degrees Celsius for 1-5 minutes without exceeding 41 degrees Celsius on the skin surface, with physiologic/biologic effect (e.g. one or more of coagulation, apoptosis, fat cell lysis, etc.). In various embodiments, treatment with a band transducer treats tissue with isoeffective doses, as shown in a graph representing various levels of theoretical cell kill fractions in FIG. 42.

Figure 43:
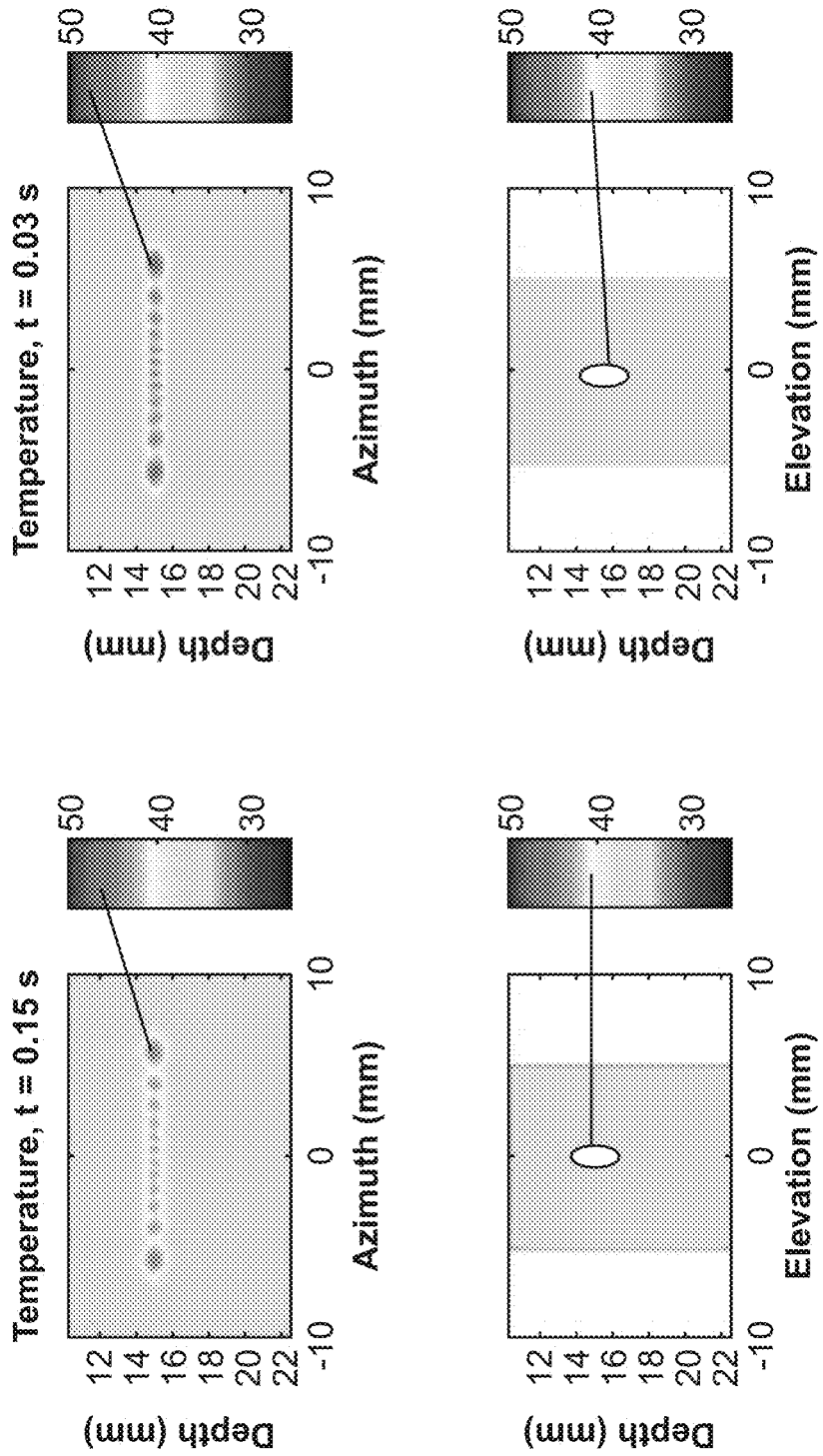
FIG. 43 illustrates simulations of cylindrical transducer output showing linear superposition of multiple pulses according to an embodiment of the present invention.

In various embodiments, a theoretical review of the effect of stacking multiple treatment pulses using the Khokhlov-Zabolotskaya-Kuznetsov (KZK) Equation was implemented with cylindrical source acoustic geometry, linked to a bio-heat equation (e.g., in one embodiment, using the Arrhenius equation). FIG. 43 shows the results of a KZK simulation of cylindrical transducer output showing linear superposition of multiple pulses; approximately the same temperatures are reached when treating with 3 pulses of 0.45 J or 1 pulse of 1.35 J (3*0.45 J). The results of a theoretical experiment with one embodiment of a band therapy system as shown in FIG. 43, suggest non-linear acoustics are not a major contributor to the final temperature for the energies, and suggests that body tissue acts as a linear time-invariant system, which allows for simplification of the heat transfer physics, and the heating and cooling rates to be described in relatively few parameters. In various embodiments, a therapy system with a hand wand 100 includes a module 200 with one or more ultrasound transducers 280. In some embodiments, an ultrasound transducer 280 includes one or more cylindrical ultrasound elements 281, as shown in FIGS. 5A-8. The cylindrical transducer element 281 is configured for bulk heating treatments with its linear focus along an axis, resulting in a continuous line that can be moved with an automated motion mechanism to treat a rectangular plane. In one embodiment, lines of treatment are deposited perpendicular to the direction of motor movement in a single direction. A single "pass" of treatment creates a number of therapy lines equal to {Length}/{Spacing}.

Figure 44:
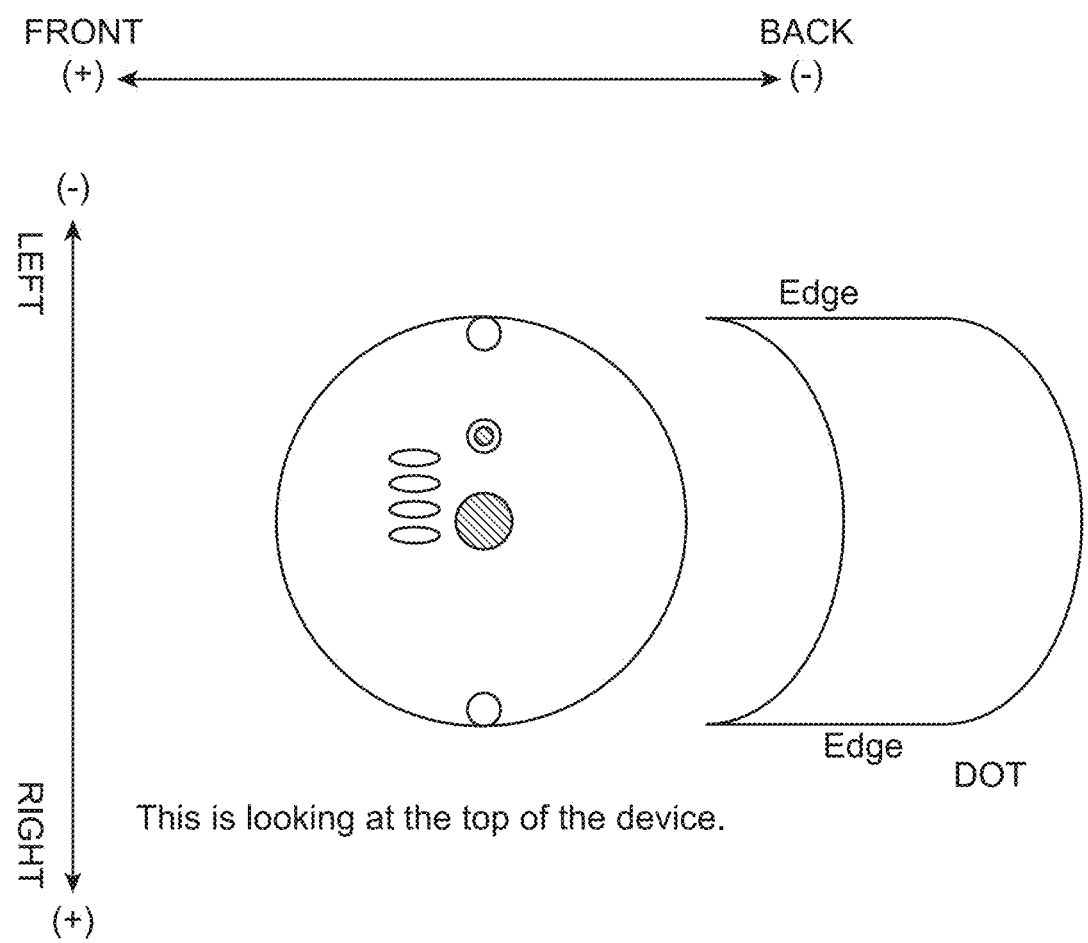
FIG. 44 is a top view of an apodized transducer according to an embodiment of the present invention.
Figure 45:
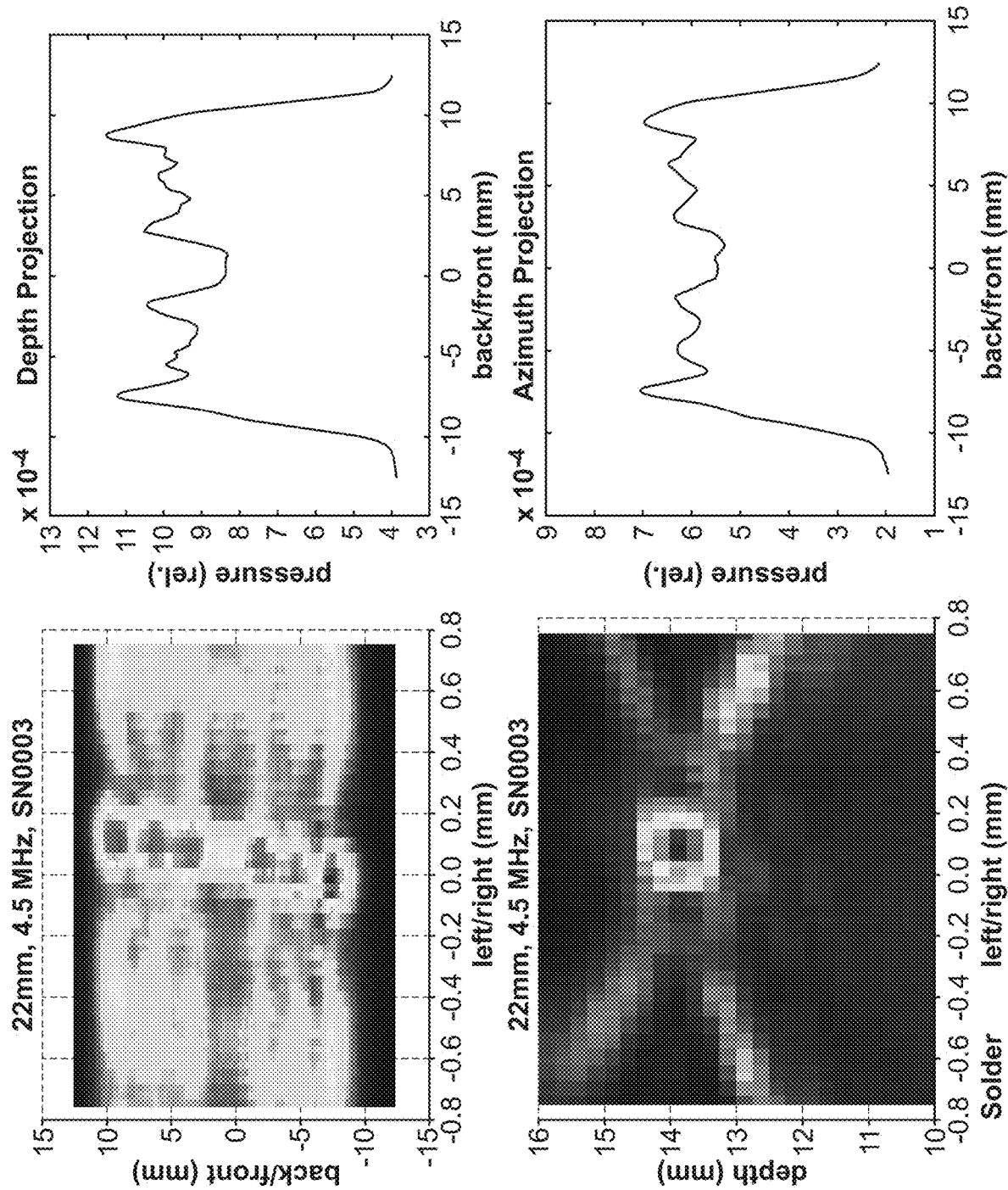
FIG. 45 illustrates acoustic pressure profiles with an apodized transducer according to the embodiment of FIG. 44.

In various embodiments, various cylindrical geometries were tested from the first build (4.5 MHz-12 mm width at 4.5 mm and 6.0 mm depths); however, acoustic tank testing showed higher acoustic pressures (and therefore heating rates) at the each edge of the therapy line. In one embodiment, a ceramic transducer was apodized to produce a flat thermal profile, as shown in FIGS. 44 and 45. In various embodiments, different cylindrical geometries based on two operating frequencies, two treatment widths, and two treatment depths were built: (1) 3.5 MHz-22 mm Width-4.5 mm Depth; (2) 3.5 MHz-22 mm Width-6.0 mm Depth; (3) 4.5 MHz-22 mm Width-4.5 mm Depth; (4) 4.5 MHz-22 mm Width-6.0 mm Depth; (5) 3.5 MHz-12 mm Width-4.5 mm Depth; (6) 4.5 MHz-12 mm Width-4.5 mm Depth; (7) 3.5 MHz-12 mm Width-6.0 mm Depth; and (8) 4.5 MHz-12 mm Width-6.0 mm Depth. In various embodiments, a tissue temperature measurement system included one or more of including IR thermography, temperature strips, and resistance temperature detectors (RTDs), and thermocouples. IR thermography can be used to read skin surface temperatures. Temperature strips are able to provide peak temperature reached. RTD sheaths have a large thermal mass and may have a slow response time. In various embodiments, thermocouples have a response time less than a second, which is helpful for measuring the heating and cooling phase of a single treatment pass. Thermocouples also have the advantage of being small enough that they can be positioned through a large bore needle to the desired tissue depth. In one embodiment, a particular isoeffective dose is attached via the heating phase followed by a maintenance phase in which the system or an operator pulses treatment at an interval to sustain a steady state temperature. A parameter of interest during this phase is the average pulse period needed to maintain the steady state temperature.

Body Contouring Via Ultrasound Band Therapy

In various embodiments, a band therapy system is configured for body contouring. In one embodiment, body contouring treatment involves thermal heat shock concurrent with, and/or followed by apoptosis. In one embodiment, body contouring treatment involves exposing fat to 42-55 degrees Celsius for 1-5 minutes to induce delayed apoptosis. In one embodiment, body contouring treatment involves exposing fat at a focus depth of at least 13 mm below the skin surface.

Temperature and Dose Control

In various embodiments, one or more sensors may be included in the module 200 or system 20 to measure a temperature. In one embodiment, methods of temperature and/or dose control are provided. In one embodiment, temperature is measured to control dosage of energy provided for a tissue treatment. In various embodiments, a temperature sensor is used to measure a tissue temperature to increase, decrease, and/or maintain the application of energy to the tissue in order to reach a target temperature or target temperature range. In some embodiments, a temperature sensor is used for safety, for example, to reduce or cease energy application if a threshold or maximum target temperature is reached. In one embodiment, a cooling device or system can be employed to cool a tissue temperature if a certain temperature is reached. In some embodiments, a temperature sensor is used to modulate an energy dose, for example, via modulation, termination of amplitude, power, frequency, pulse, speed, or other factors.

In one embodiment, a temperature sensor is used to measure a skin surface temperature. In one embodiment, a temperature sensor may be positioned on top of the transducer holder and a sensor may be located in a portion of the module, or vice versa (swapped). In various embodiments, a temperature sensor is positioned on a system or module housing, such as in one embodiment, near or on an acoustic window, such as an acoustically transparent member 230. In one embodiment, one or more temperature sensors are positioned around or proximate an acoustically transparent member 230. In one embodiment, one or more temperature sensors are positioned in or on an acoustically transparent member 230. In one embodiment, a temperature sensor measure from a skin surface can be used to calculate a temperature in a tissue at the focus depth of the energy application. In various embodiments, a target tissue temperature can be calculated and/or correlated to the depth in tissue, type of tissue (e.g. epidermis, dermis, fat, etc.) and relative thickness of tissue between the skin surface and the focus depth. In some embodiments, a temperature sensor provides a temperature measurement for a signal to a control system. In some embodiments, a temperature sensor provides a temperature measurement for visual and/or auditory feedback to a system operator, such as a text, color, flash, sound, beep, alert, alarm, or other sensory indicator of a temperature state.

In some embodiments, imaging can be used to control energy dose. In one embodiment, a thermal lens effect can be used to account for speckle shift and/or feature shift to indicate a temperature of a tissue at a target location, such as at a focus depth in tissue below the skin surface. In one embodiment, Acoustic Radiation Force Impulse (ARFI) imaging is used to calculate a tissue temperature. In one embodiment, Shear Wave Elasticity Imaging (SWEI) is used to calculate a tissue temperature. In one embodiment, attenuation is used to calculate a tissue temperature.

In various embodiments, a variable dose delivery technique is used to attain a target temperature in a tissue and maintain that target temperature. The body temperature at a depth in tissue surrounds a thermal treatment zone (TTZ). In one embodiment, to overcome the body temperature, a treatment focuses energy at the TTZ at a first rate to bring the tissue temperature in the TTZ to a target temperature. Once that target temperature is attained, the second rate can be reduced or stopped to maintain the tissue at the target temperature.

Figure 53:
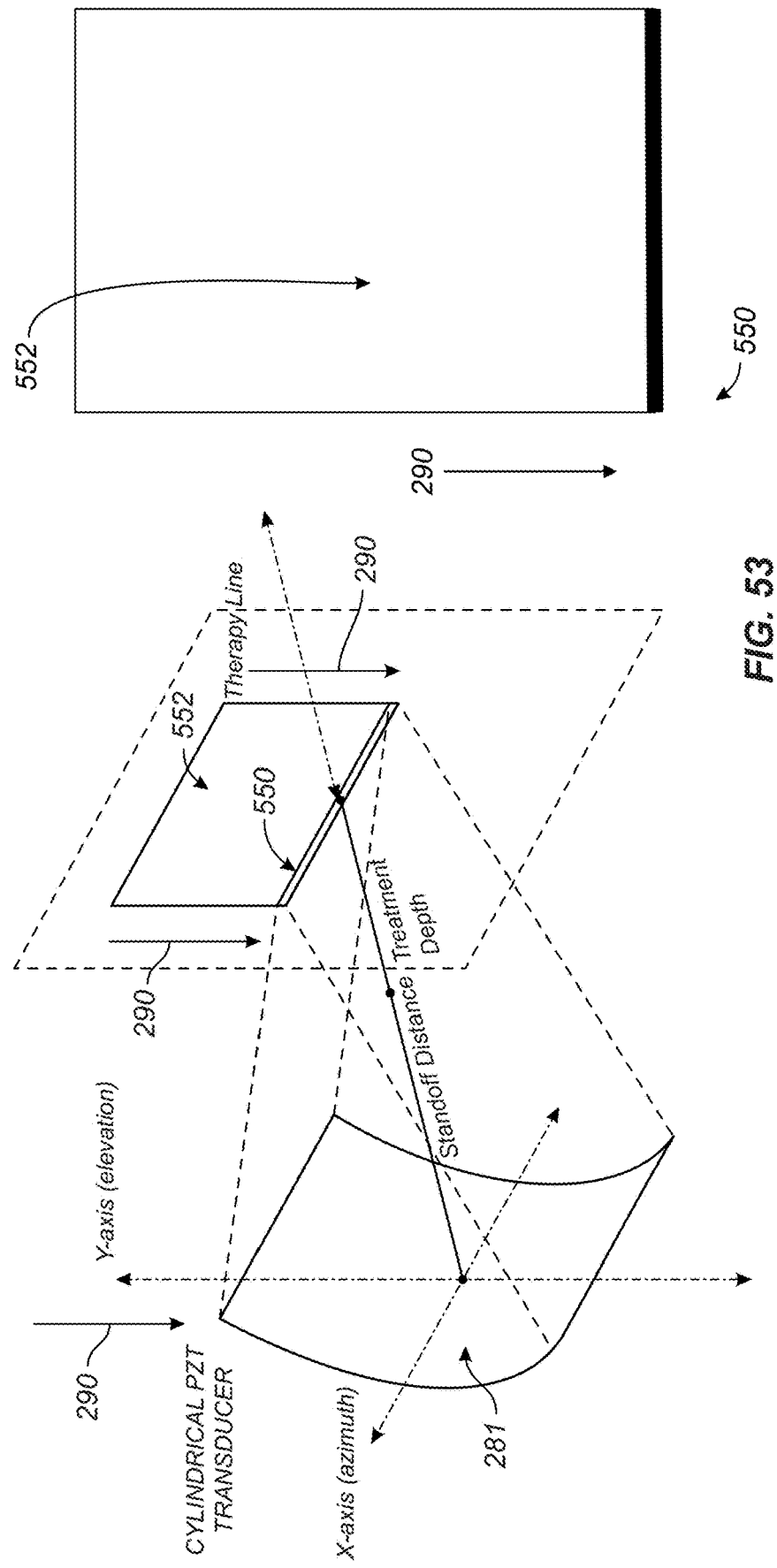
FIG. 53 is an isometric side view of a transducer and treatment area according to an embodiment of the present invention.

In some embodiments, energy is focused at a depth or position in tissue at the TTZ, such that the temperature in the focal zone is increased. However, at the edges (e.g., ends, top, bottom, sides, etc.) of the focal zone, a boundary condition at body temperature can result in temperature fluctuations at the boundaries of the treatment area 552. In various embodiments, movement of the TTZ 550 can be with the transducer delivering energy to create a treatment area 552. In one embodiment, a movement mechanism 285 can automatically move the cylindrical transduction element 281 across the surface of a treatment area so that the TTZ 550 can form a treatment area 552. In FIG. 53, the treatment area 552 is surrounded at the edges by body temperature, or approximately body temperature. In some embodiments, the temperature in the treatment area 552 along the edges/boundary are lower than the desired, target temperature.

Figure 54:
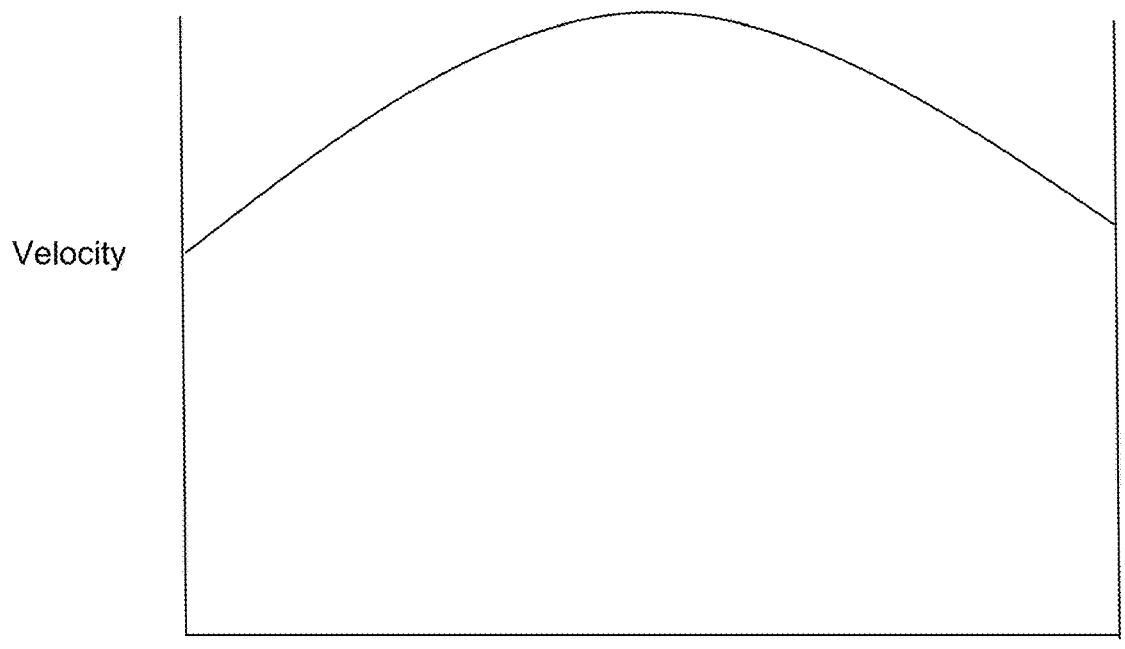
FIG. 54 is a chart illustrating velocity and position along an axis according to an embodiment of the present invention.

In various embodiments, mechanical velocity modulation is used to attain a specific thermal distribution in the treatment area 552. In one embodiment, in order to attain a more uniform temperature in the treatment area 552, the applied temperature at the edges/boundaries is increased to counteract the surrounding body temperature difference. FIG. 54 illustrates an embodiment of mechanical velocity modulation in which the velocity, or speed of the automatic motion of the motion mechanism moving the transducer along direction 290 (along the elevation direction), is varied to provide a more uniform temperature in the treatment area 552 by slowing near the boundaries, resulting in increased temperature at the boundaries (start and stop position, such as along a 25 mm travel distance, in one embodiment). The increased velocity near the middle delivers a lower temperature than the decreased velocity.

Figure 55:
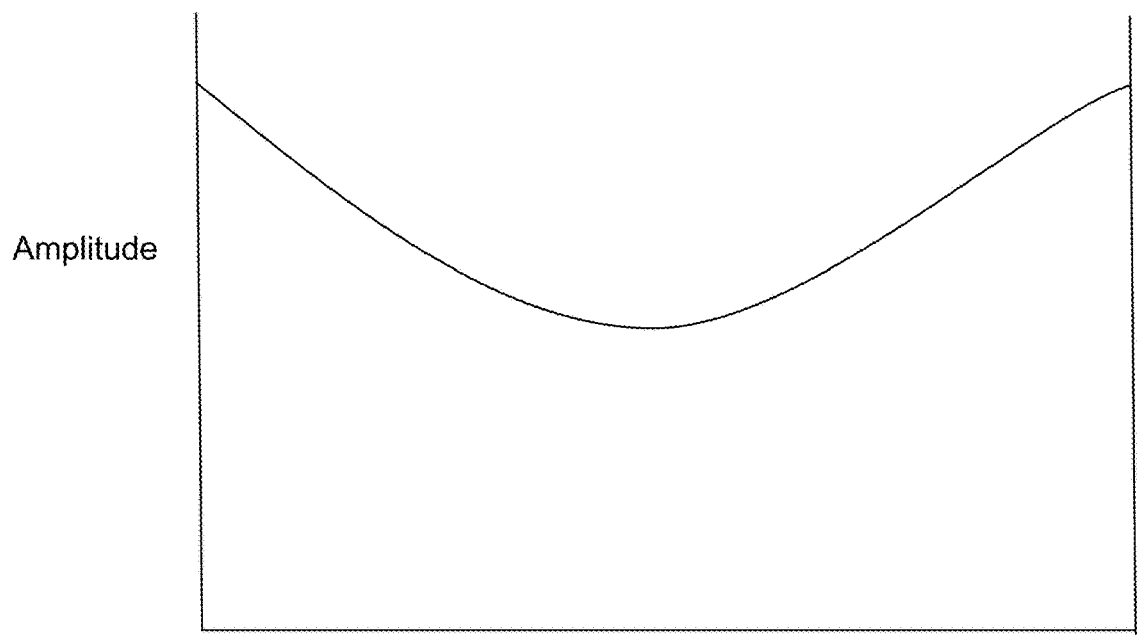
FIG. 55 is a chart illustrating velocity and position along an axis according to an embodiment of the present invention.

In various embodiments, amplitude modulation is used to attain a specific thermal distribution in the treatment area 552. In one embodiment, in order to attain a more uniform temperature in the treatment area 552, the applied temperature at the edges/boundaries is increased to counteract the surrounding body temperature difference. FIG. 55 illustrates an embodiment of amplitude modulation in which the amplitude (correlates to power) of the energy delivered by the transducer as the automatic motion of the motion mechanism moves along direction 290 (along the elevation direction), is varied to provide a more uniform temperature in the treatment area 552 by increasing amplitude near the boundaries, resulting in increased temperature at the boundaries (start and stop position, such as along a 25 mm travel distance, in one embodiment). The lower amplitude near the middle delivers a lower temperature than the higher amplitude near the boundaries.

Figure 56:
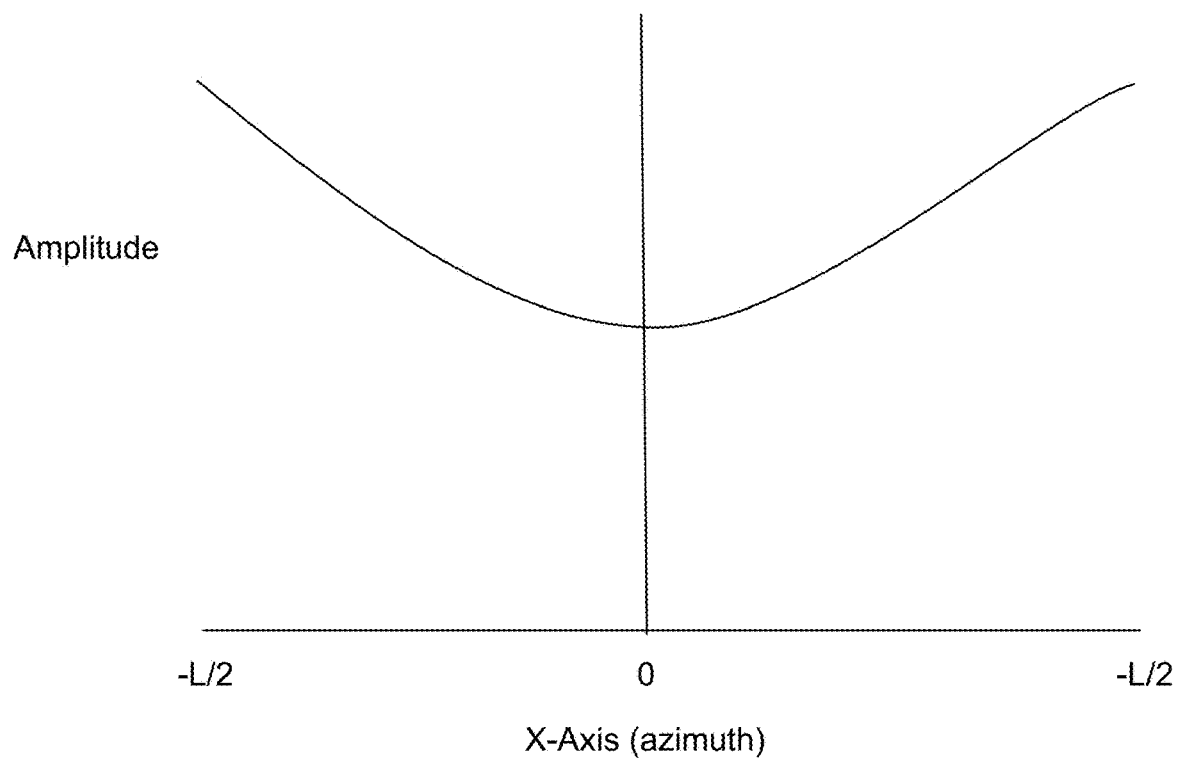
FIG. 56 is a chart illustrating amplitude and position along an axis according to an embodiment of the present invention.

In various embodiments, aperture apodization is used to attain a specific thermal distribution in the treatment area 552. In one embodiment, aperture apodization along the non-focused dimension (such as along TTZ 550 and/or the azimuth direction) is used in order to attain a more uniform temperature in the treatment area 552. The applied temperature at the end points, along the edges/boundaries is increased to counteract the surrounding body temperature difference. FIG. 56 illustrates an embodiment of aperture apodization in which the amplitude of the energy delivered by the transducer along the TTZ 550 is varied to provide a more uniform temperature in the treatment area 552 by increasing amplitude near the end points near the boundaries, resulting in increased temperature at the boundaries (with L as a length of the focused line TTZ 550, L/2 from center is the end point). The lower amplitude near the middle delivers a lower temperature than the higher amplitude near the boundaries. In various embodiments, a temperature profile can be generated along the TTZ with embodiments of a coated transduction element 600, such as illustrated in FIGS. 31-38.

Figure 57:
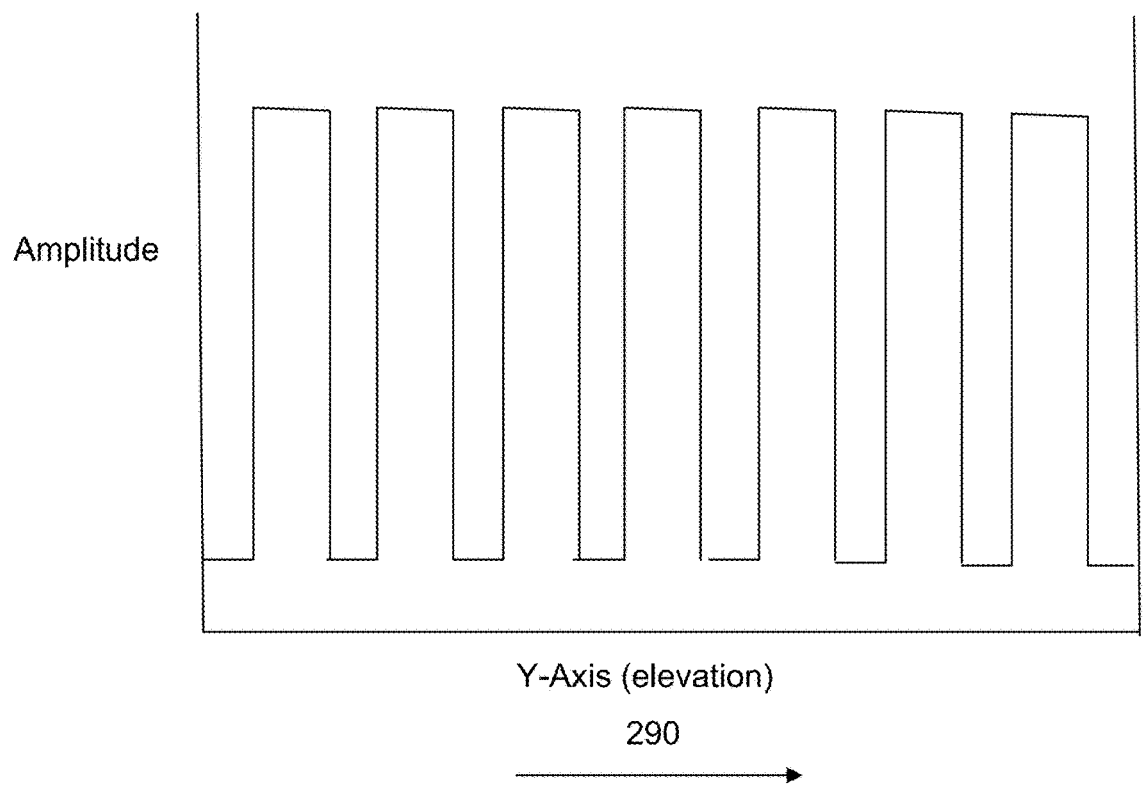
FIG. 57 is a chart illustrating velocity and position along an axis according to an embodiment of the present invention.

In various embodiments, pulsing and/or duty cycles are controlled to attain a specific thermal distribution in the treatment area 552. At FIG. 57, in various embodiments, treatment patterns can have a consistent or a constant pulsing or duty cycle. At FIG. 58, in various embodiment, treatment patterns can have variable pulsing or a variable duty cycle, with variations in any of peak amplitude, spacing of application, duration of application. As shown in FIG. 58, the application of energy is longer and covers more area near the boundary of the treatment area 552, while the internal region has less power application for a corresponding lower temperature application in the internal region.

In various embodiments, treatment patterns are used to attain a specific thermal distribution in the treatment area 552. In some embodiments the TTZ 550 has a dimension (e.g., width, height, thickness, etc.). In some embodiments, the pulsed application of TTZ 550 is non-overlapping, as shown in FIG. 59. In some embodiments, the pulsed application of TTZ 550 is overlapping, as is shown near a boundary in FIG. 60, where the amount of overlapping can be constant or vary. As shown in the embodiment in FIG. 60, the amount of overlap varies and includes a non-overlapping portion. In various embodiments, a cross hatching pattern is used, wherein the system hand piece is rotated about 90 degrees, or orthogonally, and the motion mechanism is operated in one or more additional passes over a target tissue region in an orthogonal direction to a prior treatment pass.

Figure 61:
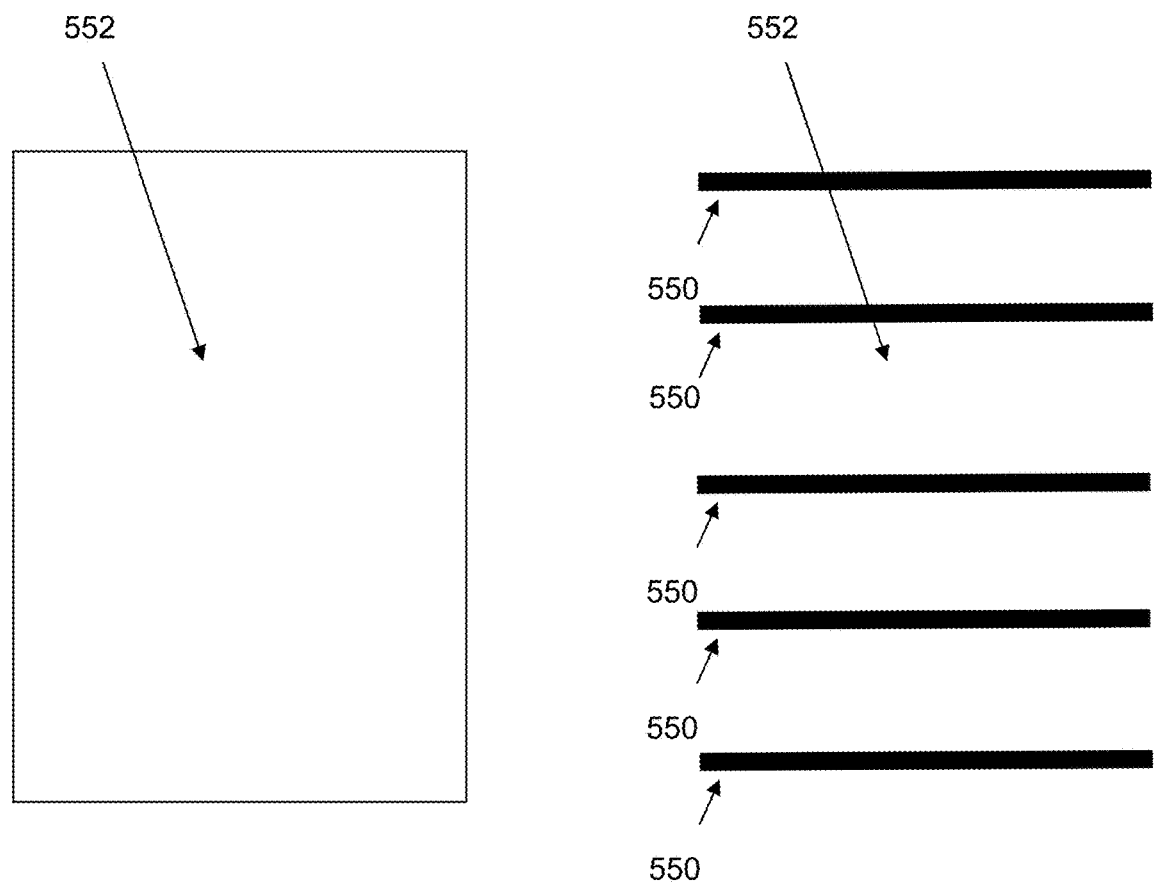
FIG. 61 illustrates a treatment area according to various embodiments of the present invention.

In various embodiments, a specific thermal distribution in the treatment area 552 comprises treatment with a tissue temperature of 37-50 degrees Celsius for a duration of minutes to hours to cause a targeted percentage of cell death (such as fat cell death) which a relationship can be determined via Arrhenius equation, such as is shown on the left side of FIG. 61. In various embodiments, a specific thermal distribution in the treatment area 552 comprises treatment with a tissue temperature of over 60 degrees Celsius for a duration of seconds to fractions of a second (or near instantaneous) coagulation, ablation, and/or cell death (such as fat cell death) at the elevated temperature, such as shown on the right side of FIG. 62. In various embodiments, a treatment can be either one, or both in sequence and/or simultaneous treatments.

In some embodiments, one, two, three, four, or more of mechanical velocity modulation, amplitude modulation, aperture apodization, pulsing duty cycles, and/or treatments at different temperatures can be used to achieve a desired temperature profile across the treatment area 552. In various embodiments, one or more of mechanical velocity modulation, amplitude modulation, aperture apodization, pulsing duty cycles, and/or treatments at different temperatures is used to create a temperature profile, wherein the temperature profile can include areas for increased, decreased, and/or uniform temperatures. In some embodiments, one, two, or more types of treatment are applied in one, two, or three dimensions (along any of the azimuth, elevation, and/or depth directions) and is configured for treatment in any of one, two, or three dimensions to create a one, two, or three dimensional temperature profile.

Figure 62:
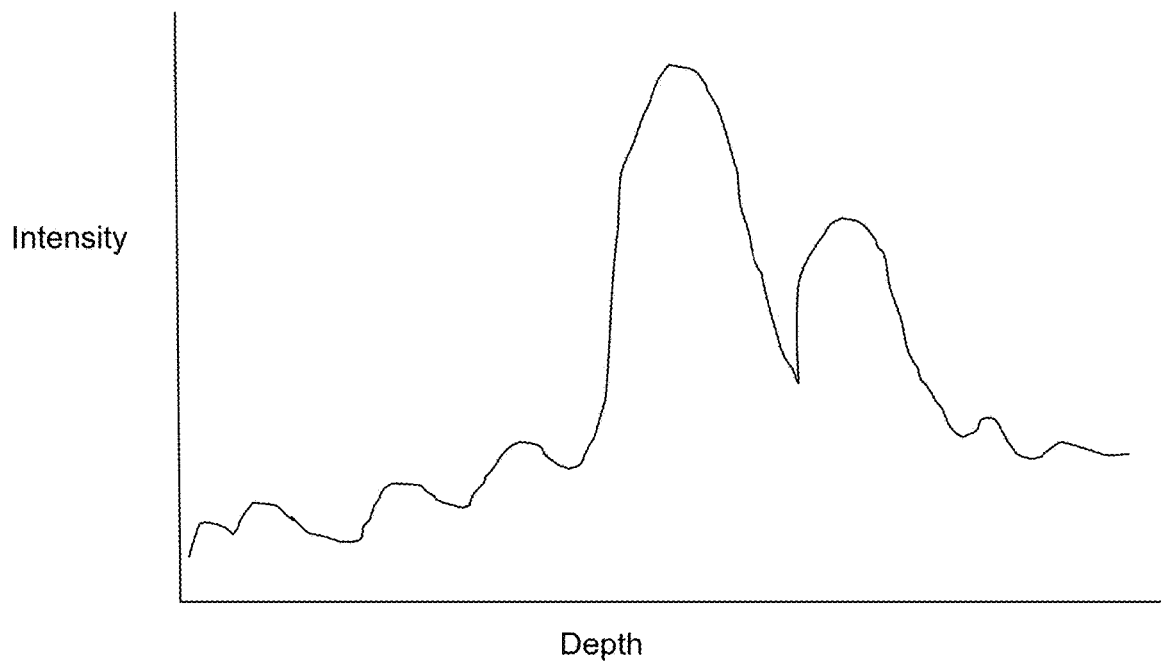
FIG. 62 is a chart illustrating intensity and depth according to an embodiment of the present invention.
Figure 63:
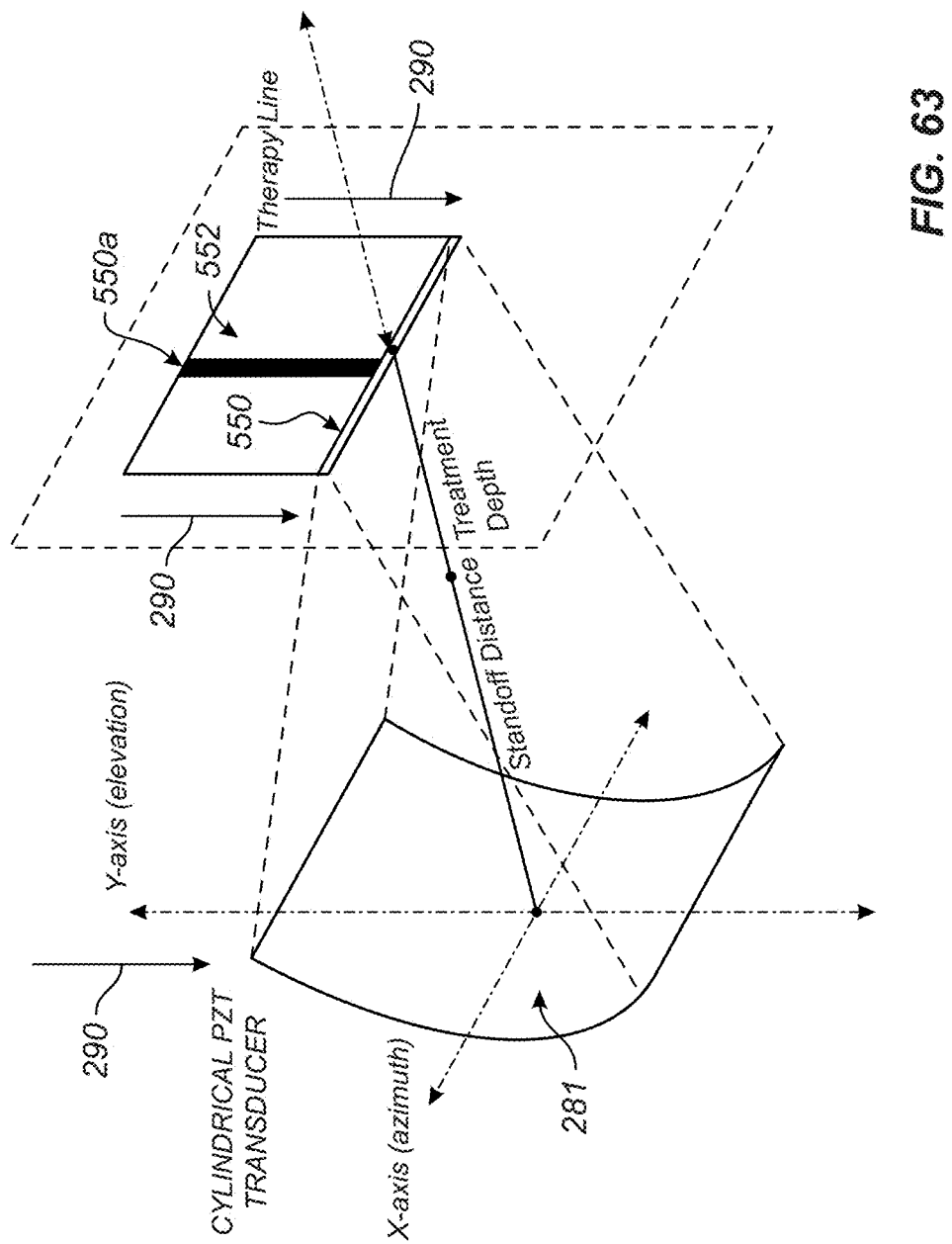
FIG. 63 is an isometric side view of a transducer and treatment area with multiple thermal treatment zones according to an embodiment of the present invention.

In some embodiments, a compound lens system produces various peak intensities and different depths. In various embodiments, a mechanical and/or electronic focus lens can be used in any one or more of the azimuth, elevation, and/or depth directions. As illustrated in FIG. 62 and FIG. 63, a compound lens system can create two or more focal lines 550 and 550a.

Figure 64:
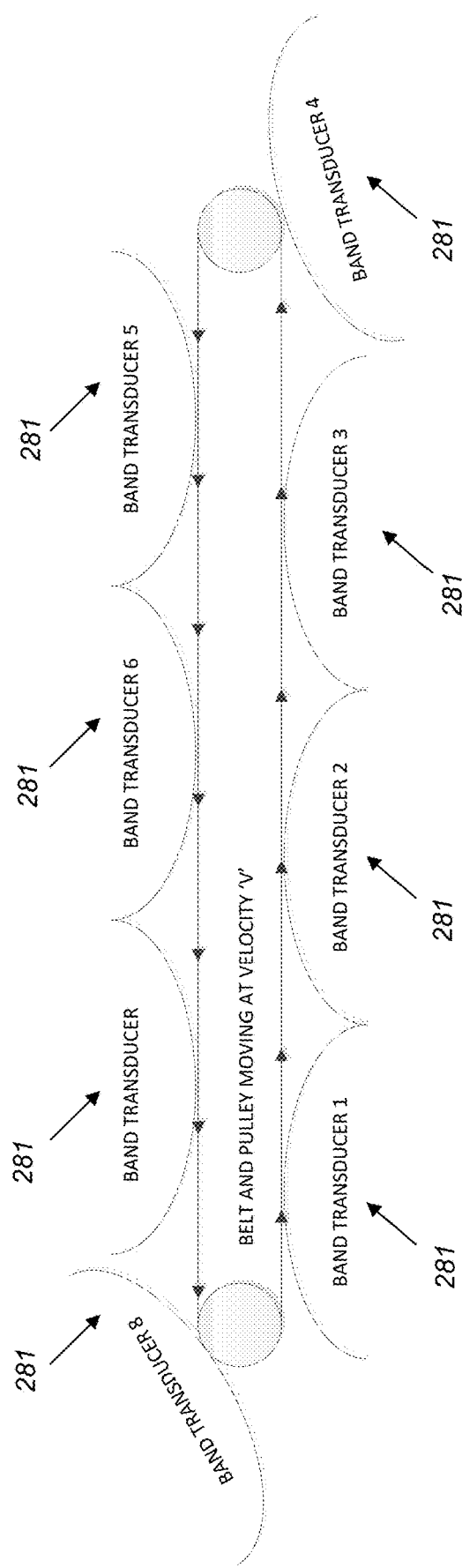
FIG. 64 is a schematic side view of a system comprising a plurality of ultrasound elements on a motion mechanism according to an embodiment of the present invention.

In various embodiments, an ultrasound system 20 comprises a motion mechanism 285 configured for moving a plurality of ultrasound transducers 280 and/or a plurality of ultrasound elements 281. In some embodiments, such as illustrated in an embodiment at FIG. 64, the motion mechanism 285 is configured to minimize heat fluctuation in treated tissue and reduce treatment time by presenting the plurality of elements 281 on a conveyor system, such as with a belt and/or pulley system that can move the plurality of elements 281 at a velocity v. In various embodiments, velocity can be constant, variable, zero (e.g., stopped), reversible (e.g., forward and backward, left and right, first direction and second direction, etc.) and/or have values in the range 0-100 RPM, 1 RPM-50 RPM, or other velocities. In various embodiments, the velocity is any value 1-1,000 cm/second (e.g., 10, 20, 50, 100, 200, 500, 1000 cm/sec, and any other values therein). In various embodiments, the motion mechanism 285 moves one, two, three, four, five, six, seven, eight, or more ultrasound elements 281. In various embodiments, ultrasound elements 281 are connected, or spaced at a distance of 0.01-10 cm apart, (e.g., 0.1, 0.5, 1, 2, 5 cm and any values therein), such that one, two, or more ultrasound elements 281 are configured to treat a treatment area.

In some embodiments, imaging is used to confirm the quality of the acoustic coupling between a treatment device and the skin. In one embodiment, clarity of an ultrasound image along a treatment area, line, or point is used to determine the extent to which a device is acoustically coupled to a skin surface. In one embodiment, defocused imaging and/or Voltage Standing Wave Ratio (VSWR) from backscatter is used to check acoustic coupling for a treatment.

In some embodiments, a treatment is automated. In one embodiment, a treatment is set up by acoustically coupling a system to a skin surface, and the movement mechanism and treatment is automated to function. In various embodiments, the system is coupled to a skin surface via suction. In various embodiments, a system operator couples the system to a skin surface, activates the system, and can leave the system to automatically perform a treatment, or a portion of a treatment. In one embodiment, a system uses suction and/or vacuum pressure to hold a probe or portion of the system to a skin surface, allowing the system user to initiate treatment and leave the system to automatically perform a treatment or a portion of a treatment for a period of time. In some embodiments, a treatment system includes a TENS stimulation device to reduce pain at a skin treatment site.

Theoretical and Experimental Treatments with a Cylindrical Transducer

The following examples illustrate various non-limiting embodiments.

Example 1

The following example is intended to be a non-limiting embodiment of the invention.

As illustrated at FIGS. 11A-20, it was experimentally verified that an embodiment of a transducer 280 comprising a cylindrical transduction element 281, which was applied to a simulated target tissue, an artificial tissue, and to porcine tissue sample, formed localized, linear thermal treatment zone (TTZ 550) in a targeted focal area 552. In the experiment, the single cylindrical transduction element 281 was constructed with a radius and focal depth of 15 mm. The size of the cylindrical transduction element 281 was 20 mm (azimuth) by 17 mm (elevation). Additional focal gain could be achieved with a larger aperture. Depth is limited by frequency and focal gain, and was set to 6 mm below a simulated tissue surface.

In FIGS. 11A-13B, treatment profiles were plotted based on theoretical and experimental performance with a cylindrical transduction element 281. The normalized pressure is proportional to a thermal heating measure at the specified depth. The spikes (pointed regions at the top of the plots) plots indicate pressure peaks that occur as a result of the geometric edge effects of the geometry of the cylindrical transduction element 281. The spikes are visible in both the theoretical and the experimental performance results. The software simulated experiments reflect the theoretical performance of the 15 mm cylindrical transduction element 281 in FIGS. 11A, 12A, 13A, 14A, 15A, and 16A. The physical experiments in simulated tissue were performed and measured, with results in FIGS. 11B, 12B, 13B, 14B, 15B and 16B.

Figure 14A:
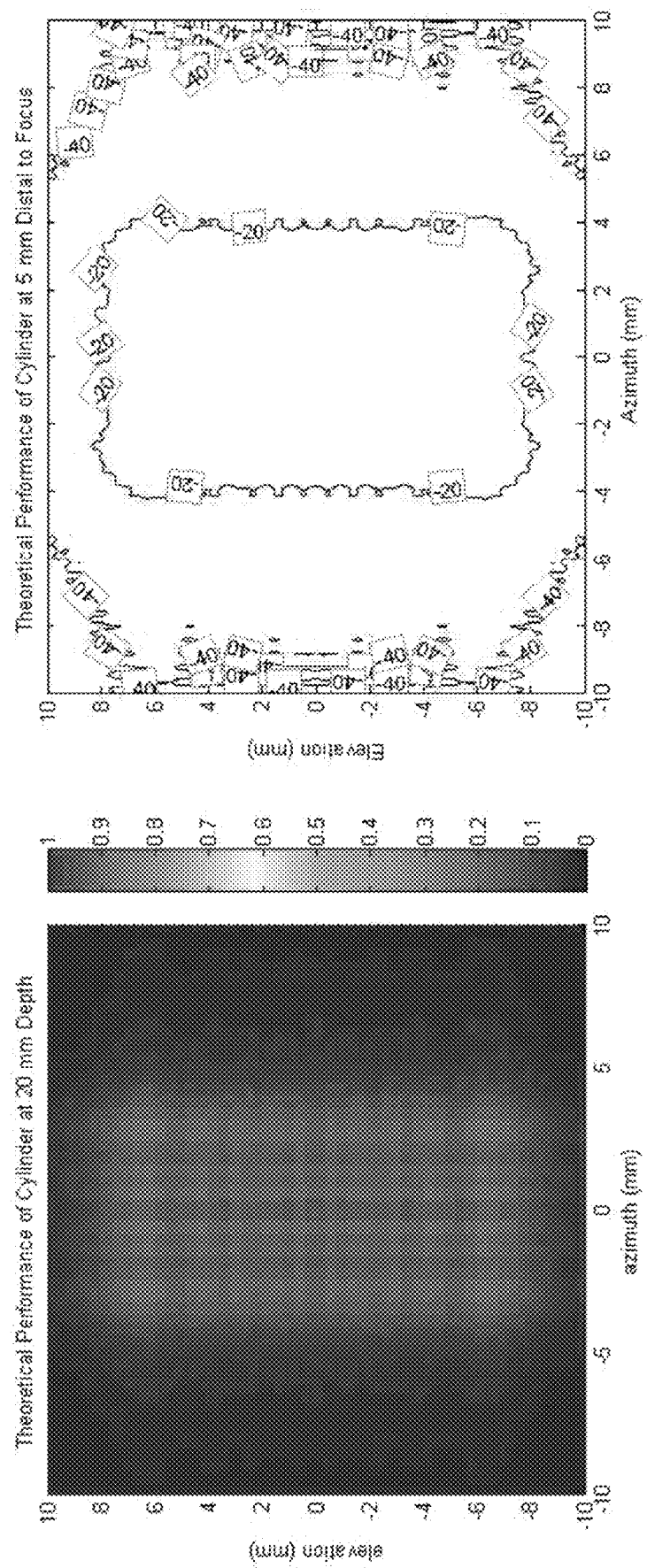
FIGS. 14A-14B are schematic plots illustrating normalized pressure intensity distributions at a depth of 20 mm according to an embodiment of a transducer comprising a cylindrical transduction element.
Figure 14B:
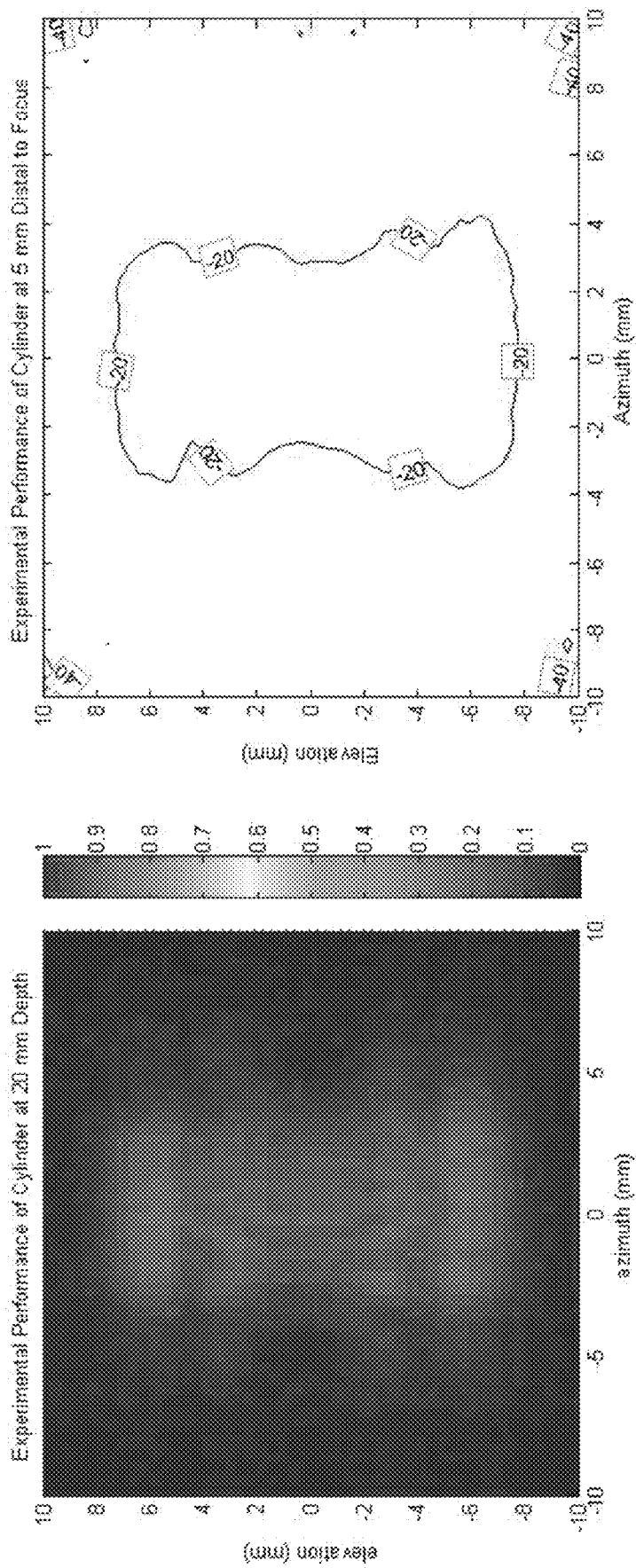
Figure 15A:
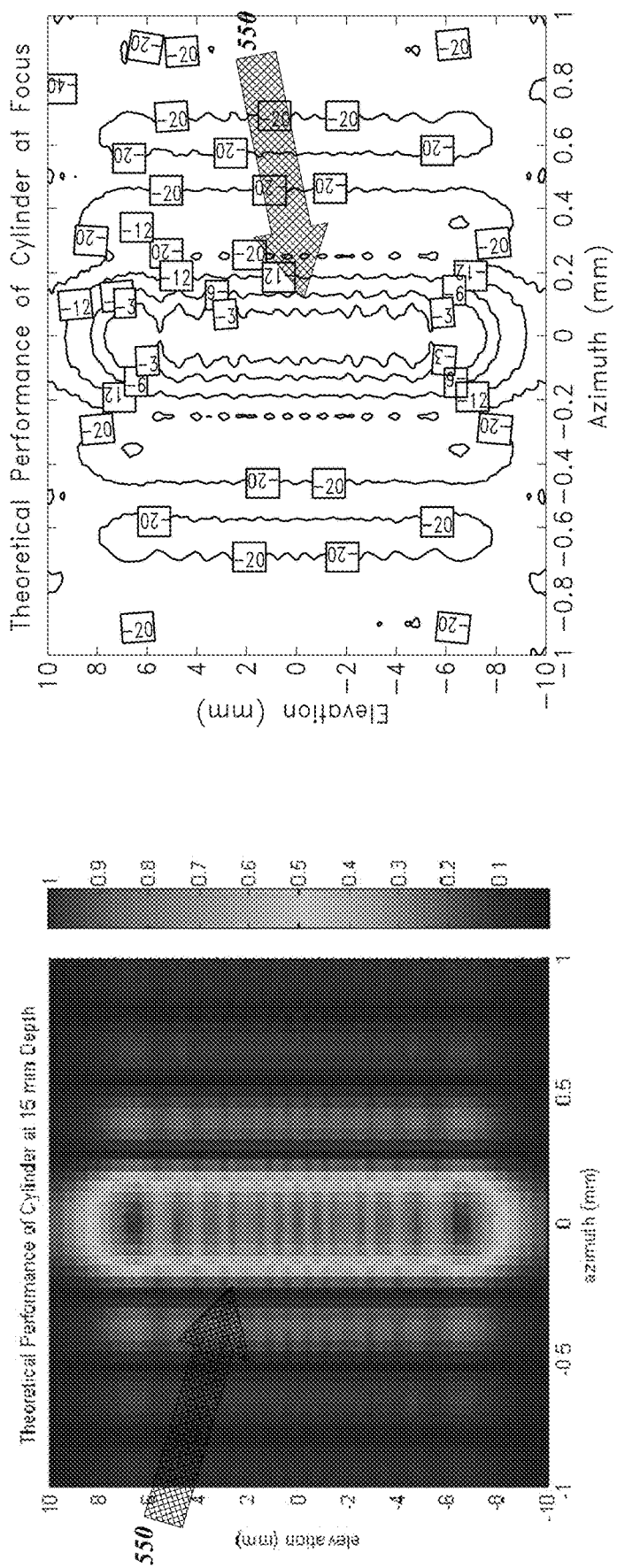
FIGS. 15A-15B are schematic plots illustrating normalized pressure intensity distributions at a depth of 15 mm according to the embodiment of a transducer comprising a cylindrical transduction element of FIG. 11A-11B.
Figure 15B:
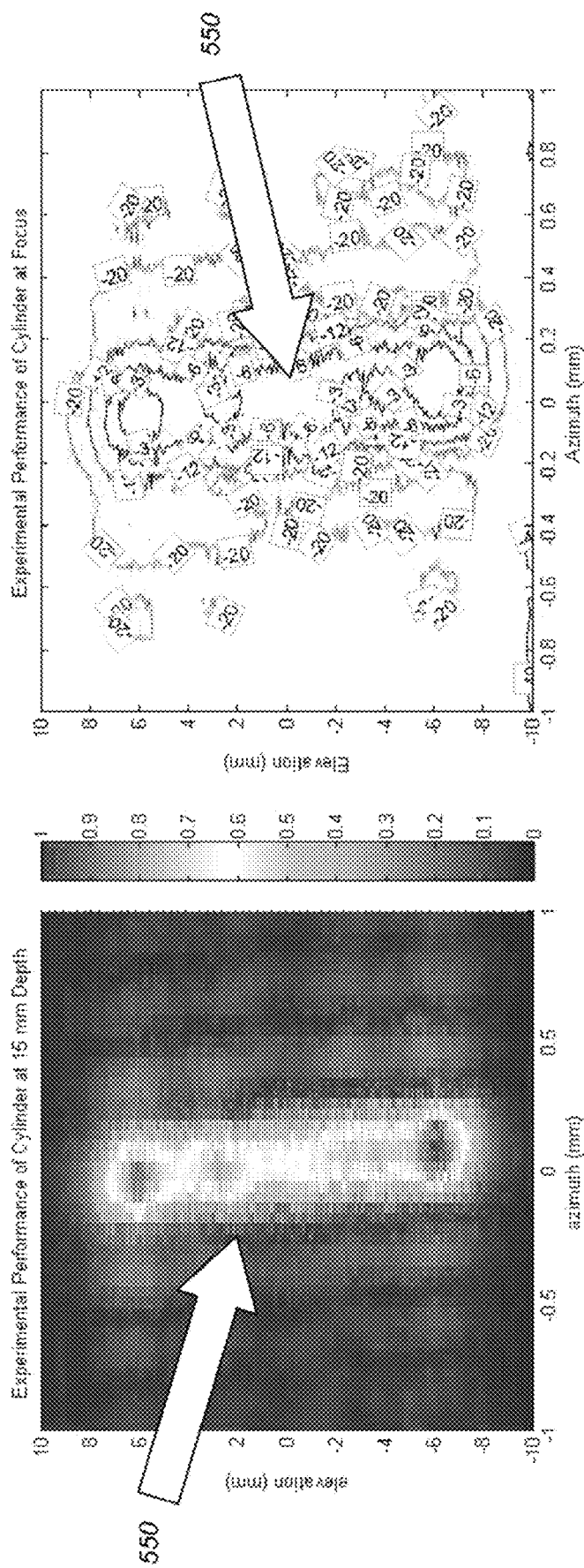
Figure 16A:
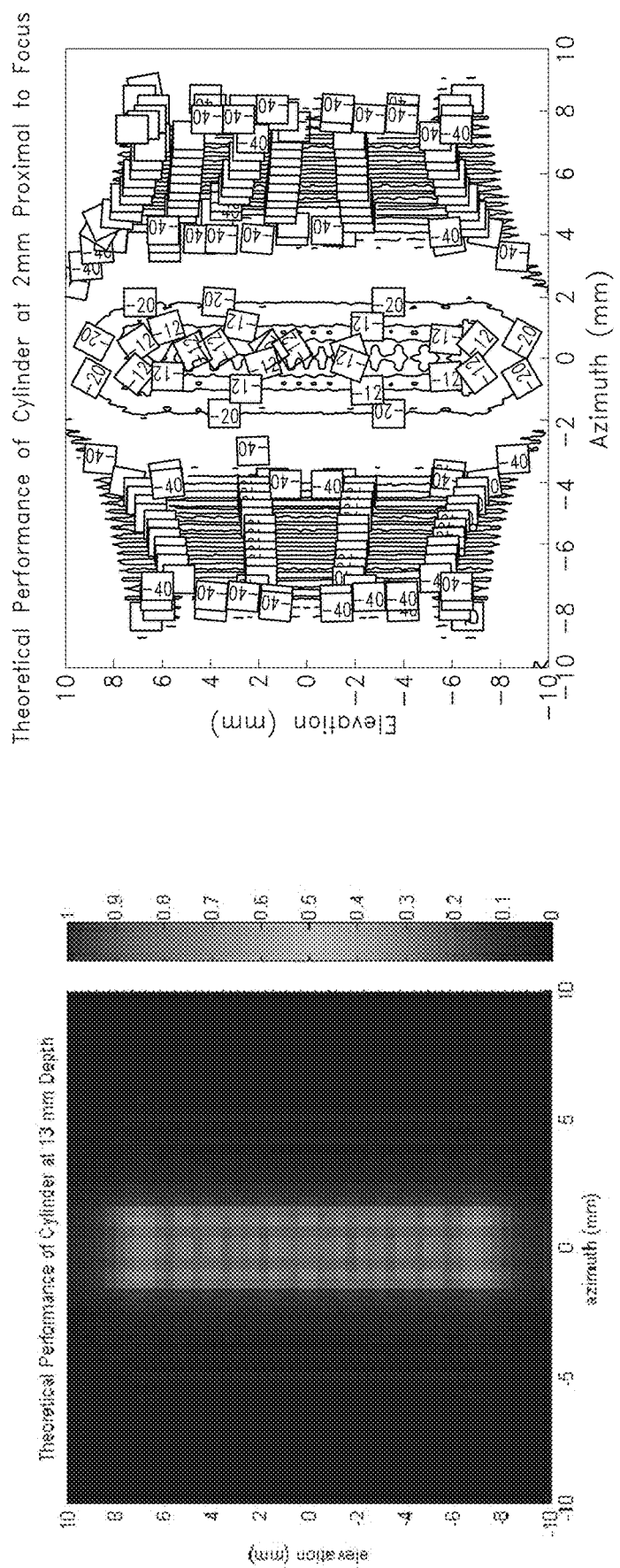
FIGS. 16A-16B are schematic plots illustrating normalized pressure intensity distributions at a depth of 13 mm according to the embodiment of a transducer comprising a cylindrical transduction element of FIG. 11A-11B.
Figure 16B:
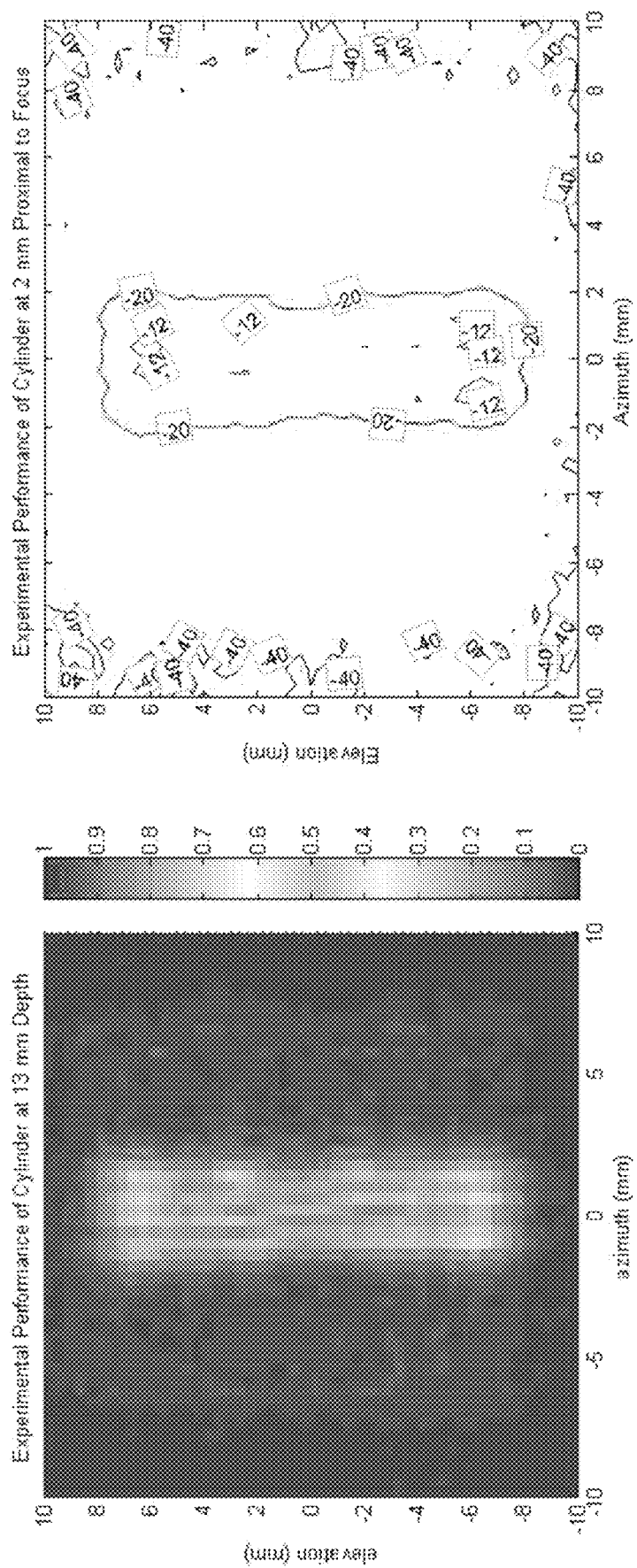

In FIGS. 11A-11B and 14A-14B, the depth is 20 mm, where the normalized pressure peaks at a value of roughly 0.15. As shown in FIG. 14A-14B, the normalized pressure is not visible. In FIGS. 12A-12B and 15A-15B, the depth is the designed, optimal 15 mm, where the normalized pressure peaks at a value of roughly 0.8. As shown in FIG. 15A-15B, the normalized pressure is clearly visible, with peak normalized pressures at approximately 0.9-1.0. The size of the cylindrical transduction element 281 was 20 mm (azimuth) by 17 mm (elevation). The size of the TTZ 550 at a depth of 15 mm was about 0.5 mm thick (along azimuth) by 17 mm width (along elevation). In FIGS. 13A-13B and 16A-16B, the depth is 13 mm, where the normalized pressure peaks at a value of roughly 0.25. As shown in FIG. 16A-16B, the normalized pressure is barely visible. As shown through both the theoretical and experimental data, the normalized pressure corresponding to the TTZ 550 for a 15 mm focal depth cylindrical transduction element 281 is at the 15 mm depth, with a linear TTZ 550.

Figure 17:
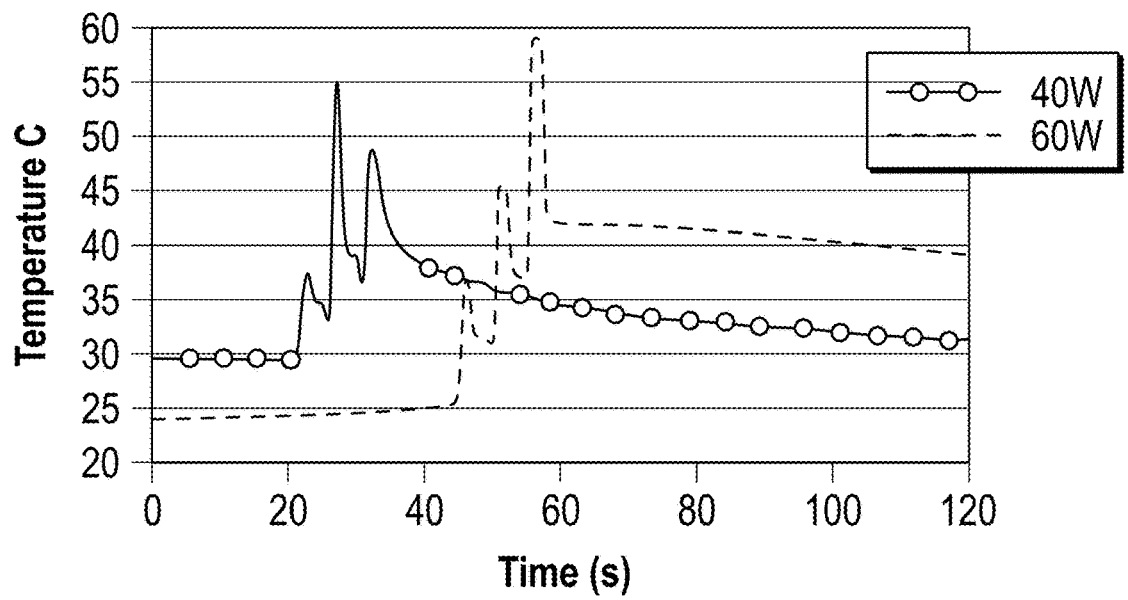
FIG. 17 is a plot illustrating temperature in porcine muscle over time at different power levels for an embodiment of a transducer comprising a cylindrical transduction element.

As illustrated at FIGS. 17-20, it was experimentally verified that the embodiment of a transducer 280 comprising a cylindrical transduction element 281, which was applied to a porcine tissue sample (muscle tissue), formed localized, linear thermal treatment zone (TTZ 550) in a targeted focal area 552. In the experiment, an embodiment of a transducer 280 comprising a cylindrical transduction element 281 was passed over the porcine muscle tissue with three passes in 20 seconds, operating at 4.5 MHz and a tissue depth of 6 mm. As shown in FIG. 17, the three passes (shown with the three spikes in temperature) increased the temperature of the porcine muscle. Two power levels are shown. The 40 W porcine muscle started at 30 degrees Celsius, and over the course of 20 seconds (between the 20 and 40 second marks) of heating through three passes of the cylindrical transduction element 281 over the target tissue region, the temperature spiked to a maximum of about 55 degrees Celsius, then gradually cooled to about 32 degrees Celsius 100 seconds after the start of the treatment. The 60 W porcine muscle started at about 24 degrees Celsius, and over the course of 20 seconds (between the 40 and 60 second marks) of heating through three passes of the cylindrical transduction element 281 over the target tissue region, the temperature spiked to a maximum of about 59 degrees Celsius, then gradually cooled to about 40 degrees Celsius about 80 seconds after the start of the treatment.

Figure 18:
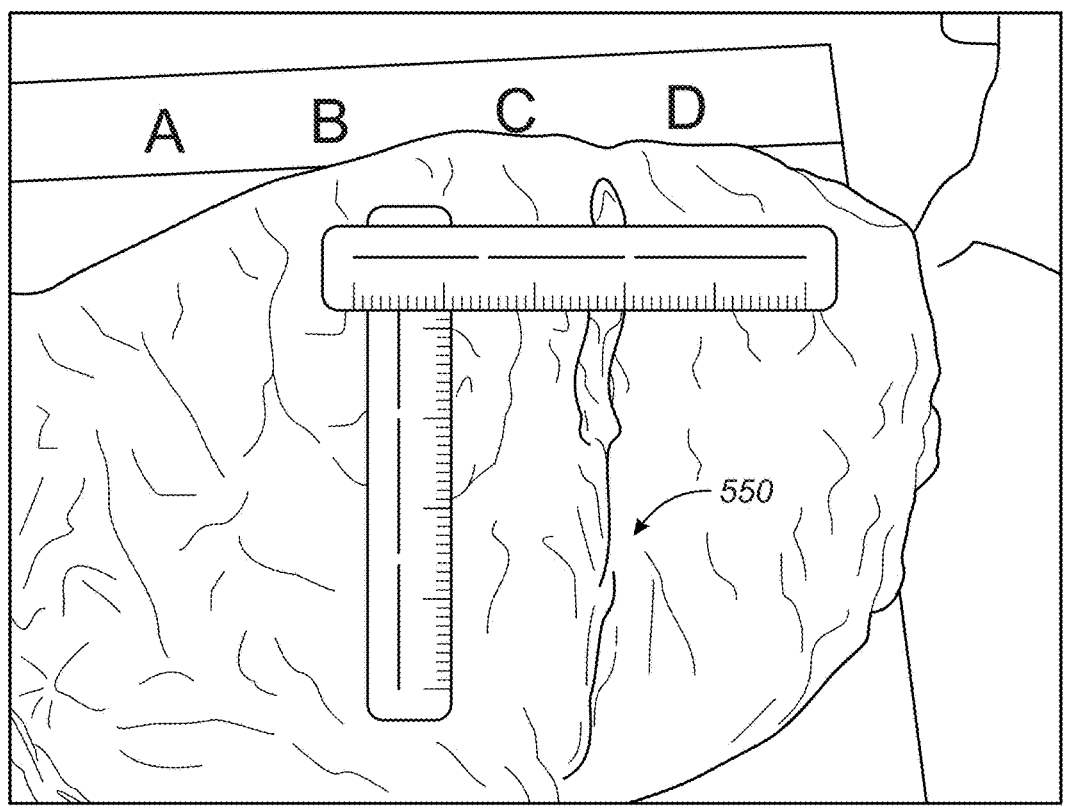
FIG. 18 is a photograph of porcine muscle after experimental treatment confirming confirmed line and plane heating with an embodiment of a transducer comprising a cylindrical transduction element.
Figure 19:
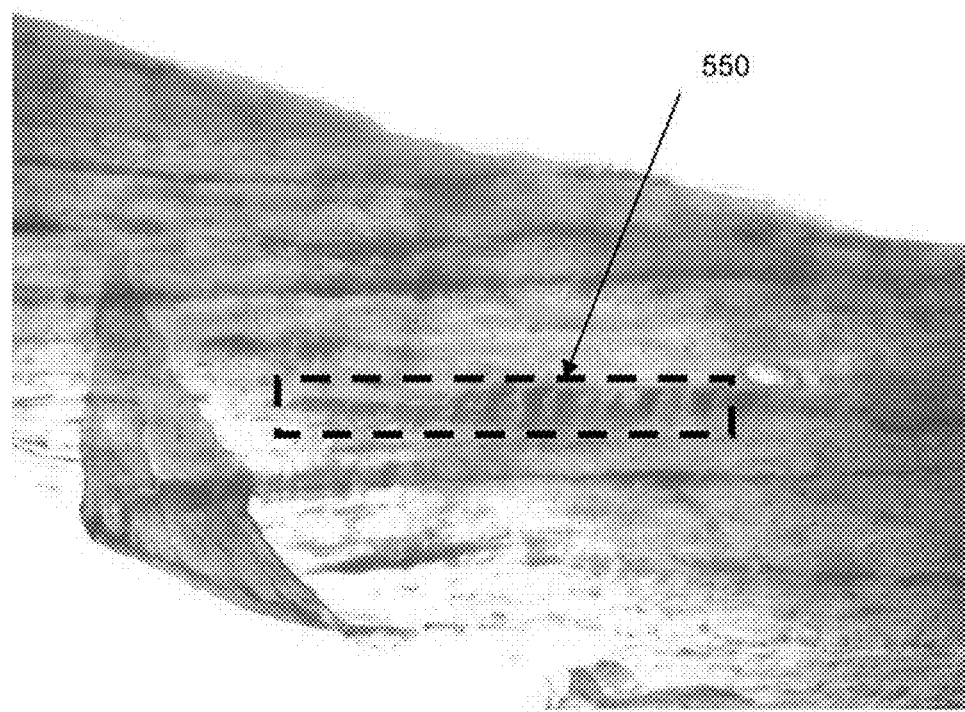
FIG. 19 is a cross-section cut through the porcine muscle in FIG. 18 showing a linear thermal treatment zone.
Figure 20:
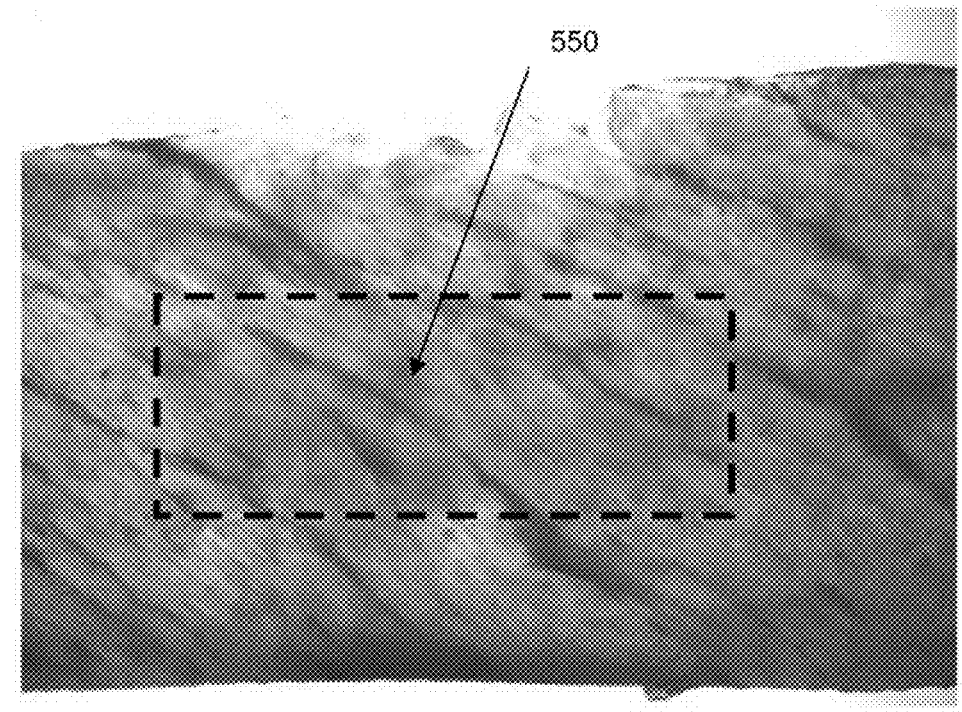
FIG. 20 is an orthogonal cross-section cut through the porcine muscle in FIG. 19 showing a planar thermal treatment zone.

FIG. 18 is a photograph of the porcine muscle after treatment confirming line and plane heating. In one embodiment, the coagulation was dependent on time-off between lines, time-off between passes, and number of passes. Slower temperature rise than thermal coagulation points. FIG. 19 is a cross-section cut through the porcine muscle in FIG. 18 showing a linear thermal treatment zone. FIG. 20 is an orthogonal cross-section cut through the porcine muscle in FIG. 19 showing a planar thermal treatment zone.

Example 2

The following example is intended to be a non-limiting embodiment of the invention.

As illustrated at FIGS. 28-30, it was experimentally verified that an embodiment of a partially coated transducer 600 comprising a cylindrical transduction element 281, which was applied to a simulated target tissue, formed a localized, linear thermal treatment zone (TTZ 550) in a targeted focal area 552. The partially coated transducer 600 includes a first coated region 287 that fully plates the concave surface 282 of the cylindrical transduction element and at least a second coated region 287 that partially plates the convex surface 283 of the cylindrical transduction element. Both the first and the second coated regions 287 of the partially coated transducer 600 are plated with silver. In the experiment, the single cylindrical transduction element 281 was constructed with a radius and focal depth of 15 mm. The size of the cylindrical transduction element 281 was 20 mm (azimuth) by 17 mm (elevation). The cylindrical transduction element 281 had an opening 285 in the center of 4 mm in diameter.

In FIGS. 28, 29 and 30, treatment profiles were plotted based on theoretical performance with a cylindrical transduction element 281. The theoretical performance is proportional the thermal heating at the specified depth. The software simulated experiment reflects the theoretical performance of the 15 mm partially coated transducer 600, showing a consistent linear thermal treatment zone 550 at the 15 mm depth.

Example 3

The following example is intended to be a non-limiting embodiment of the invention.

Multiple in-vivo porcine studies and multiple cadaver studies were conducted to evaluate various embodiments of hardware to perform bulk heating treatments. Early studies focused on specifying and improving the instrumentation necessary to measure subdermal temperatures. In some embodiments, insulated wire thermocouples were placed at focal and subfocal depths by snaking the thermocouple through a needle-bored hole in the skin and verifying the depth with a Siemens s2000 ultrasound device. Temperature profiles were collected using a high sampling DAQ card. Once the measurement setup was defined, a replicated 3-factor 3-level design of experiments was performed in the in-vivo porcine model to determine energy settings that could safely reach isoeffective dosages without causing skin surface damage. In one embodiment, a mean temperature differential of 10 degrees Celsius was observed, with a mean focal heating rate of ~1.2 degrees Celsius/pass. Safe heating rates appear to be similar across transducer.

A thermal dosage study was performed in the in-vivo porcine model after safe heating rates were determined. The study demonstrated an embodiment of the system is capable of reaching isoeffective dosages such as 47 degrees Celsius for 3 minutes, 48 degrees Celsius for 1 minute, and 50 degrees Celsius for 1 minute without exceeding 41 degrees Celsius on the skin surface. In some embodiments, use of higher temperature, shorter exposure time treatments may have the potential to overshoot the target temperature and could overheat the skin surface. In various embodiments, the longer it takes to perform an isoeffective dose, the more heat diffuses to the surrounding tissue and less selective the treatment becomes with depth. Additionally, the longer the isoeffective exposure time, the more impractical the treatment becomes from an operator and ergonomics point of view. For these reasons, in some embodiments, use of higher isoeffective temperatures and shorter exposure times were preferred.

Figure 46:
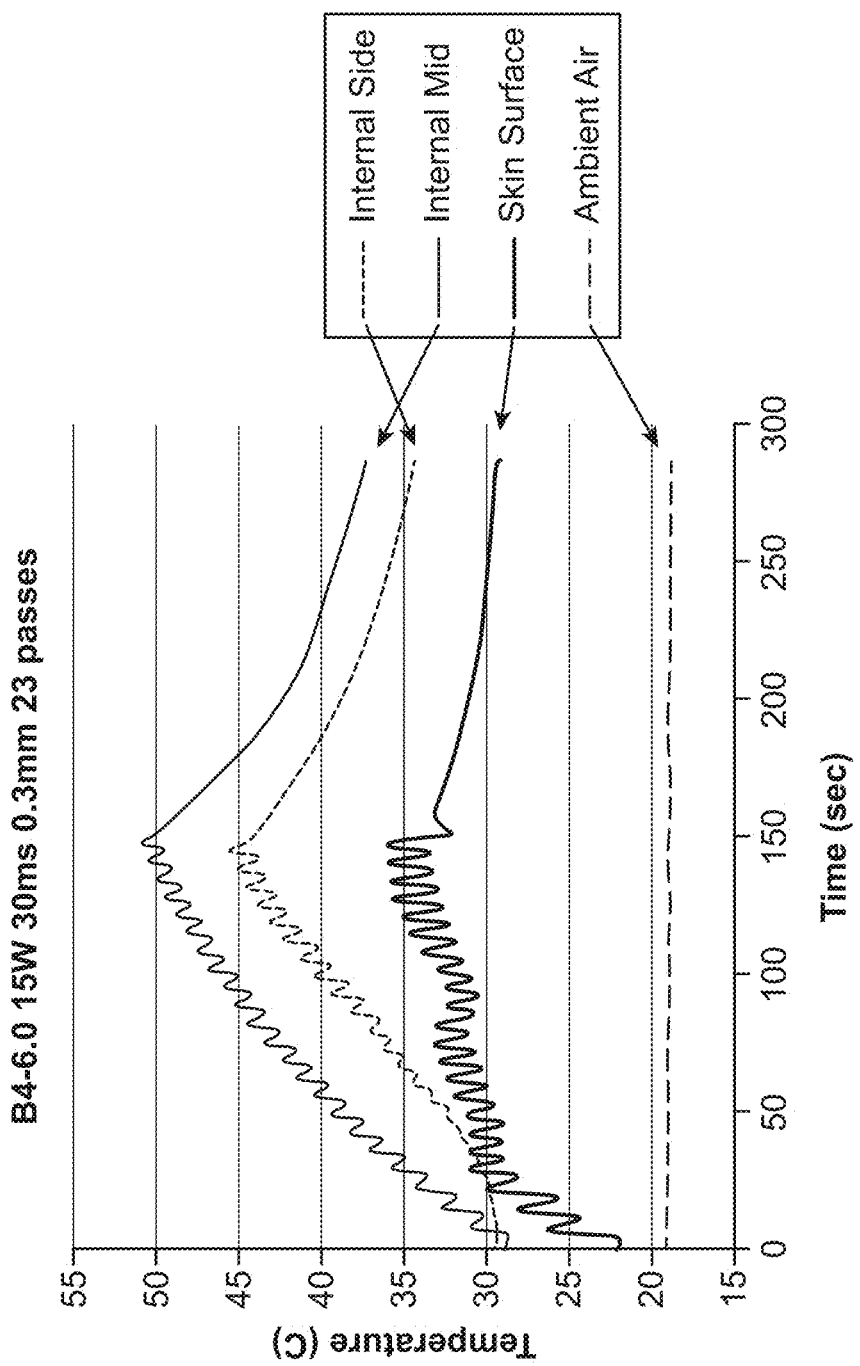
FIG. 46 is a chart illustrating temperature profiles from an embodiment of an in-vivo porcine model treatment dosage study according to an embodiment of the present invention.
Figure 48:
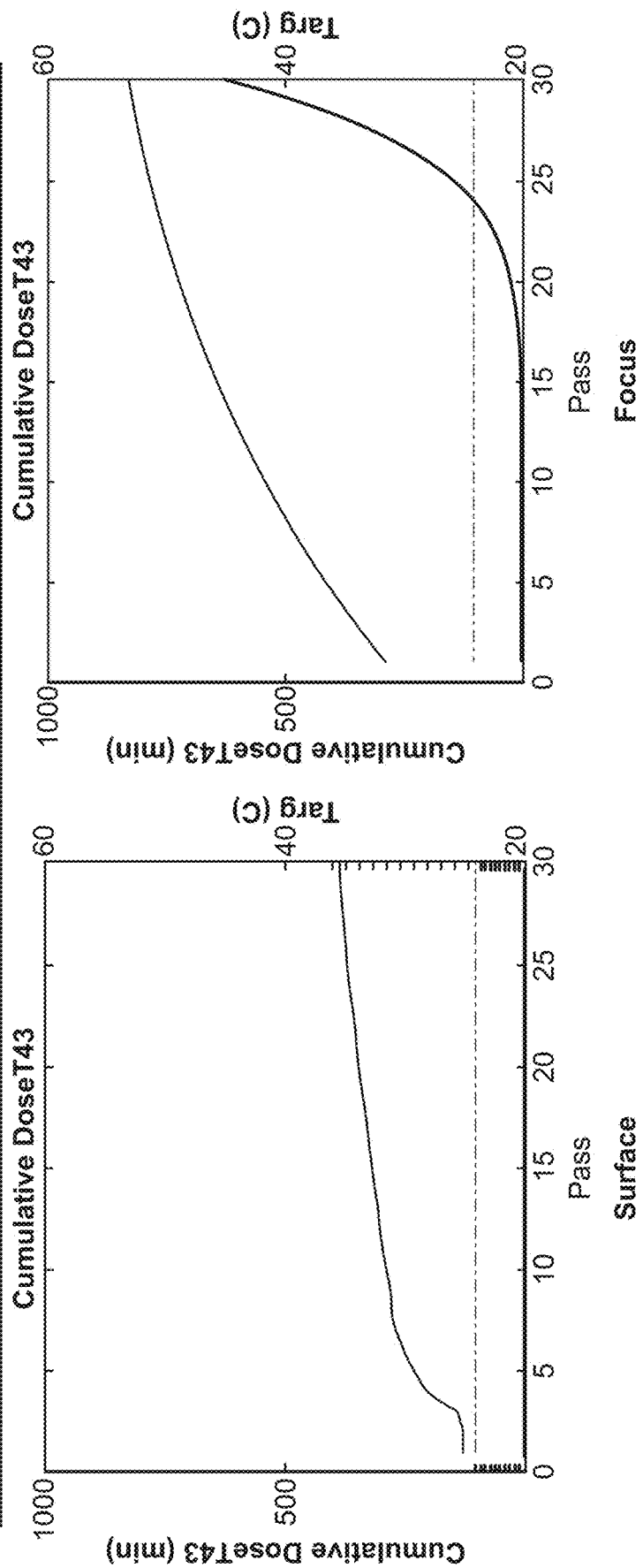
FIG. 48 illustrates cumulative dose relating time, temperature, and pass count of a treatment study according to an embodiment of the present invention.

In-vivo porcine tests were conducted to determine if the candidate treatment settings for submental could cause adverse surface skin effects. The animals procured for these studies were light skinned, 120-140 pound castrated male Yucatan miniature pigs, selected due to its skin characteristics being similar to that of human tissue. Skin surface data was evaluated by monitoring the animal for evidence of erythema, edema, and contusion on the skin surface after treatment. Photographs of each treatment area were taken prior to and following treatment (Cannon G9 and Cannon VIXIA HF 510). In one embodiment, a thermal dosage study using a cylindrical element transducer was performed on in-vivo porcine models. In several embodiments, test sites were able to achieve a significant temperature differential between the focus tissue site and the skin surface without causing damage to the skin surface. FIG. 46 shows the temperature profiles from an embodiment of an in-vivo porcine model treatment in which the temperature profile reached 50 degrees Celsius for several seconds without the skin surface exceeding 41 degrees Celsius, and shows a temperature differential of as much as 15 degrees Celsius between the focus tissue site and the skin surface. The temperature change accrued from a single pass of treatment is sufficiently small (approximately 0.9 degrees Celsius/pass or 0.13 degrees Celsius/sec) to perform corrective action and maintain a target temperature within +/−1 degrees Celsius. A modified 3-factor 3-level design of experiments was performed in the in-vivo porcine model to determine a range of energy settings that could safely reach the isoeffective dosages temperatures shown in FIG. 42. The settings, according to various embodiments, are tabulated in the table at FIG. 47. The Design of Experiments (DOE) tests an acoustic power range of 10-20 W, exposure times of 20-40 ms, and spacings in the range of 0.1-0.3 mm. FIG. 48 shows an embodiment of a treatment setting that was able to achieve a relatively high thermal dosage at the focus with little to no dose or temperature increase at the skin surface. The focus achieves a thermal dose of 100 equivalent minutes (red-dashed line) at T=43 degrees Celsius on the 24th pass, which corresponds to a theoretical survival fraction of 1% according to FIG. 42. In various embodiments, similar temperature rises and heating rates were achieved at the focus and surface across various embodiments of transducers for treatments that did not cause significant skin surface damage. A mean temperature differential of 10 degrees Celsius was observed, with a mean focal heating rate of ~1.2 degrees Celsius/pass. The largest temperature differential between the focus and the skin was achieved by the 3.5 MHz, 22 mm width, 6.0 depth design which had an average difference of 12 degrees Celsius across treatments. Since the heating rates that produce little to no surface effects are similar across transducer, the 3.5 MHz, 22 mm width, 6.0 mm depth transducer was selected to be assessed in a thermal dosage study.

Figure 51:
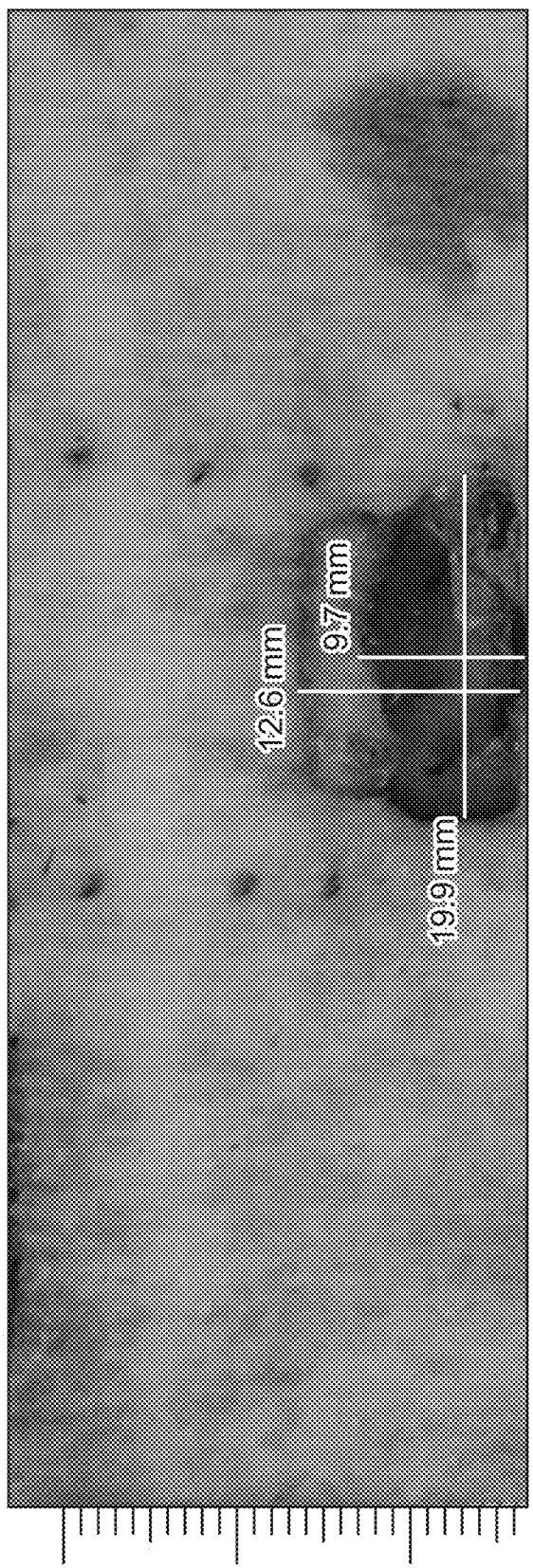
FIG. 51 is an image of a thermally overdosed site with a transducer according to an embodiment of the present invention.
Figure 52:
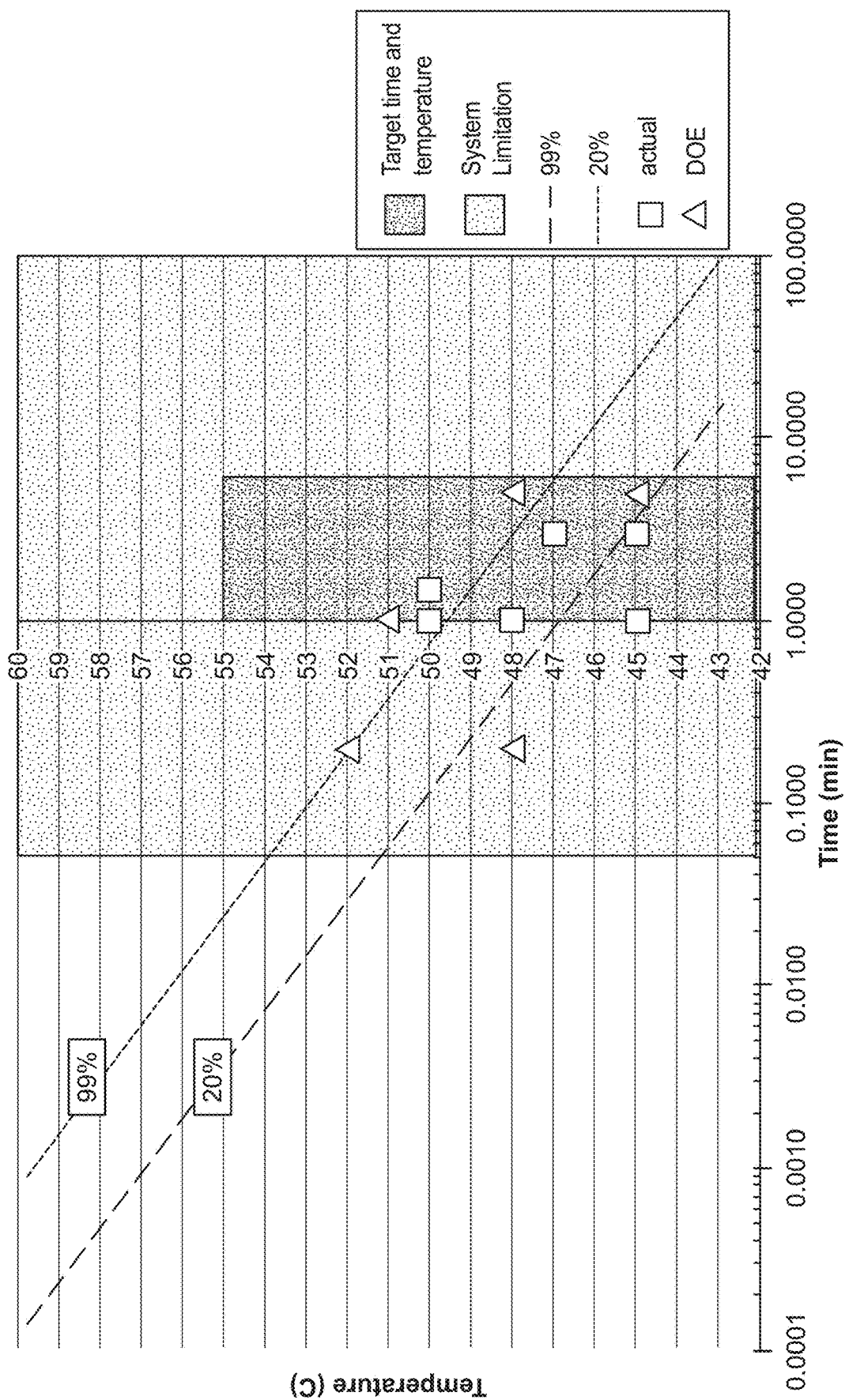
FIG. 52 is chart relating time and temperature with target goal temperatures according to an embodiment of the present invention.

In various embodiments, thermal dosage studies were performed on in-vivo porcine and cadaver models to determine safe isoeffective dosages, and the geometry of adipocyte death through histological evaluation. The Table at FIG. 49 tabulates the target time-temperature exposures to achieve different levels of adipocyte death. According to the empirical data in FIG. 42, Site 2 and 5 should achieve little to no adipocyte death. Sites 3, 6 and 7 should achieve a high degree of adipocyte death. Sites 1 and 4 are within the transition region and should achieve a moderate amount of adipocyte death. The table at FIG. 50 lists the energy settings used to approach each isoeffective dose using a 3.5 MHz, 22 mm width, 6.0 mm depth transducer. In various embodiments, treatments were active for 2-3 minutes with 20-30 pulses to reach the target temperature with a 1 degrees Celsius/pass ramp followed by maintenance pulses ever 3-5 seconds. A few test sites showed mild surface effects the day of treatment, only to become more pronounced as the injury rose to the skin surface. FIG. 51 shows one site that was treated aggressively for the purpose of coagulating tissue for histological control through overdosing. In the embodiment in FIG. 51, the dimension of the lesion represents a an example of the spread of thermal energy, measuring 12.6× 19.9 mm on the skin surface with a depth of edema that can be detected up to 12 mm from the skin surface. A visual representation of the time-temperature goals listed in the table at FIG. 49 is shown in FIG. 52 (triangle marks), with six isoeffective dosages achieved in the lab are overlayed in FIG. 52 (square marks). Two of these isoeffective dosages fall in the coagulative region, two fall in the transition region, and two in the hyperthermia region.

Some embodiments and the examples described herein are examples and not intended to be limiting in describing the full scope of compositions and methods of these invention(s). Equivalent changes, modifications and variations of some embodiments, materials, compositions and methods can be made within the scope of the embodiments herein. In various embodiments, a device or method can combine features or characteristics of any of the embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "coupling an ultrasound probe to a skin surface" include "instructing the coupling of an ultrasound probe to a skin surface." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 25 mm" includes "25 mm." The terms "approximately", "about", and "substantially" as used herein represent an amount or characteristic close to the stated amount or characteristic that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount or characteristic.

What is claimed is:

1. A method of reducing variance in focal gain in a planar band treatment area for heating tissue with a cylindrically focused ultrasound transducer, comprising:
   applying a current from a power source to a cylindrical transduction element to form a linear focal zone at a focal depth,
   moving the cylindrical transduction element with a motion mechanism along a linear path perpendicular to the linear focal zone to produce a planar band treatment area, and
   reducing a variance in focal gain at the linear focal zone at the focal depth by applying an electrical signal to a portion of the cylindrical transduction element, the cylindrical transduction element comprising a first surface, a second surface, a plurality of coated regions, and an uncoated region,
   wherein the plurality of coated regions comprises an electrical conductor,
   wherein the first surface comprises at least one coated region of the plurality of the coated regions,
   wherein the second surface comprises the uncoated region and a subset of the plurality of coated regions,
   wherein the subset of the plurality of coated regions on the second surface cover at least 60% of the second surface,
   wherein the subset of the plurality of coated regions on the second surface comprise a lateral edge, a medial edge, a first side edge, and a second side edge, and the portion of the cylindrical transduction element comprises the subset of the plurality of coated regions,
wherein the applying the signal to the subset of the plurality of coated regions directs uniform ultrasound energy with a reduced focal gain to the linear focal zone at the focal depth.

2. The method of claim 1, wherein the reducing the focal gain facilitates the efficient and consistent treatment of tissue, wherein the cylindrical transduction element applies ultrasonic therapy to a thermal treatment zone at the focal depth.

3. The method of claim 1, wherein the reducing the focal gain reduces a peak such that a variance around the focal depth is reduced by 75-200%.

4. The method of claim 1, wherein the reducing the focal gain reduces a peak such that a variance of an intensity around the focal depth is 5 mm or less.

5. The method of claim 1, wherein the reducing the focal gain reduces a variance in focal gain in a range of 0.01-10.

6. The method according to claim 1, wherein the cylindrical transduction element is housed within an ultrasonic hand-held probe, wherein the ultrasonic probe comprises:
a housing,
the cylindrical transduction element, and
the motion mechanism;
wherein the ultrasound transducer is movable within the housing,
wherein the motion mechanism is attached to the ultrasound transducer, and further comprising stopping the ultrasound transducer along the linear path within the housing.

7. A method of reducing variance in focal gain in a planar band treatment area for heating tissue with a cylindrically focused ultrasound transducer, comprising:
using a cylindrical transduction element to reduce edge noise at a linear focal zone at a focal depth by reducing a variance in a focal gain in a range of 0.01-10 by driving the cylindrical transduction element with a power source for applying ultrasonic energy to the linear focal zone at the focal depth,
wherein the driving the cylindrical transduction element comprises applying an electric signal from the power source to a plurality of electrically conductive coated regions on the cylindrical transduction element, and
moving the cylindrical transduction element with a motion mechanism along a linear path perpendicular to the linear focal zone to produce a uniform, planar heating area.

8. The method of claim 7,
wherein the cylindrical transduction element comprises a first surface and a second surface,
wherein the first surface comprises an electrically conductive coating fully covering the first surface,
wherein the second surface comprises two electrically conductive coated regions and at least one region that is not coated with an electrically conductive coating,
wherein the two coated regions on the second surface comprises a conductive material that forms an electrode when the power source is in electric communication with each coated region,
wherein the conductive material comprises silver;
wherein the coated regions on the second surface cover at least 80% of the second surface;
wherein the coated regions on the second surface comprise a lateral edge, a medial edge, a first side edge, and a second side edge, wherein the driving the cylindrical transduction element comprises applying an electric signal from the power source to the coated regions on the second surface.

9. The method of claim 7, wherein the first surface is a concave surface and the second surface is a convex surface.

10. The method of claim 7, wherein the cylindrical transduction element is housed within an ultrasonic hand-held probe, wherein the ultrasonic probe comprises:
a housing,
the cylindrical transduction element, and
a motion mechanism;
wherein the ultrasound transducer is movable within the housing,
wherein the motion mechanism is attached to the ultrasound transducer, and further comprising moving the ultrasound transducer along a linear path within the housing.

11. The method of claim 10, further comprising moving the cylindrical transduction element with the motion mechanism to heat a treatment area at the focal depth to a temperature in a range between 40-65 degrees Celsius.

12. The method of claim 7, further comprising producing a uniform temperature in a treatment area with the cylindrical transduction element in a range of 42-55 degrees Celsius in the material at the focal depth.

13. The method of claim 7, further comprising imaging the material with one or more imaging elements, wherein the cylindrical transduction element further comprises an opening for placement of the one or more imaging elements.

14. A method of reducing variance in focal gain in a planar band treatment area for heating tissue with a cylindrically focused ultrasound transducer, comprising:
using a cylindrical transduction element to reduce edge noise at a linear focal zone at a focal depth with the cylindrical transduction element by reducing a variance of an intensity around the focal depth to 5 mm or less by driving the cylindrical transduction element with a power source for applying ultrasonic energy to the linear focal zone at the focal depth,
wherein the driving the cylindrical transduction element comprises applying an electric signal from the power source to a plurality of coated regions on the cylindrical transduction element, and
moving the cylindrical transduction element with a motion mechanism along a linear path perpendicular to the linear focal zone to produce a uniform, planar heating area.

15. The method of claim 14,
wherein the cylindrical transduction element comprises a first surface and a second surface,
wherein the first surface comprises an electrically conductive coating,
wherein the second surface comprises at least two electrically conductive coated regions and at least one region that is not coated with an electrically conductive coating,
wherein the at least two coated regions on the second surface comprises a conductive material that forms an electrode when the power source is in electric communication with the at least two coated regions,
wherein the conductive material comprises any one or more of the group consisting of: silver, copper, gold, and chrome;
wherein the coated regions on the second surface comprise curved edges and straight edges;
wherein the coated regions on the second surface cover at least 70% of the second surface, wherein the driving the cylindrical transduction element comprises applying an electric signal from the power source to the at least two electrically conductive coated regions on the second surface.

16. The method of claim 14, wherein the cylindrical transduction element is housed within an ultrasonic handheld probe, wherein the ultrasonic probe comprises:
a housing,
the cylindrical transduction element, and
a motion mechanism;
wherein the ultrasound transducer is movable within the housing,
wherein the motion mechanism is attached to the ultrasound transducer, and further comprising moving the ultrasound transducer along a linear path within the housing.

17. The method of claim 14, further comprising moving the cylindrical transduction element with the motion mechanism to heat a treatment area at the focal depth to a temperature in a range between 40-65 degrees Celsius.

18. The method of claim 14, wherein the reducing edge noise facilitates the production of a uniform temperature in a treatment area.

19. The method of claim 14, wherein the power source drives the cylindrical transduction element to produce a temperature in a range of 42-55 degrees Celsius in a tissue at the focal depth.

20. The method of claim 14, further comprising one or more imaging elements, wherein the cylindrical transduction element has an opening for placement of the one or more imaging elements.

* * * * *